US011219532B2

(12) United States Patent
Suddaby

(10) Patent No.: US 11,219,532 B2
(45) Date of Patent: Jan. 11, 2022

(54) STAND-ALONE EXPANDABLE INTERBODY SPINAL FUSION DEVICE WITH LOCKING MECHANISM

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 242 days.

(21) Appl. No.: 16/222,086

(22) Filed: Dec. 17, 2018

(65) Prior Publication Data
US 2019/0110900 A1    Apr. 18, 2019

Related U.S. Application Data

(63) Continuation-in-part of application No. 15/707,756, filed on Sep. 18, 2017, now Pat. No. 10,596,010.

(51) Int. Cl.
*A61F 2/44* (2006.01)
*A61F 2/30* (2006.01)
*A61F 2/46* (2006.01)

(52) U.S. Cl.
CPC ............ *A61F 2/4425* (2013.01); *A61F 2/447* (2013.01); *A61F 2/4455* (2013.01); *A61F 2/4611* (2013.01); *A61F 2002/30373* (2013.01); *A61F 2002/30471* (2013.01); *A61F 2002/30492* (2013.01); *A61F 2002/30507* (2013.01); *A61F 2002/30538* (2013.01); *A61F 2002/30593* (2013.01); *A61F 2002/30904* (2013.01)

(58) Field of Classification Search
CPC .................................. A61F 2/44; A61F 2/447
See application file for complete search history.

(56) References Cited

U.S. PATENT DOCUMENTS

| | | | |
|---|---|---|---|
| 5,505,732 | A | 4/1996 | Michelson |
| 5,653,762 | A | 8/1997 | Pisharodi |
| 5,665,122 | A | 9/1997 | Kambin |
| 5,683,463 | A | 11/1997 | Godefroy et al. |
| 5,827,328 | A | 10/1998 | Buttermann |
| 6,176,881 | B1 | 1/2001 | Schär et al. |
| 6,190,414 | B1 | 2/2001 | Young et al. |
| 6,395,034 | B1 | 5/2002 | Suddaby |
| 6,524,341 | B2 | 2/2003 | Läng et al. |
| 6,837,850 | B2 | 1/2005 | Suddaby |
| 6,958,077 | B2 | 10/2005 | Suddaby |
| 6,969,405 | B2 | 11/2005 | Suddaby |
| 6,991,653 | B2 | 1/2006 | White et al. |

(Continued)

OTHER PUBLICATIONS

Sahara Al Expandable Stabilization System; Advertisement flyer; Available from K2M, Inc. Leesburg, Virginia; Published as early as Oct. 20, 2015.

(Continued)

*Primary Examiner* — Christopher J Beccia
(74) *Attorney, Agent, or Firm* — Simpson & Simpson, PLLC; Michael Nicholas Vranjes

(57) ABSTRACT

An expandable interbody spinal fusion device, including an inferior component including at least one hole, a superior component connected to the inferior component, the superior component including a plurality of catches operatively arranged to align with the at least one hole, and a locking screw operatively arranged to engage the plurality of catches and the at least one hole to lock the superior component with respect to the inferior component.

20 Claims, 32 Drawing Sheets

(56) References Cited

U.S. PATENT DOCUMENTS

| | | | |
|---|---|---|---|
| 7,309,358 B2 | 12/2007 | Berry et al. | |
| 7,597,714 B2 | 10/2009 | Suddaby | |
| 7,615,078 B2 | 11/2009 | White et al. | |
| 7,628,800 B2 | 12/2009 | Sherman et al. | |
| 7,648,529 B2 | 1/2010 | An et al. | |
| 7,731,752 B2 | 6/2010 | Edie et al. | |
| 8,007,535 B2 | 8/2011 | Hudgins et al. | |
| 8,057,549 B2 | 11/2011 | Butterman et al. | |
| 8,070,817 B2 * | 12/2011 | Gradl | A61F 2/44 623/17.16 |
| 8,187,328 B2 | 5/2012 | Melkent | |
| 8,241,363 B2 * | 8/2012 | Sommerich | A61F 2/4611 623/17.16 |
| 8,246,630 B2 | 8/2012 | Manzi et al. | |
| 8,273,126 B2 | 9/2012 | Lindner | |
| 8,303,663 B2 | 11/2012 | Jimenez et al. | |
| 8,435,296 B2 | 5/2013 | Kadaba et al. | |
| 8,480,738 B2 | 7/2013 | Edie et al. | |
| 8,512,406 B2 | 8/2013 | White et al. | |
| 8,568,481 B2 | 10/2013 | Olmos et al. | |
| 8,696,751 B2 | 4/2014 | Ashley et al. | |
| 8,900,312 B2 | 12/2014 | McLean et al. | |
| 8,932,302 B2 | 1/2015 | Jimenez et al. | |
| 8,956,413 B2 | 2/2015 | Ashley et al. | |
| 8,992,620 B2 | 3/2015 | Ashley et al. | |
| 9,005,291 B2 * | 4/2015 | Loebl | A61F 2/4425 623/17.15 |
| 9,011,499 B1 | 4/2015 | Kiester | |
| 9,066,760 B2 | 6/2015 | Taber et al. | |
| 9,078,767 B1 | 7/2015 | McLean | |
| 9,084,686 B1 | 7/2015 | McLean et al. | |
| 9,889,019 B2 | 2/2018 | Rogers et al. | |
| 2003/0191531 A1 | 10/2003 | Berry et al. | |
| 2007/0123987 A1 * | 5/2007 | Bernstein | A61F 2/44 623/17.11 |
| 2007/0250172 A1 | 10/2007 | Moskowitz et al. | |
| 2008/0004705 A1 * | 1/2008 | Rogeau | A61F 2/44 623/17.16 |
| 2008/0058930 A1 | 3/2008 | Edie et al. | |
| 2008/0140207 A1 | 6/2008 | Olmos et al. | |
| 2008/0215153 A1 | 9/2008 | Butterman et al. | |
| 2010/0004752 A1 | 1/2010 | White et al. | |
| 2010/0057204 A1 | 3/2010 | Kadaba et al. | |
| 2010/0076559 A1 | 3/2010 | Bagga et al. | |
| 2010/0198352 A1 | 8/2010 | Edie et al. | |
| 2011/0130835 A1 | 6/2011 | Ashley et al. | |
| 2012/0059479 A1 | 3/2012 | Buttermann et al. | |
| 2012/0116518 A1 | 5/2012 | Grotz et al. | |
| 2013/0131808 A1 | 5/2013 | Suh et al. | |
| 2013/0231747 A1 | 9/2013 | Olmos et al. | |
| 2013/0253650 A1 | 9/2013 | Ashley et al. | |
| 2013/0261748 A1 | 10/2013 | Ashley et al. | |
| 2014/0012383 A1 | 1/2014 | Triplett et al. | |
| 2014/0188225 A1 * | 7/2014 | Dmuschewsky | A61F 2/442 623/17.16 |
| 2014/0207236 A1 | 7/2014 | Prevost et al. | |
| 2014/0277476 A1 | 9/2014 | McLean et al. | |
| 2014/0277480 A1 | 9/2014 | Prevost et al. | |
| 2014/0343678 A1 * | 11/2014 | Suddaby | A61F 2/4611 623/17.16 |
| 2015/0012098 A1 | 1/2015 | Eastlack et al. | |
| 2015/0081022 A1 | 3/2015 | McLean et al. | |
| 2015/0148907 A1 | 5/2015 | Kleiner et al. | |
| 2018/0116818 A1 | 5/2018 | Rogers et al. | |
| 2018/0206999 A1 | 7/2018 | Suddaby | |
| 2018/0303626 A1 | 10/2018 | Rogers et al. | |
| 2019/0175357 A1 * | 6/2019 | Sharabani | A61F 2/4455 |

OTHER PUBLICATIONS

Loubert S. Suddaby; Unpublished U.S. Appl. No. 15/273,032; Expandable Intervertebral Fusion Implant, filed Sep. 22, 2016.

* cited by examiner

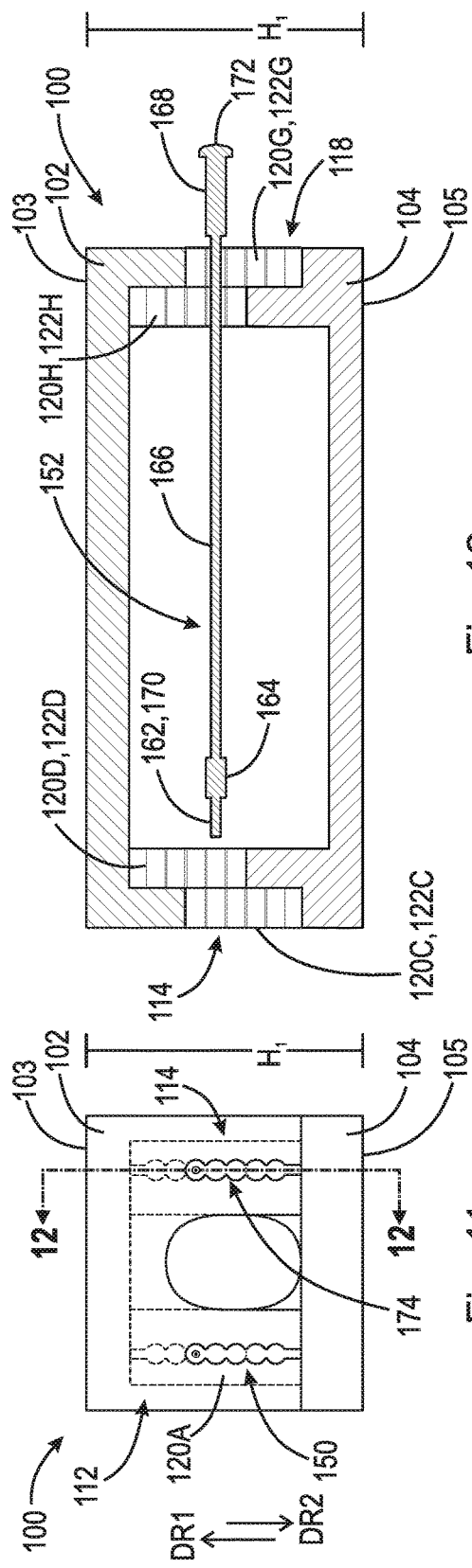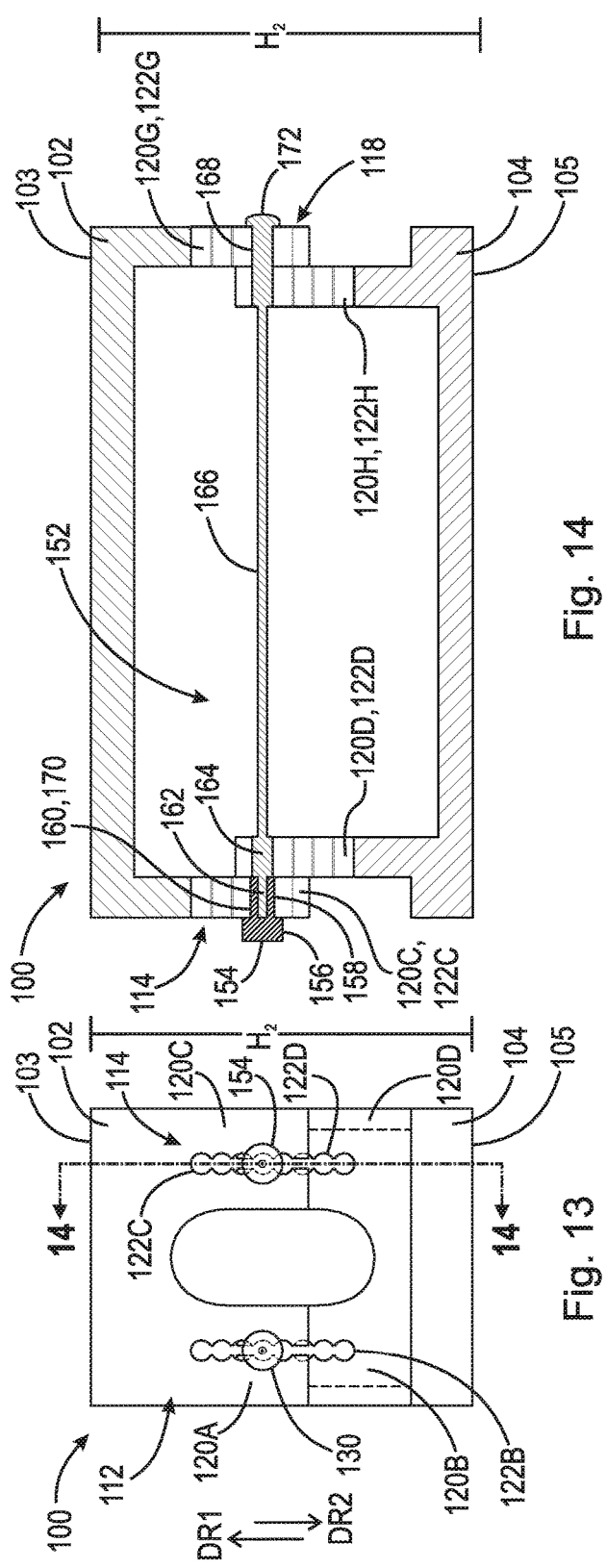

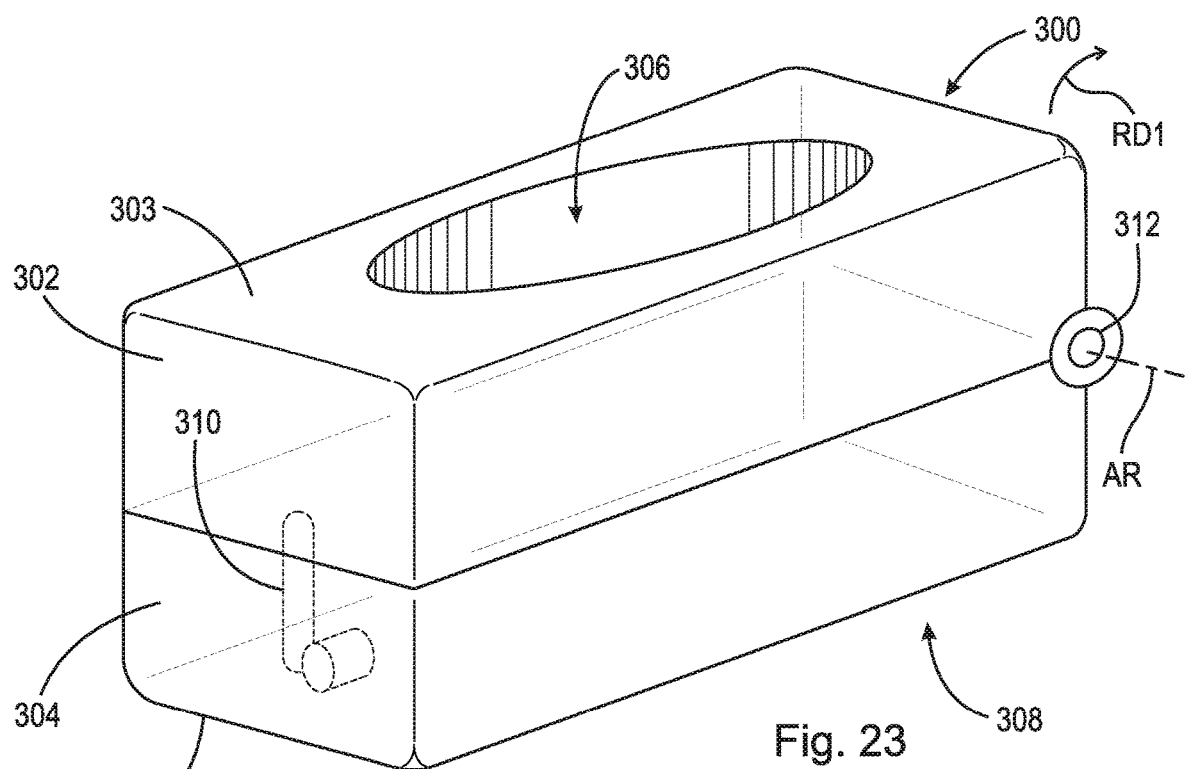
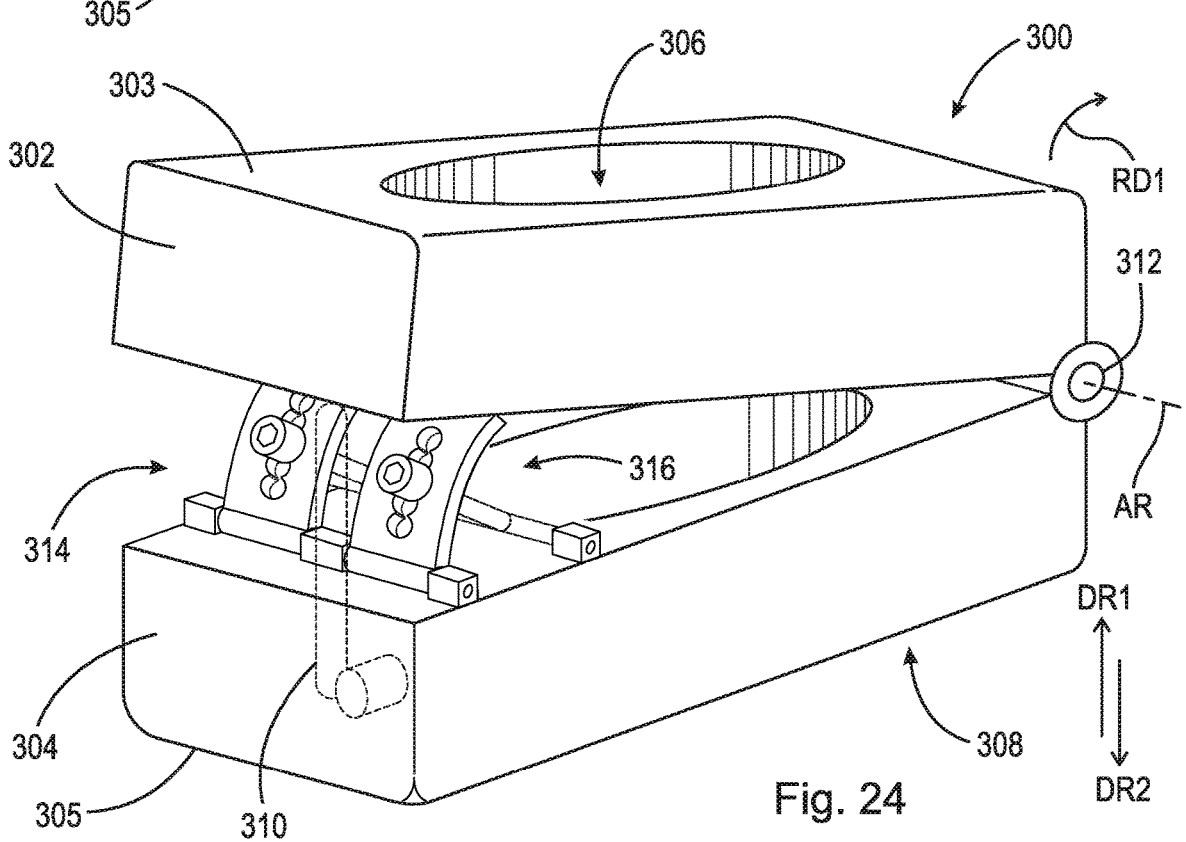

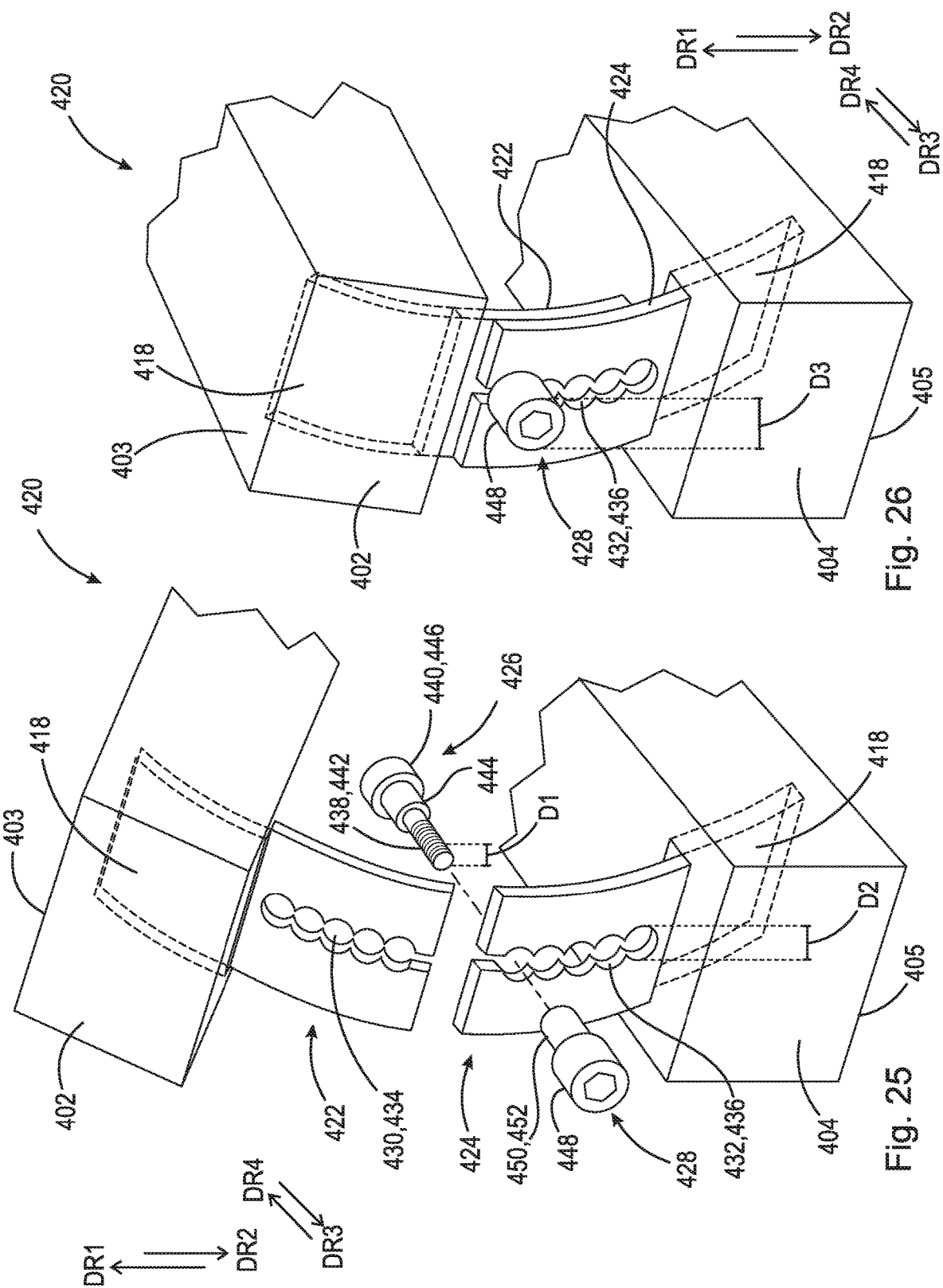

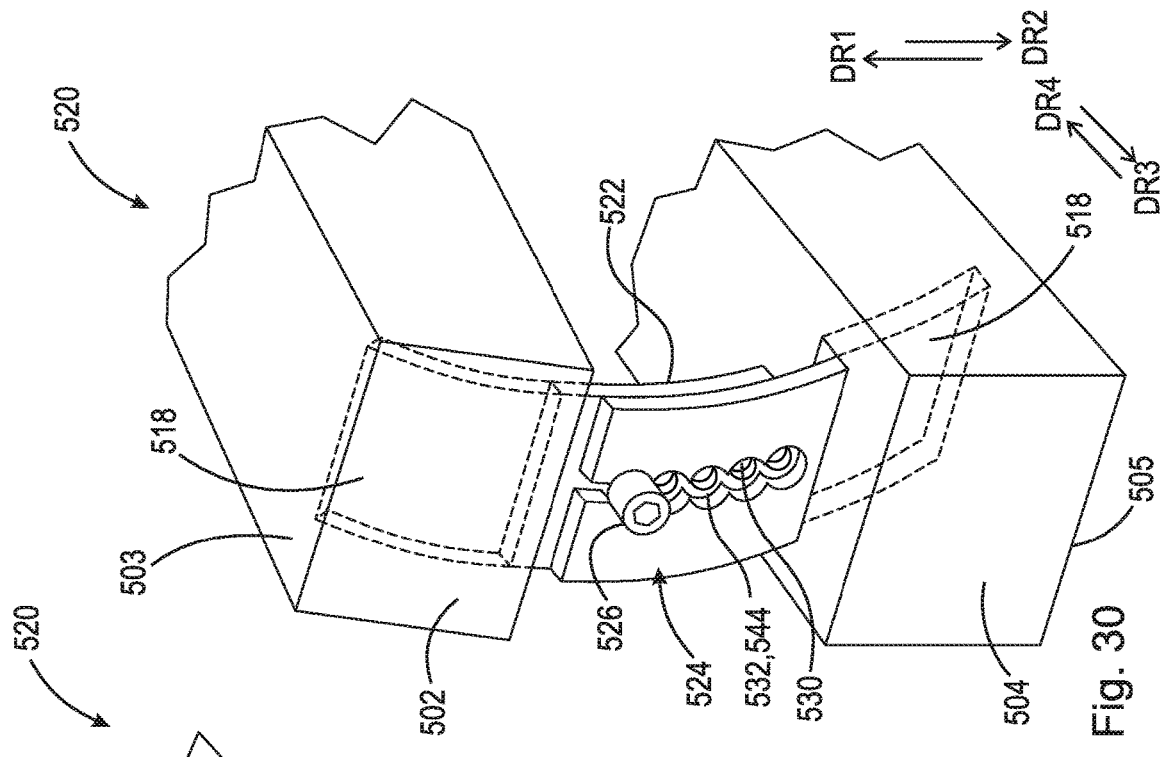
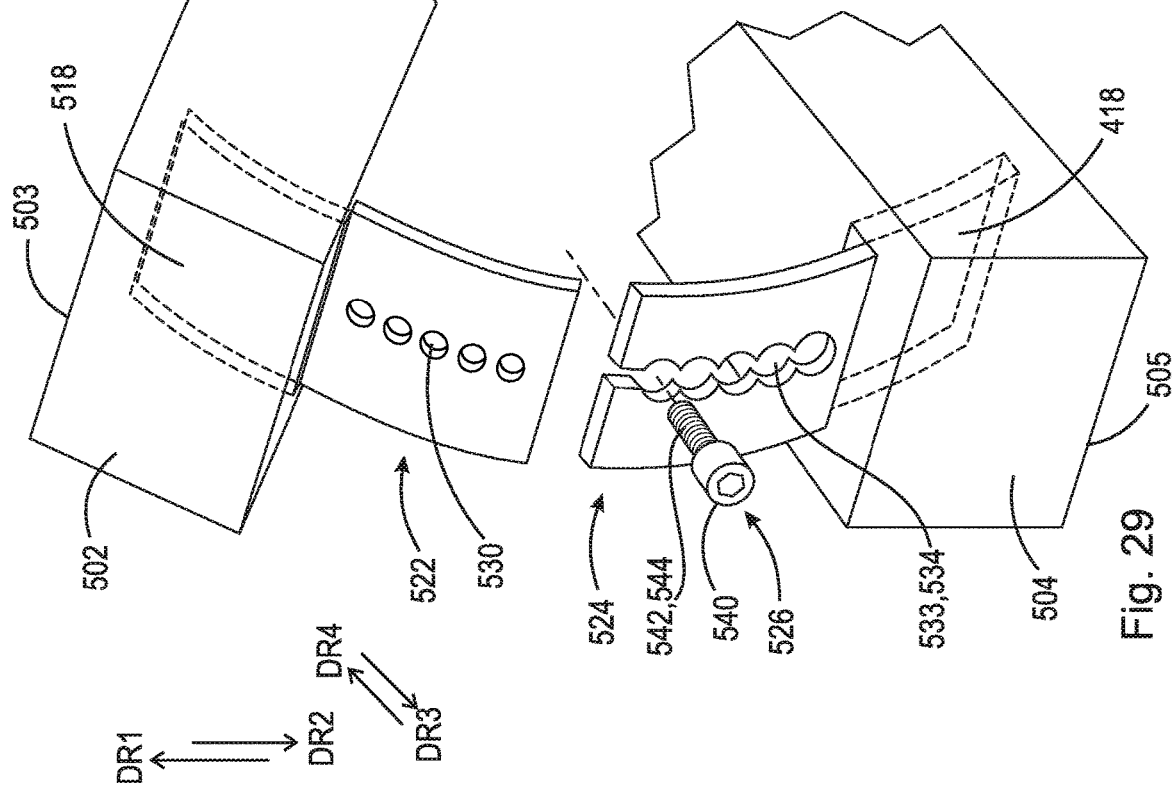

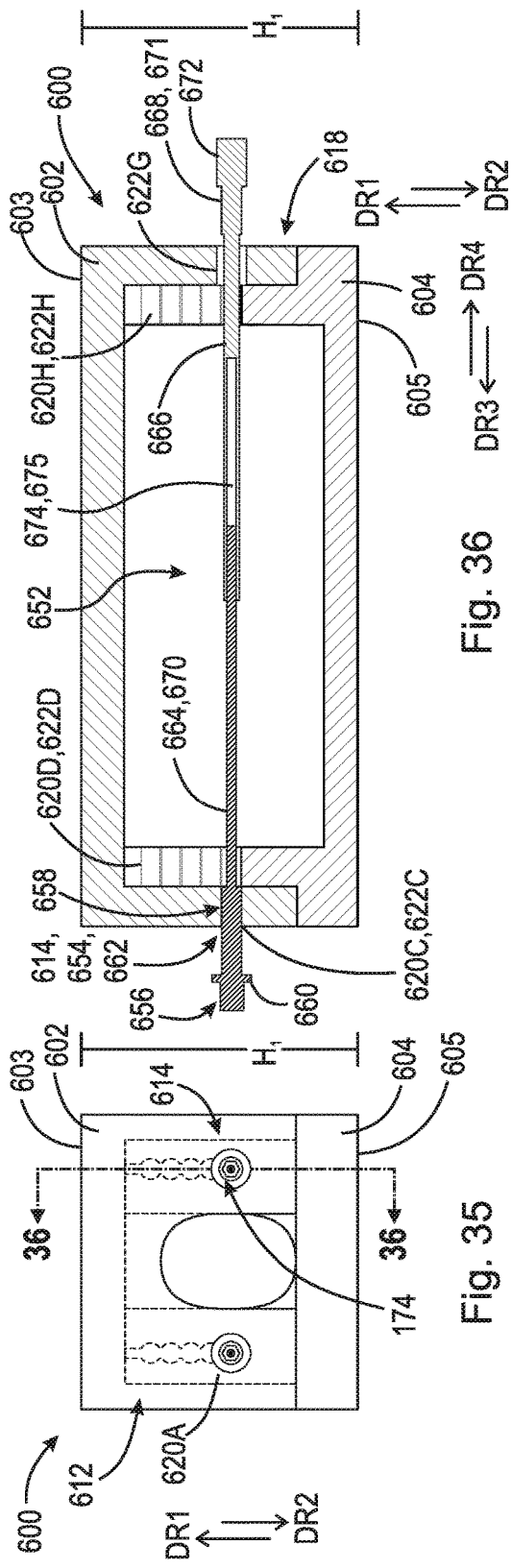
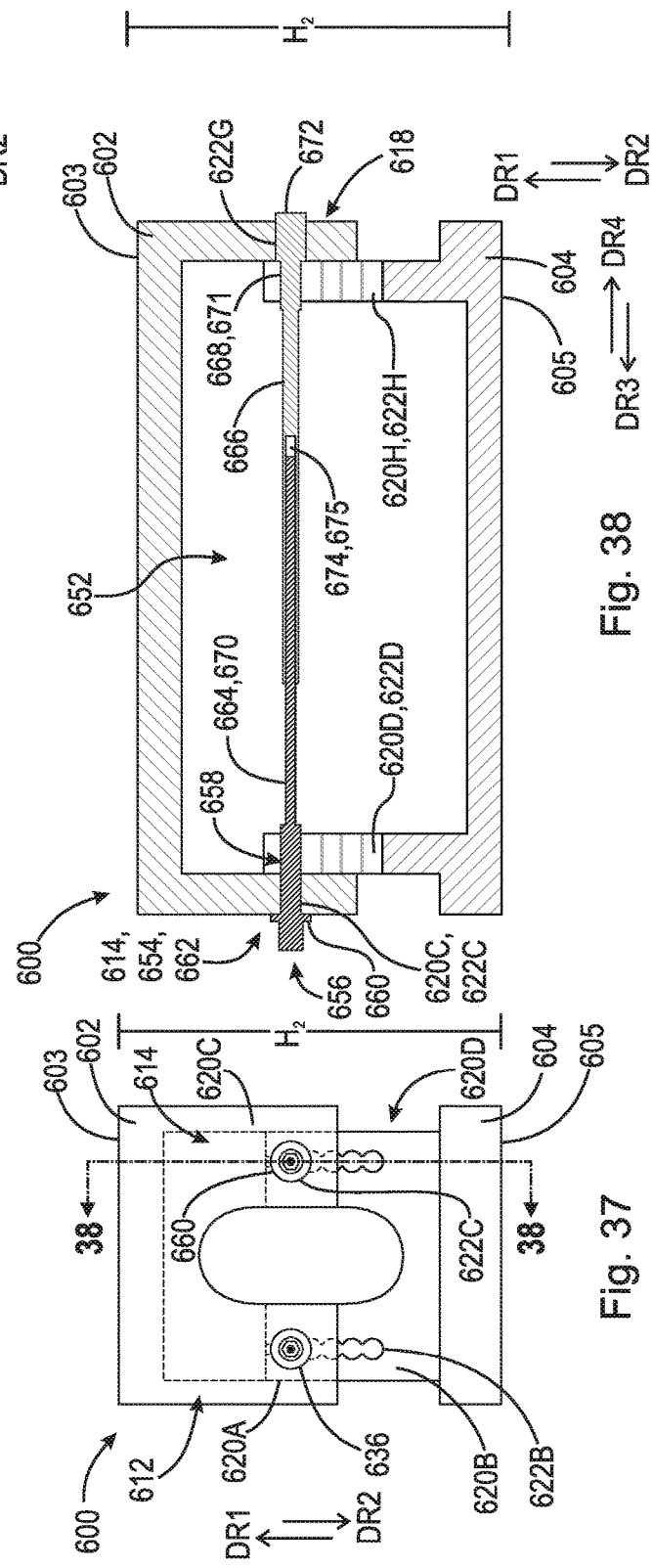

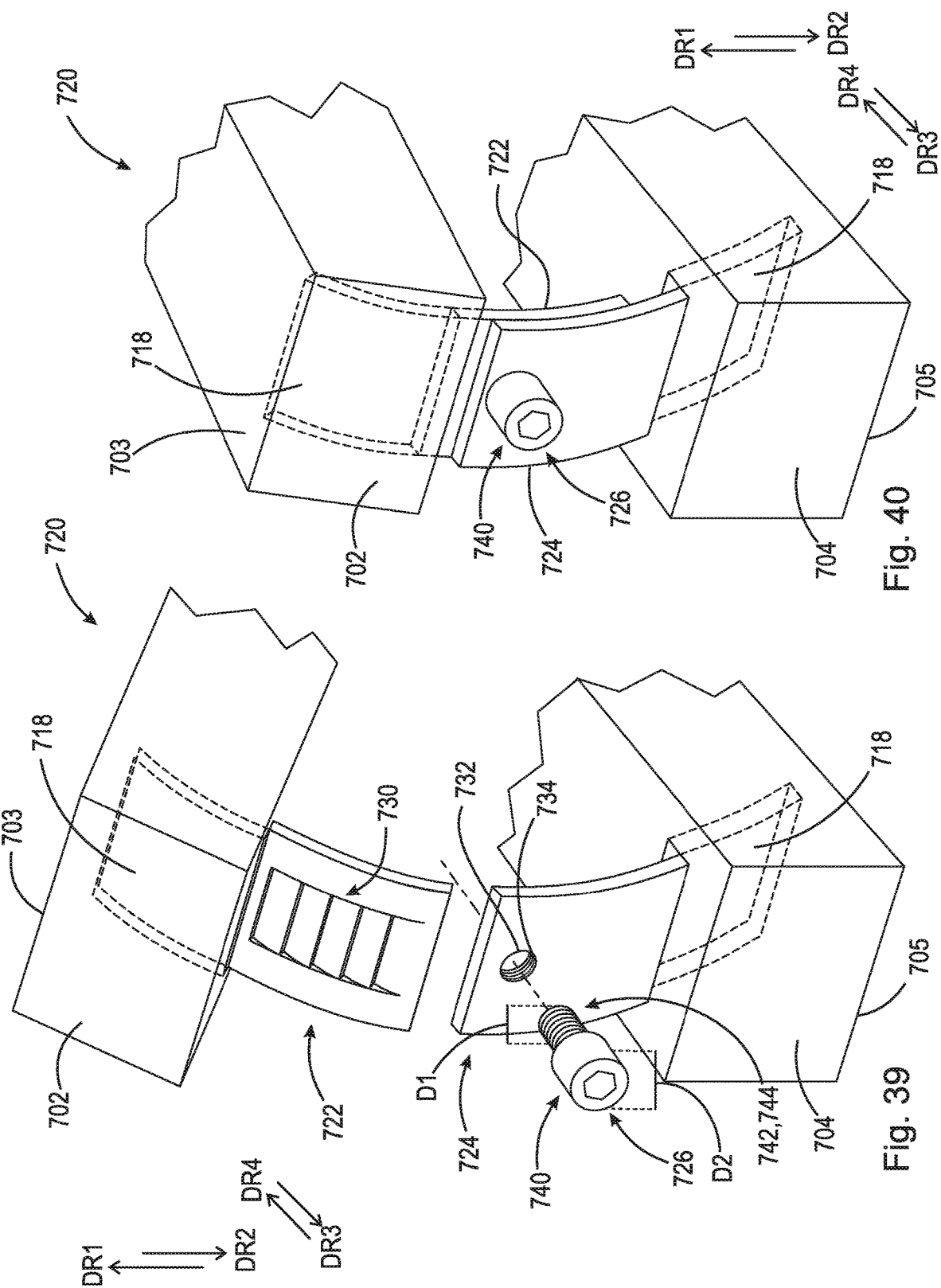

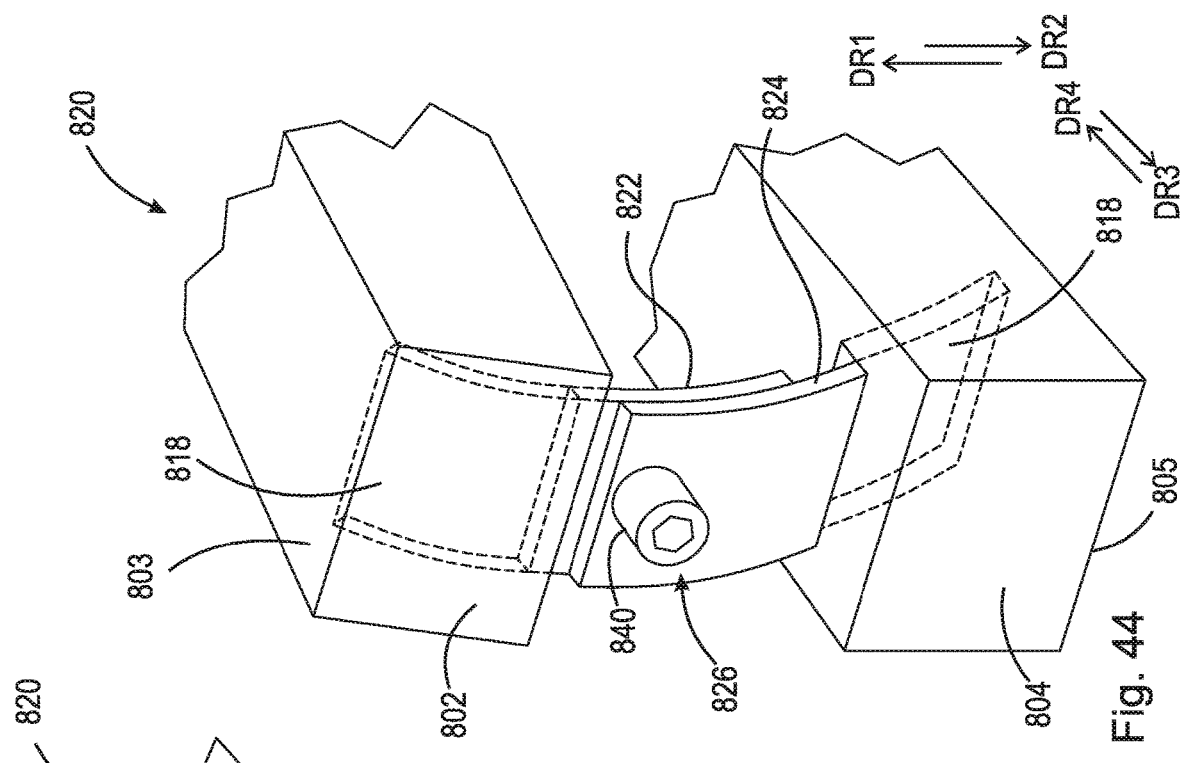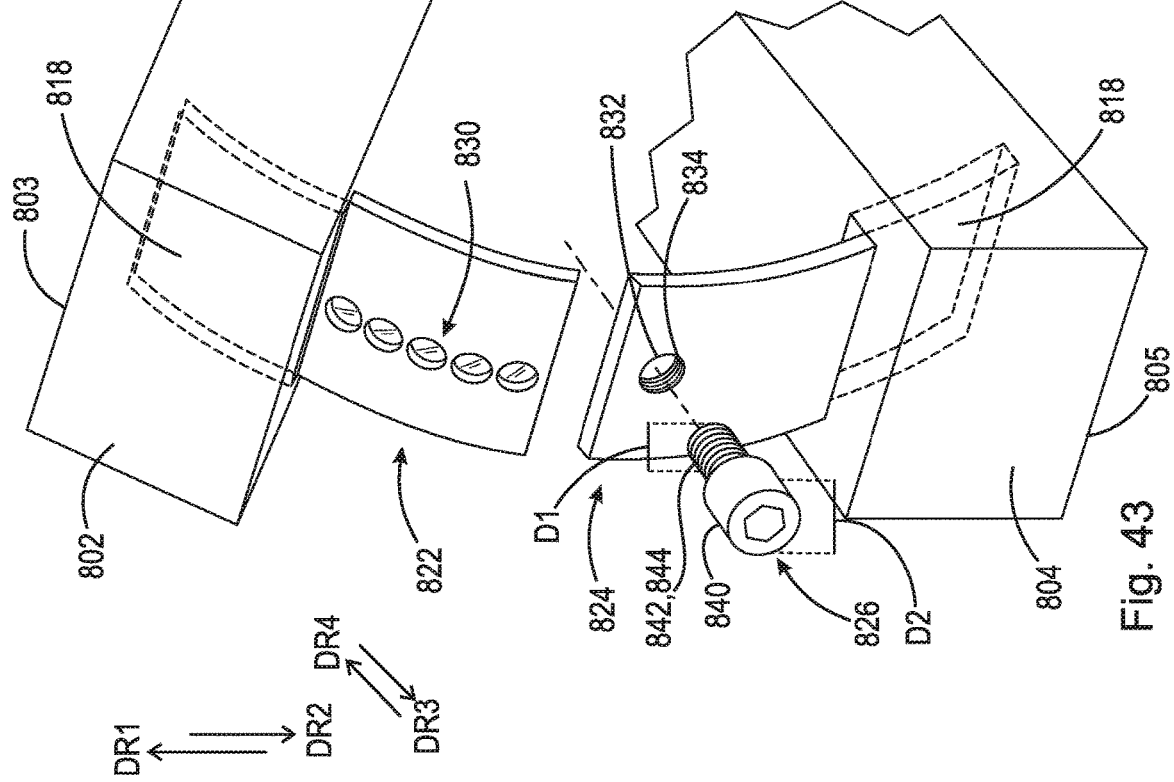

STAND-ALONE EXPANDABLE INTERBODY SPINAL FUSION DEVICE WITH LOCKING MECHANISM

CROSS-REFERENCE TO RELATED APPLICATIONS

This application is filed under 35 U.S.C. § 120 as a continuation-in-part of U.S. patent application Ser. No. 15/707,756, filed on Sep. 18, 2017, which application is hereby incorporated by reference in its entirety.

FIELD

The disclosure relates to spinal surgery, more particularly to intervertebral prosthesis, and, even more specifically, to a stand-alone expandable interbody spinal fusion device with a locking mechanism.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae (C1-C7) form the neck, support the head and neck, and allow nodding and shaking of the head. The thoracic vertebrae (T1-T12) join with the ribs to form the rib cage. The five lumbar vertebrae (L1-L5) carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information superhighway between the brain and the body. The nerves in the spinal cord branch off to form pairs of nerve roots that travel through the small openings between the vertebrae and the intervertebral foramens.

The repetitive forces which act on these intervertebral discs during repetitive day-to-day activities of bending, lifting and twisting cause them to break down or degenerate over time. Overt trauma or covert trauma occurring in the course of repetitive activities disproportionately affect the more highly mobile areas of the spine. Disruption of a disc's internal architecture leads to bulging, herniation or protrusion of pieces of the disc and eventual disc space collapse. Resulting mechanical and chemical irritation of surrounding neural elements cause pain, attended by varying degrees of disability. In addition, loss of disc space height relaxes tension on the longitudinal ligaments, thereby contributing to varying degrees of spinal instability such as spinal curvature.

Neural irritation and instability resulting from severe disc damage has been treated by removing the damaged disc and fusing adjacent vertebral elements. Removal of the disc relieves the mechanical and chemical irritation of neural elements, while osseous union solves the problem of instability. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, but with vertebra L3 in place atop disc $D_{L3-L4}$.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union.

Intervertebral prosthesis in various forms have therefore been used to provide immediate stability and to protect and preserve an environment that fosters growth of grafted bone such that a structurally significant bony fusion can occur.

After insertion, and shortly after the conclusion of the surgical process, these interbody devices experience the full weight of the patient's upper body, originally experienced by the disc prior to replacement. This weight may be sufficient to cause expandable intervertebral implants such as the implants disclosed in U.S. patent application Ser. No. 15/416,270 filed Jan. 26, 2017, which application is herein incorporated by reference in its entirety, to collapse from their expanded state to their unexpanded height, thereby negatively affecting the quality of bone fusion.

Thus, there is a long-felt need for a stand-alone expandable interbody spinal fusion device with a locking mechanism operatively arranged to prevent collapse of an interbody device after insertion.

SUMMARY

According to aspects illustrated herein, there is provided an expandable interbody spinal fusion device, comprising an inferior component including at least one hole, a superior component connected to the inferior component, the superior component including a plurality of catches operatively arranged to align with the at least one hole, and a locking screw operatively arranged to engage the plurality of catches and the at least one hole to lock the superior component with respect to the inferior component.

According to aspects illustrated herein, there is provided an expandable interbody spinal fusion device, comprising an inferior component including a first surface and at least one hole, a superior component hingedly connected to the inferior component, the superior component including a second surface and a plurality of catches operatively arranged to align with the at least one hole, a cavity formed between the inferior component and the superior component, and a locking screw operatively arranged to engage the plurality of catches and the at least one hole to lock the superior component with respect to the inferior component.

According to aspects illustrated herein, there is provided a stand-alone expandable interbody spinal fusion device including a superior component, an inferior component, an expansion mechanism operatively arranged to displace the superior component in a first direction relative to the inferior component about a first hinge, and a locking mechanism. The locking mechanism including a plate operatively arranged to pivot about a second hinge, the plate further comprising a first through-bore and a first plurality of teeth, a pawl operatively arranged to pivot about a third hinge, the pawl further comprising a second through-bore, and a post operatively arranged to pass through the second and third through-bores such that after the superior component is displaced in the first direction, the locking mechanism prevents displacement of the superior component in a second direction, opposite the first direction.

According to aspects illustrated herein, there is provided a stand-alone expandable interbody spinal fusion device including a superior component, an inferior component, an expansion mechanism operatively arranged to displace the superior component in a first direction relative to the inferior component about a hinge, and a locking mechanism. The locking mechanism including a first plate fixedly secured to the superior component, the first plate further comprising a first through-bore, a second plate fixedly secured to the inferior component, the second plate further comprising a second through-bore, a post having a first end and a second end such that after the superior component is displaced in the first direction, the locking mechanism prevents displacement of the superior component in a second direction, opposite the first direction.

According to aspects illustrated herein, there is provided a stand-alone expandable interbody spinal fusion device including a superior component, an inferior component, an expansion mechanism operatively arranged to displace the superior component in a first direction relative to the inferior component, and a locking mechanism. The locking mechanism including a first plate fixedly secured to the superior component, the first plate further comprising a first through-bore, a second plate fixedly secured to the inferior component, the second plate further comprising a second through-bore, a third plate fixedly secured to the superior component, the third plate further comprising a third through-bore, a fourth plate fixedly secured to the inferior component, the fourth plate further comprising a fourth through-bore, and, a post arranged to engage with the first through-bore, the second through-bore, the third through-bore, and the fourth through-bore, such that after the superior component is displaced in the first direction, the locking mechanism prevents displacement of the superior component in a second direction, opposite the first direction.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which:

FIG. 11 is a front view of a stand-alone expandable interbody spinal fusion device with a first embodiment of a locking mechanism, in an unexpanded state;

FIG. 12 is a cross-sectional view of a stand-alone expandable interbody spinal fusion device with a first embodiment of a locking mechanism, in an unexpanded state, taken generally along line 12-12 in FIG. 11;

FIG. 13 is a front view of a stand-alone expandable interbody spinal fusion device with a first embodiment of a locking mechanism, in an expanded state;

FIG. 14 is a cross-sectional view of a stand-alone expandable interbody spinal fusion device with a first embodiment of a locking mechanism, in an expanded state, taken generally along line 14-14 in FIG. 13;

FIG. 23 is a front perspective view of a stand-alone expandable interbody spinal fusion device with a third embodiment of a locking mechanism, in an unexpanded state;

FIG. 24 is a front perspective view of a stand-alone expandable interbody spinal fusion device with a third embodiment of a locking mechanism, in an expanded state;

FIG. 25 is a front perspective partial view of a fourth locking mechanism in an unlocked state;

FIG. 26 is a front perspective partial view of a fourth locking mechanism in a locked state;

FIG. 29 is a front perspective partial view of a fifth locking mechanism in an unlocked state;

FIG. 30 is a front perspective partial view of a fifth locking mechanism in a locked state;

FIG. 35 is a front view of a stand-alone expandable interbody spinal fusion device with a sixth embodiment of a locking mechanism, in an unexpanded state;

FIG. 36 is a cross-sectional view of a stand-alone expandable interbody spinal fusion device with a sixth embodiment of a locking mechanism, in an unexpanded state, taken generally along line 36-36 in FIG. 35;

FIG. 37 is a front view of a stand-alone expandable interbody spinal fusion device with a sixth embodiment of a locking mechanism, in an expanded state;

FIG. 38 is a cross-sectional view of a stand-alone expandable interbody spinal fusion device with a sixth embodiment of a locking mechanism, in an expanded state, taken generally along line 38-38 in FIG. 37;

FIG. 39 is a front perspective partial view of a seventh embodiment of a locking mechanism in an unlocked state;

FIG. 40 is a front perspective partial view of a seventh embodiment of a locking mechanism in a locked state;

FIG. 43 is a front perspective partial view of an eighth embodiment of a locking mechanism in an unlocked state;

FIG. 44 is a front perspective partial view of an eighth embodiment of a locking mechanism in a locked state;

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

The term "superior component" as used in the present disclosure is intended to mean the component of the body of the implant located in the highest position relative to the other components in first direction DR1.

The term "inferior component" as used in the present disclosure is intended to mean the component of the body of the implant located in the lowest position relative to the other components in first direction DR1.

The term "gear shaft" as used in the present disclosure is intended to mean any gear currently understood in the art that has been elongated such that it is substantially cylindrical in shape.

The term "pawl" as used in the present disclosure is intended to mean a plate or bar having one end arranged to engage the teeth of a ratchet and place pressure on the ratchet in a first direction such that the ratchet can only be disengaged from the teeth by motion in a second direction, opposite the first direction.

Figure 1:
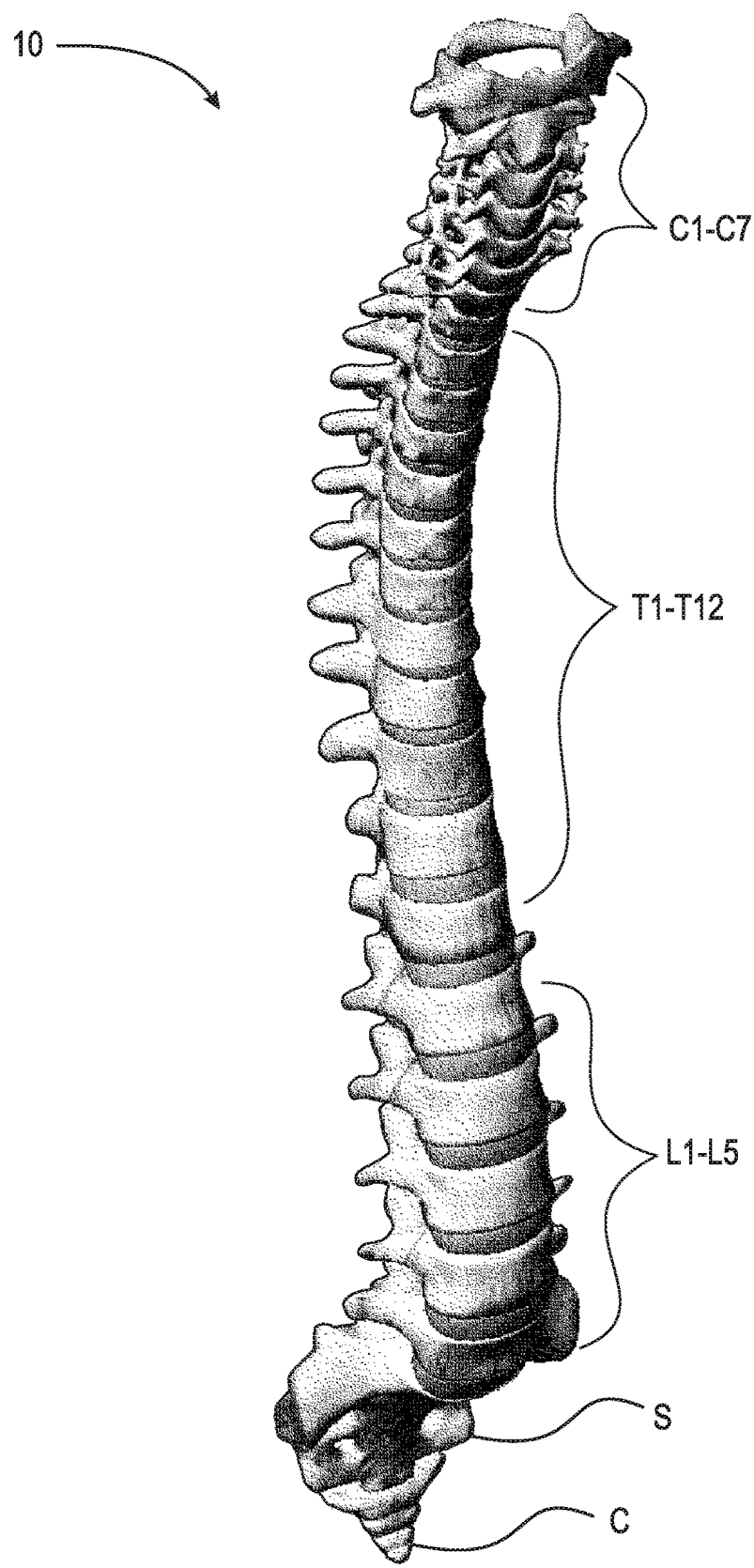
FIG. 1 is an anterior perspective view of spinal column 10.
Figure 2:
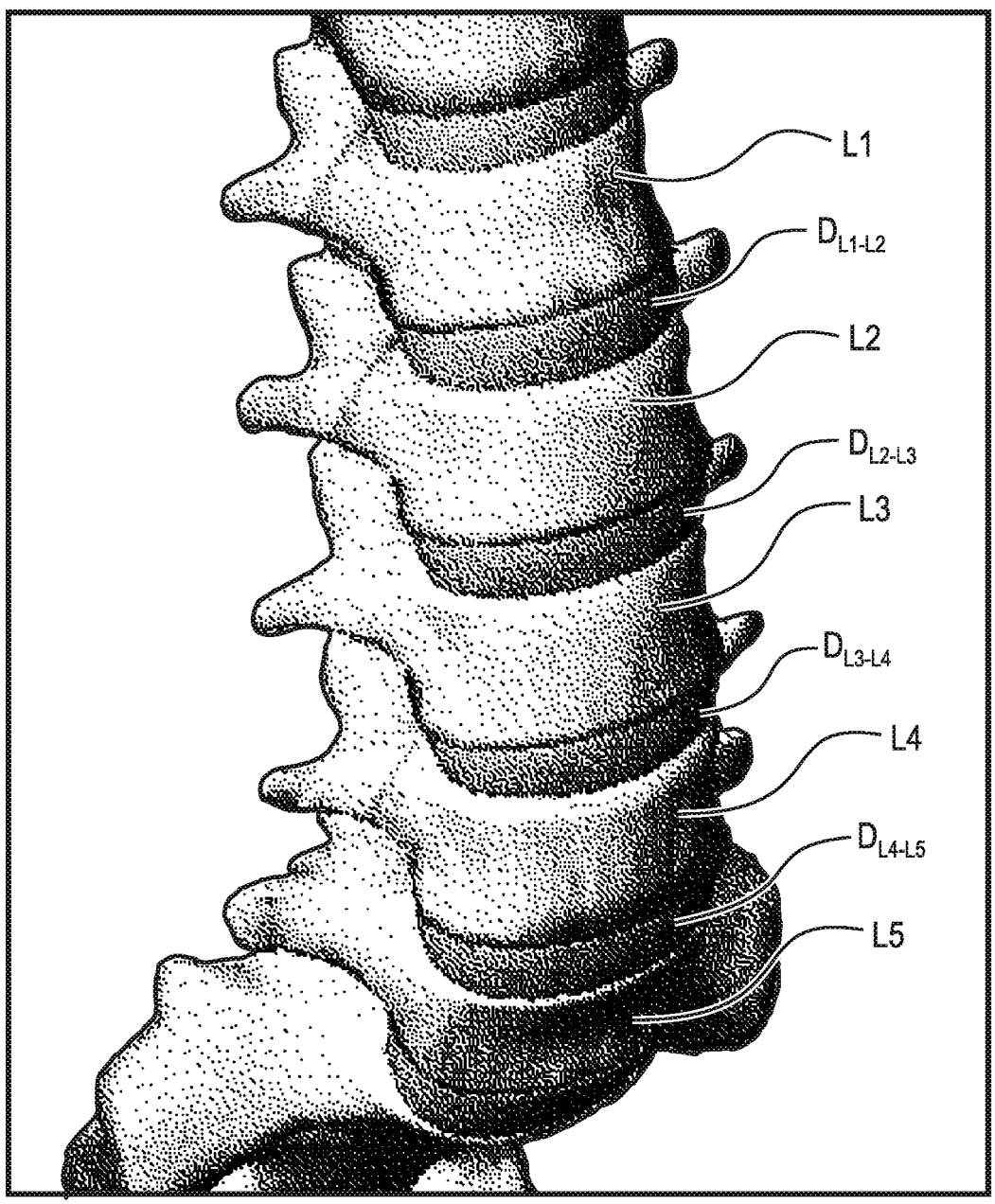
FIG. 2 is an anterior perspective view of the lumbar section of spinal column 10.
Figure 3:
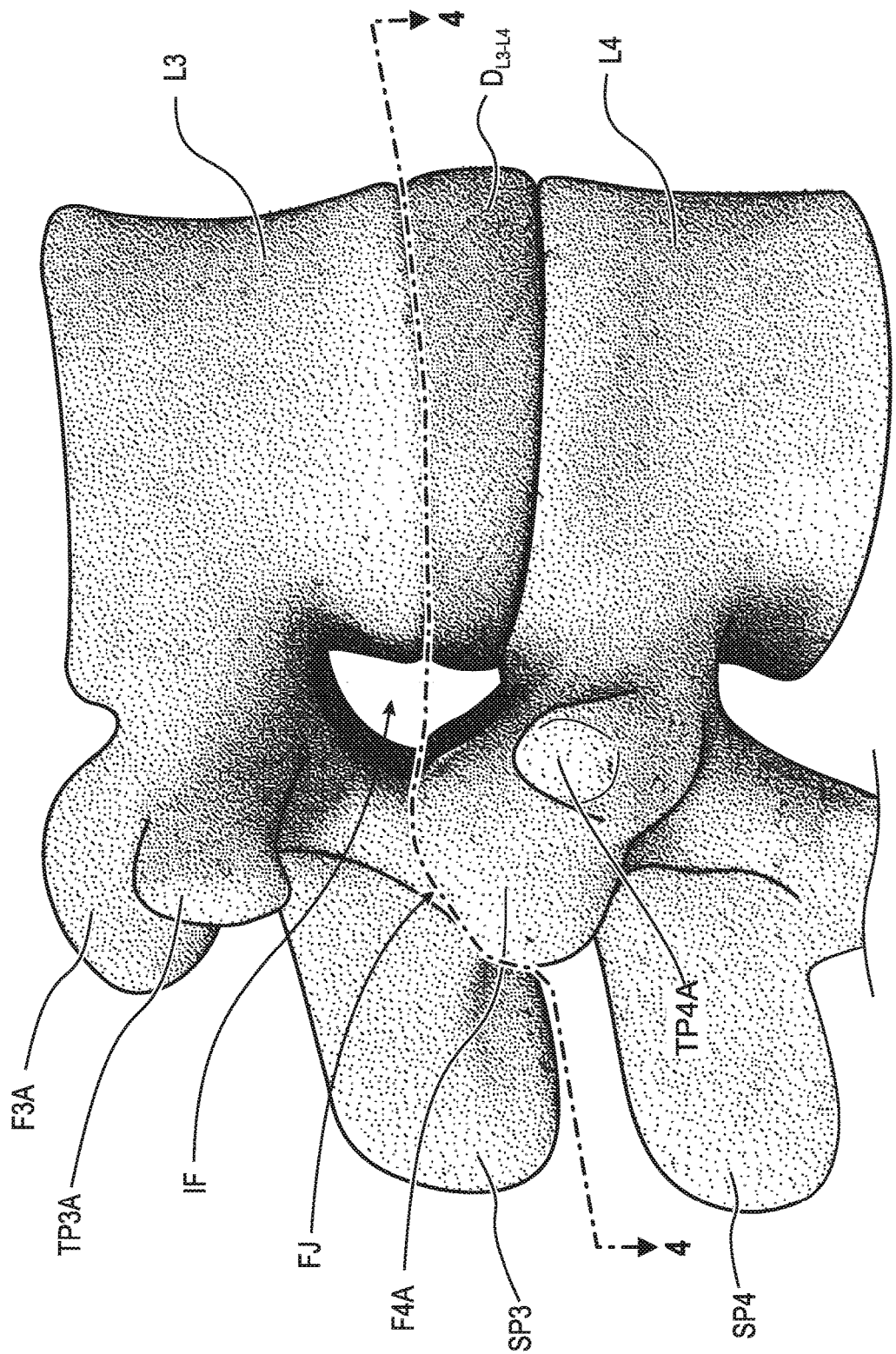
FIG. 3 is a lateral perspective view of L3, L4 vertebrae and disc $D_{L3\text{-}L4}$ and related spinal anatomy.
Figure 4:
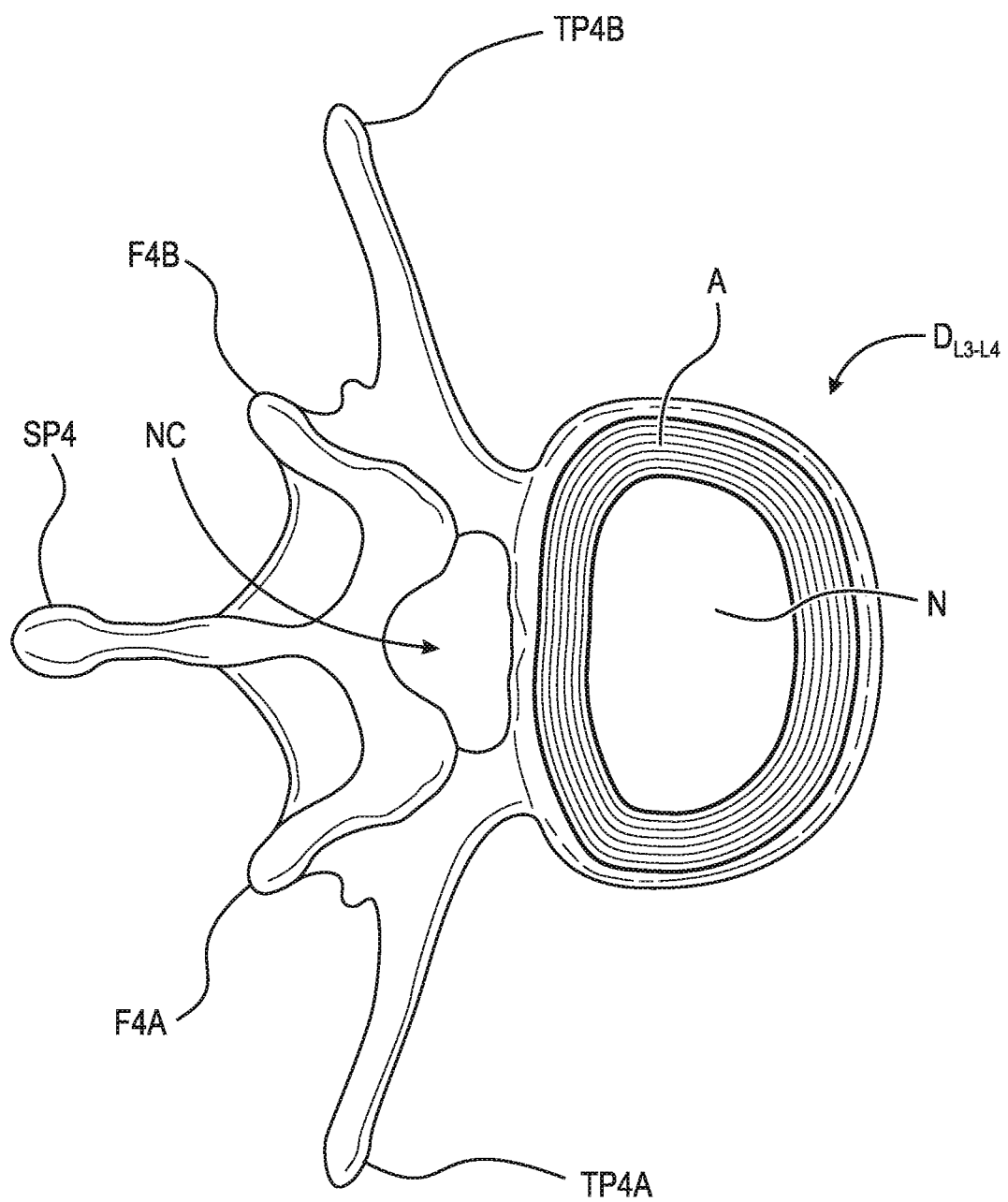
FIG. 4 is a top view of a section of the spinal column, taken generally along line 4-4 in FIG. 3.
Figure 5:
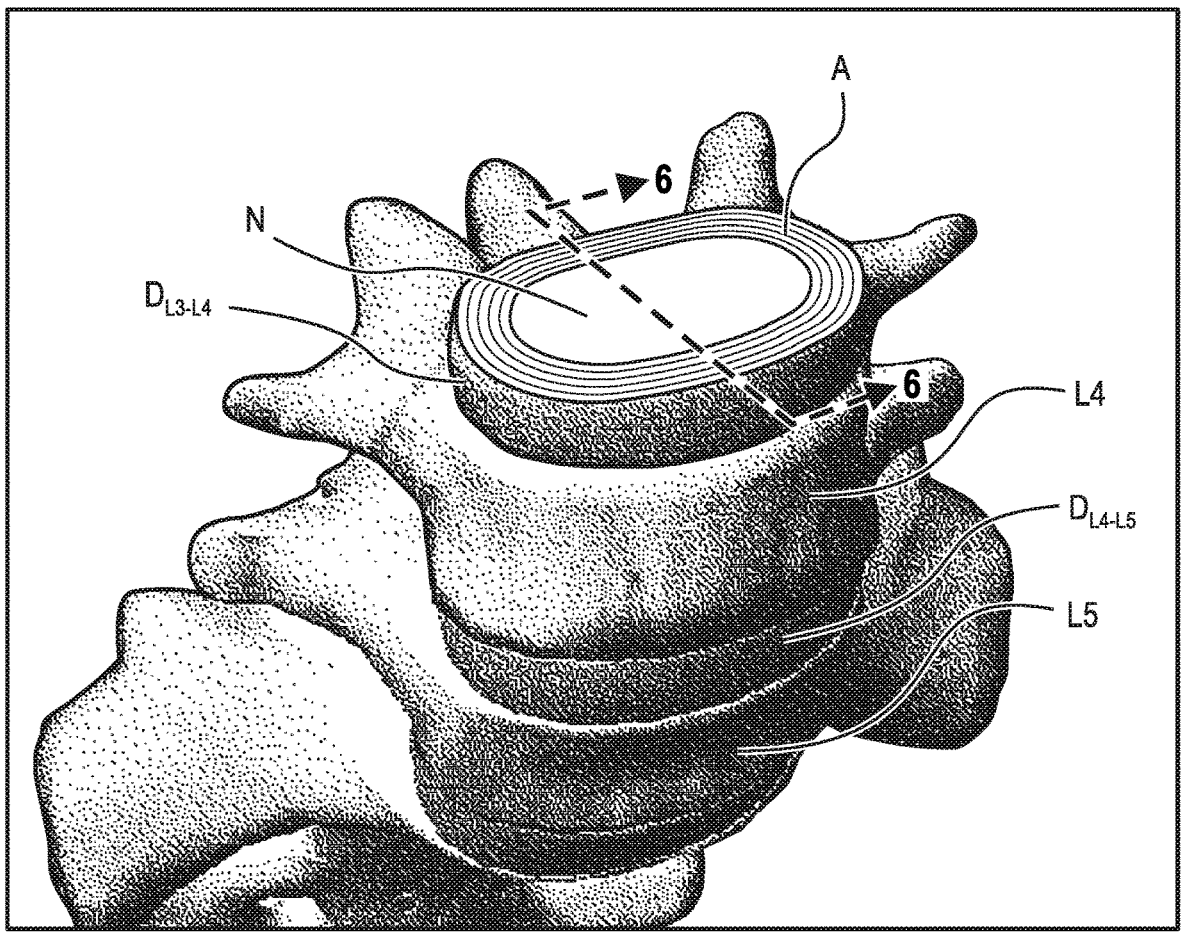
FIG. 5 is an enlarged anterior perspective view of the spinal column shown in FIG. 2, except with vertebra L3 and all other structure above L3 removed.
Figure 6:
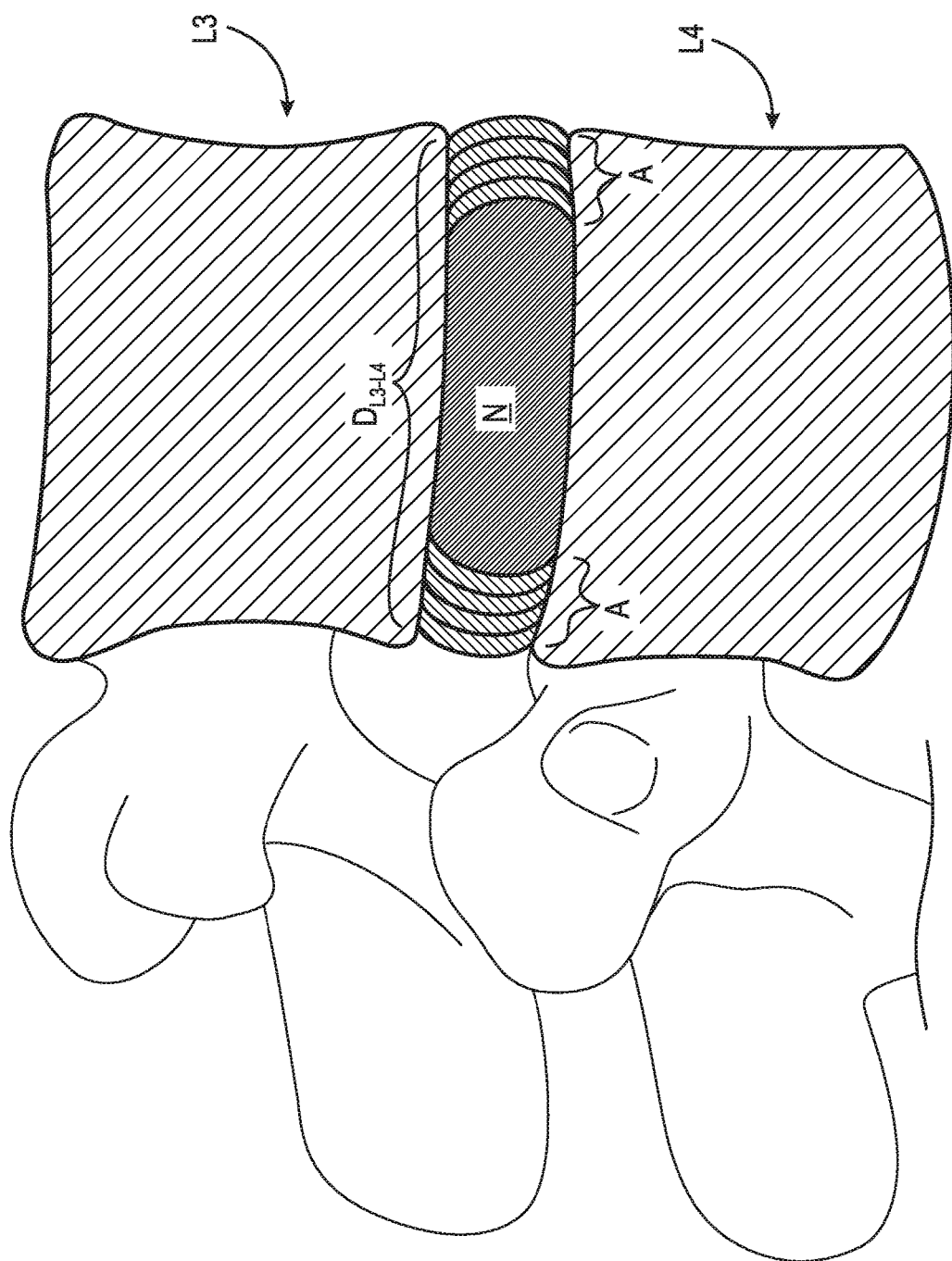
FIG. 6 is a partial cross-sectional view of the L4 vertebra and $D_{L3\text{-}L4}$ disc shown in FIG. 5, including L3 in cross-section.
Figure 7:
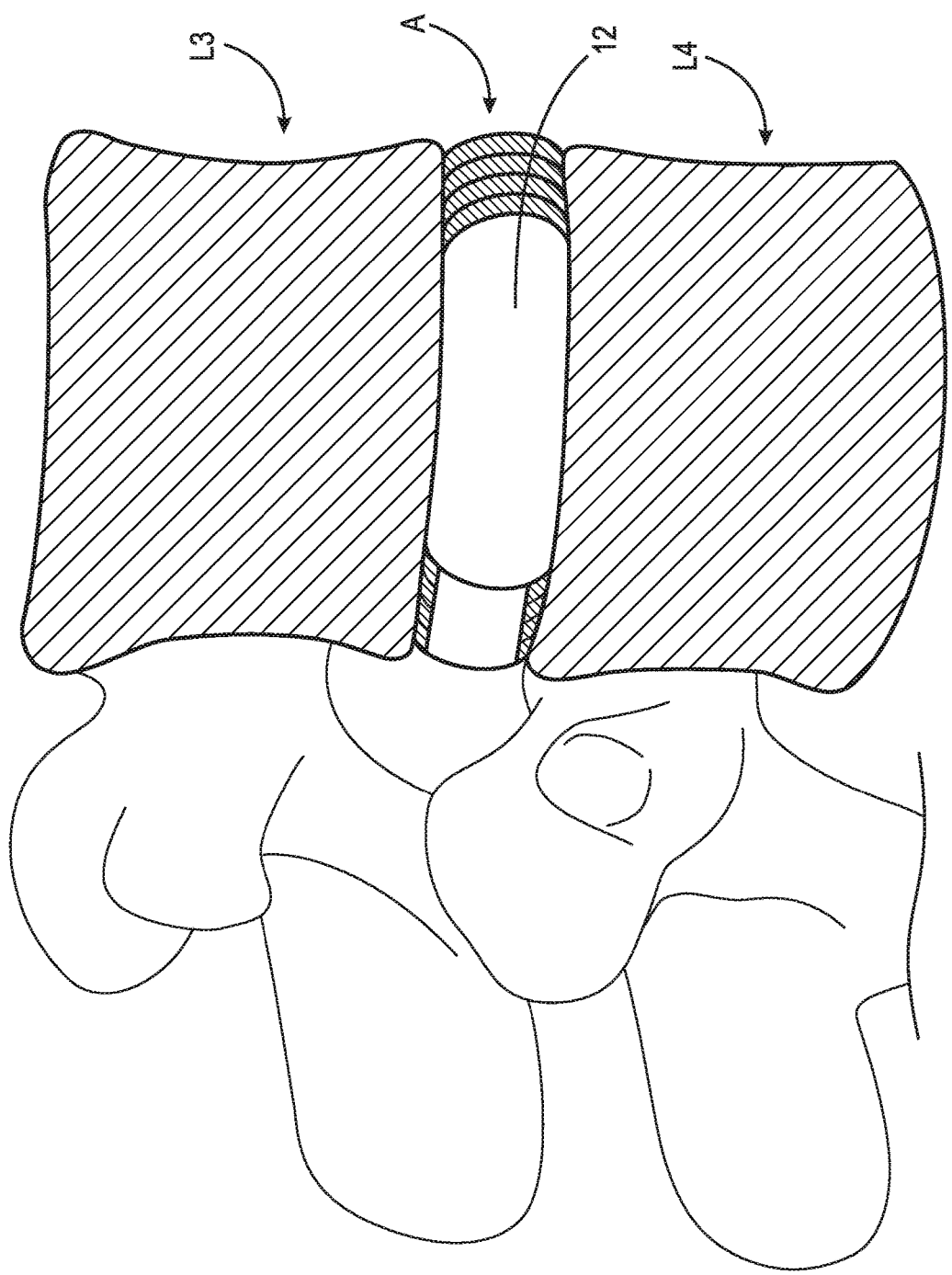
FIG. 7 is a partial cross-sectional view of the L4 vertebra and $D_{L3\text{-}L4}$ disc shown in FIG. 5, showing the removal of the disc nucleus post-discectomy including L3 in cross-section.

Adverting now to the Figures, and as described previously, FIGS. 1-6 depict various parts and sections of spinal anatomy. FIG. 7 illustrates a partial cross-sectional view of the L3 and L4 vertebra with disc $D_{L3-L4}$ removed (post discectomy) and able to receive stand-alone expandable interbody spinal fusion device 100.

Figure 8:
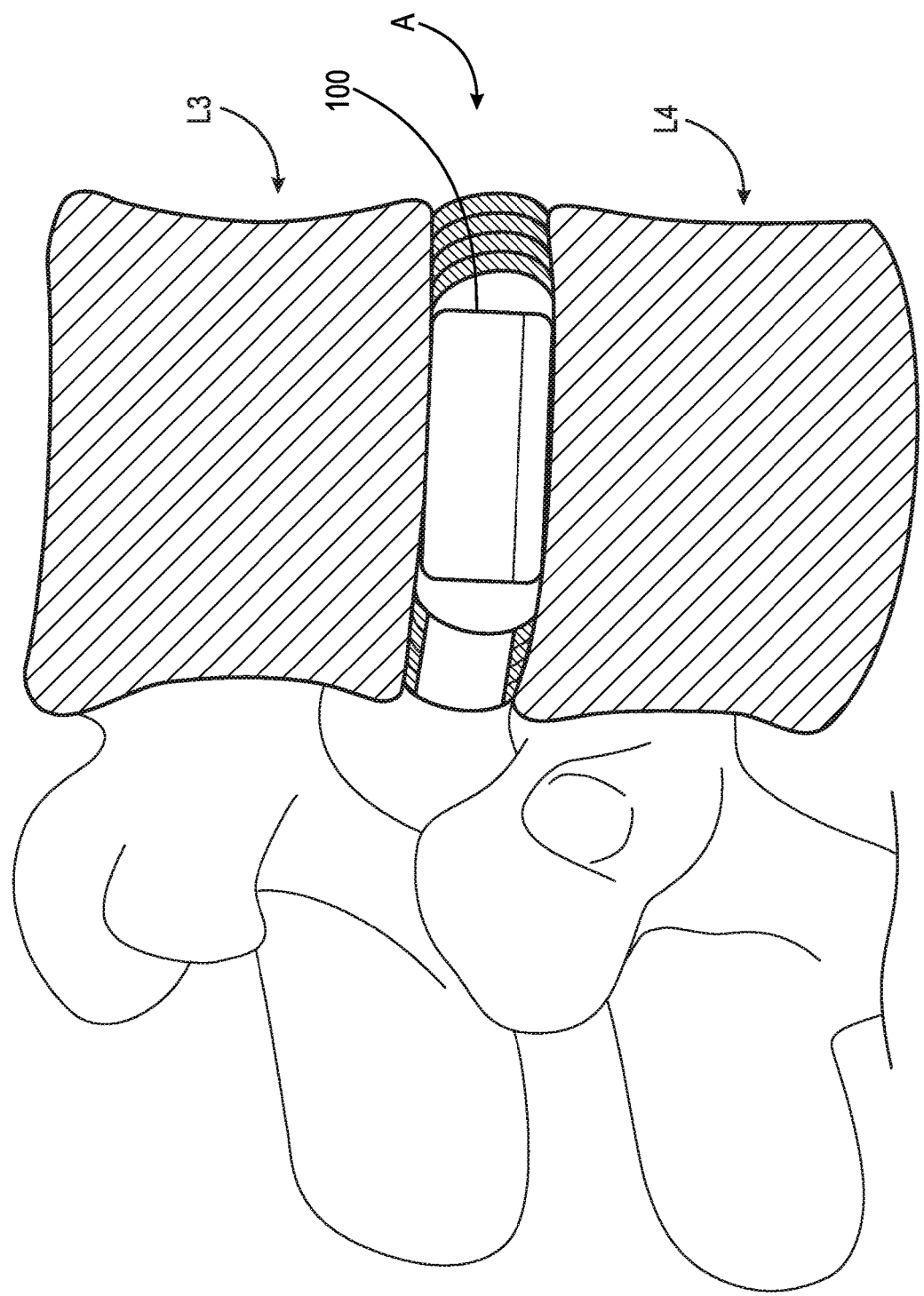
FIG. 8 illustrates the introduction of the stand-alone expandable interbody spinal fusion device into the disc space in an unexpanded state.

FIG. 8 illustrates a partial cross-sectional view of the L3 and L4 vertebra with stand-alone expandable interbody spinal fusion device 100 in place within disc space 12 in an unexpanded state.

Figure 9:
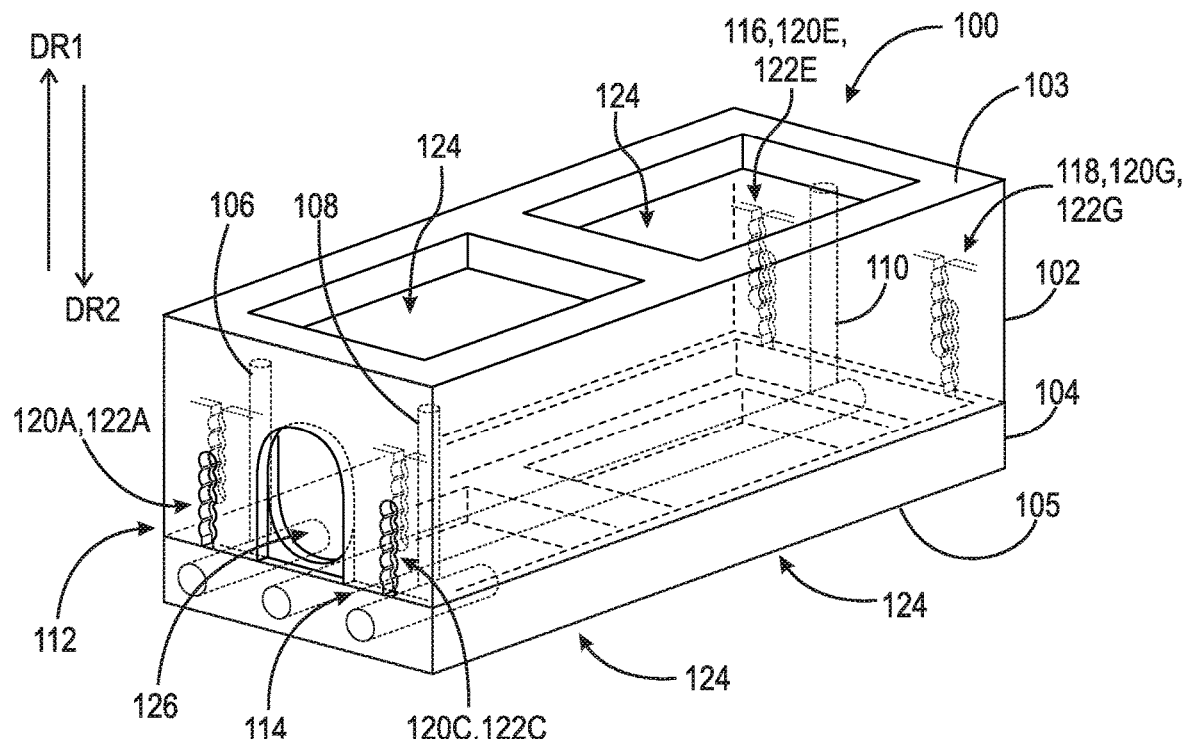
FIG. 9 is a perspective view of a first embodiment of a stand-alone expandable interbody spinal fusion device, in an unexpanded state.

FIG. 9 is a perspective view of stand-alone expandable interbody spinal fusion device 100, in an unexpanded state. Device 100 comprises superior component 102, inferior component 104, and expansion mechanisms 106, 108, and 110 (described infra) arranged to displace superior component 102 in a first direction DR1 relative to inferior component 104, giving device 100 an expanded height $H_2$ greater than unexpanded height $H_1$ (shown in FIGS. 11 and 13). Device 100 also comprises locking mechanisms 112, 114, 116, and 118 arranged between superior component 102 and inferior component 104 (locking mechanisms 116 and 118 are shown in FIG. 10).

Figure 10:
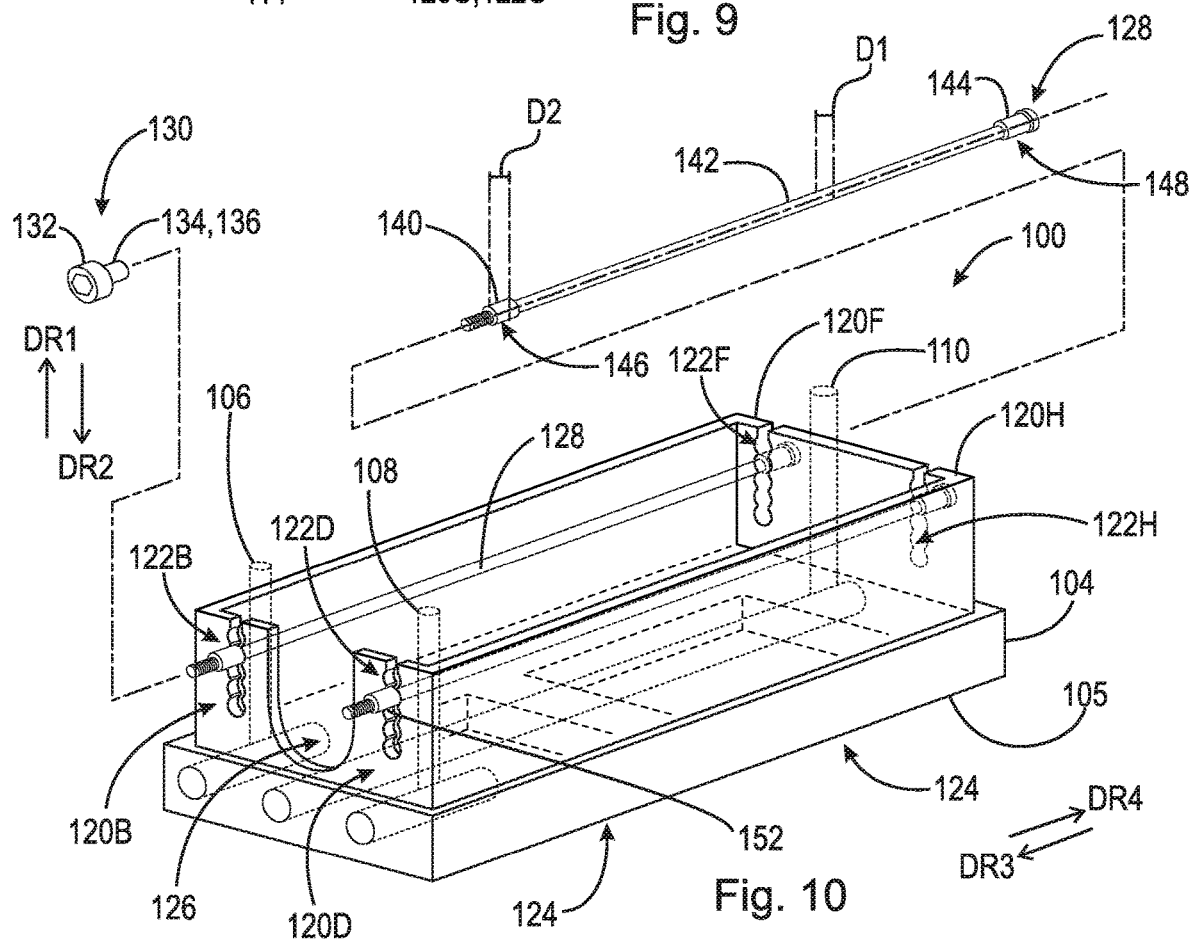
FIG. 10 is a partially-exploded perspective view of a stand-alone expandable interbody spinal fusion device with a first embodiment of a locking mechanism, in an expanded state.

Locking mechanism 112 comprises plates 120A (shown in FIG. 9) and 120B (shown in FIG. 10). Locking mechanism 114 comprises plates 120C (shown in FIG. 9) and 120D (shown in FIG. 10). Locking mechanism 116 comprises plates 120E (shown in FIG. 9) and 120F (shown in FIG. 10). Locking mechanism 118 comprises plates 120G (shown in FIG. 9) and 120H (shown in FIG. 10). Each of plates 120A-120H further include a plurality of through-bores, i.e., plurality of through-bores 122A-122H, respectively. It should be appreciated that, although plates 120A-120H are shown as integral within superior component 102 and inferior component 104, plates 120A-120H could also be discrete plates, fixedly secured to superior component 102 and inferior component 104.

Superior component 102 and inferior component 104 further comprise at least one first aperture 124 arranged to allow fusion between bone fusing material and the adjacent vertebra and a second aperture 126 located on the front face of device 100 and arranged to allow the introduction of bone fusing material into device 100. Second aperture 126 is illustrated as an arched slot as a non-limiting example, however, it should be appreciated that second aperture 126 could be an aperture of any suitable shape, e.g., triangular, circular, rectangular, elliptical, etc., that would allow for the introduction of bone fusing material into device 100. Superior component 102 has a first surface 103 and inferior component 104 has a first surface 105.

FIG. 10 is a perspective view of stand-alone expandable interbody spinal fusion device 100, in an expanded state. It should be appreciated that FIG. 10 is a partial view, i.e., superior component 102 has been removed for clarity.

During surgery and after device 100 is implanted in disc space 12, a surgeon can apply torque to expansion mechanisms 106, 108, and 110 via any device that imparts rotational force upon expansion mechanisms 106, 108, and 110 (e.g., a screw driver or impact driver). Expansion mechanisms 106, 108 and 110 are preferably the embodiment illustrated in FIGS. 15 and 16, described infra. Furthermore, it should be appreciated that although expansion mechanisms 106, 108, and 110 are depicted within inferior component 104 in FIGS. 9-14, expansion mechanisms 106, 108, and 110 could be arranged within superior component 102. This rotational force causes expansion mechanisms 106, 108, and 110, to displace superior component 102 in direction DR1 relative to inferior component 104 giving device 100 an expanded height $H_2$, greater than $H_1$ (shown in FIGS. 11 and 13). It should be appreciated that expansion mechanisms 106, 108, and 110 can be expanded to any height between unexpanded height $H_1$ and expanded height $H_2$. Device 100 further comprises post 128 and fastener 130. Post 128 and fastener 130 are provided to secure locking mechanisms 112 and 116 in position once device 100 is expanded to its final height. Fastener 130 has a first end 132 and a second end 134. First end 132 is operatively arranged to engage with any device known in the art that can impart rotational motion onto fastener 130, e.g., a drill. Second end 134 includes female threading 136. Post 128 further includes four sections, i.e., section 138, section 140, section 142, and section 144. Section 138 comprises male threading 146 operatively arranged to engage with female threading 136. Section 144 comprises stopping element 148. It should be appreciated that, although stopping element 148 is depicted as a flanged member, other variations of stopping elements can be used, e.g., a spherical stopping element. Sections 138 and 142 have diameter D1 and sections 140 and 144 have diameter D2, where D2 is greater than D1. Prior to locking, sections 138 and 142 having diameter D1 are loosely seated in longitudinal space 150 (shown in FIG. 11) arranged between each through-bore in the plurality of through-bores 122A, 122B, 122E, and 122F. After device 100 has been inserted into disc space 12 and expanded to an appropriate height, a surgeon can apply torque to first end 132 of fastener 130, pulling post 128 in direction DR3 into the locked position. In the locked position, sections 140 and 144 are completely seated in one of the through-bores of plurality of through-bores 122A, 122B, 122E, and 122F, which correspond to the chosen device height. In this locked position, device 100 is prevented from collapsing in direction DR2.

Device 100 further comprises post 152 and fastener 154 (shown in FIG. 14). Post 152 and fastener 154 are provided to secure locking mechanisms 114 and 118 in position once device 100 is expanded to its final height. Fastener 154 has a first end 156 and a second end 158. First end 156 includes a recess operatively arranged to engage with any device known in the art that can impart rotational motion onto fastener 154, e.g., a drill. Second end 158 includes female threading 160. Post 152 includes four sections, i.e., section 162, section 164, section 166, and section 168. Section 162 comprises male threading 170 operatively arranged to engage with female threading 160 of fastener 154. Section 168 comprises stopping element 172. It should be appreciated that, although stopping element 172 is depicted as a flanged member, other variations of stopping elements can be used, e.g., a spherical stopping element. Sections 162 and 166 have diameter D1 and sections 164 and 168 have diameter D2 where D2 is greater than D1. Prior to locking, sections 162 and 166, having diameter D1, are loosely seated in longitudinal space 174 (shown in FIG. 11) arranged between each through-bore in the plurality of through-bores 122C, 122D, 122G, and 122H. After device 100 has been inserted into disc space 12 and expanded to an appropriate height, a surgeon can apply torque to first end 156 of fastener 154, pulling post 152 in direction DR3 into the locked position. In the locked position, sections 164 and 168 are seated in one of the through-bores of plurality of through-bores 122C, 122D, 122G, and 122H, which corresponds to the chosen device height. In this locked position, device 100 is prevented from collapsing in direction DR2.

FIG. 11 is a front view of stand-alone expandable interbody spinal fusion device 100, in an unexpanded state having an unexpanded height $H_1$. FIG. 12 is a cross-sectional view of stand-alone expandable interbody spinal fusion device 100, in an unexpanded state having an unexpanded height $H_1$. FIG. 13 is a front view stand-alone expandable interbody spinal fusion device 100, in an expanded state having an expanded height $H_2$, greater than $H_1$. FIG. 14 is a cross-sectional view of stand-alone expandable interbody spinal fusion device 100 in an expanded state having an expanded height $H_2$, greater than $H_1$. It should be appreciated that in FIGS. 12 and 14, expansion mechanisms 106, 108 and 110 have been removed for clarity. It should also be appreciated that, although pluralities of through-bores 122A-122H are illustrated with a longitudinal space between each through-bore of each plurality of through-bores, it is also contemplated that plurality of through-bores 122A-122H could include multiple discrete through-bores, separate and distinct from each other with no longitudinal space between them.

Figures 15A, 15B:
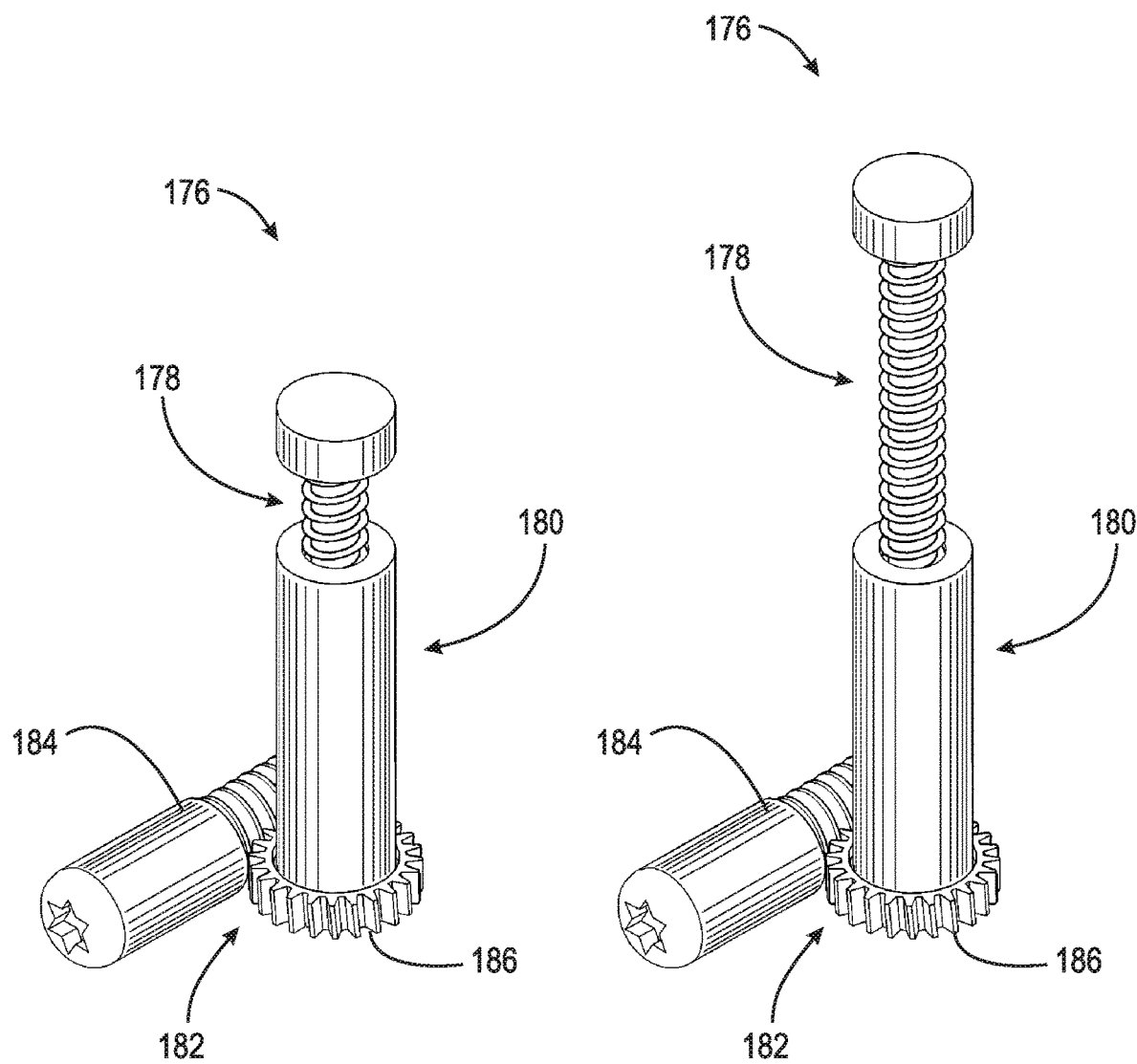
FIG. 15A is a perspective view of an expansion mechanism in an unexpanded state.
FIG. 15B is a perspective view an expansion mechanism in an expanded state.

FIG. 15A is a perspective view of expansion mechanism 176 in an unexpanded state. FIG. 15B is a perspective view of an expansion mechanism 176 in an expanded state. Expansion mechanism 176 comprises threaded rod 178, threaded sleeve 180, and worm drive 182 having worm 184 and gear 186. A portion of threaded rod 178 can be embedded within superior component 102 such that it is rotationally fixed; however, it should be appreciated that the frictional engagement between the top surface of threaded rod 178 and the inner surface of superior component 102 may be sufficient to prevent threaded rod 178 from freely rotating. During surgery and after device 100 is implanted in disc space 12, a surgeon can apply torque to worm drive 182 via any device that imparts rotational force upon worm 184 (e.g., a screw driver or impact driver). Torque is transferred 90 degrees through worm drive 182, via worm 184 and gear 186. Rotation of gear 186 causes threaded sleeve 180 to rotate. As threaded sleeve 180 rotates, threaded rod 178 remains rotationally locked due to the portion embedded within superior component 102, or frictional contact with the inner surface of superior component 102. As threaded sleeve 180 rotates, the threads of the rotationally locked threaded rod 178 ride upward along the threads within threaded sleeve 180, displacing threaded rod 178, and subsequently superior component 102, in direction DR1. Threaded rod 178 includes a stopping feature to prevent threaded rod 178 from being ejected from threaded sleeve 180. For example, the lower portion of threaded rod 178 could be threadless (not shown in the figures), and therefore prevent threaded rod 178 from being ejected from threaded sleeve 180. When threaded rod 178 reaches its maximum expansion, the unthreaded portion of threaded rod 178 remains within threaded sleeve 180, preventing threaded rod 178 from being pushed out of threaded sleeve 180. Alternatively, the stopping feature could be a flange on the recessed portion of threaded rod 178 arranged to engage with a retention shoulder (not shown in the figures) within threaded sleeve 180 in a fully expanded state. It should be appreciated that worm drive 182 could be arranged to transfer torque in other arrangements, i.e., 180 degrees, 270 degrees, or any desirable angle required by the arrangement of worm 184 and gear 186. It should further be appreciated that although a gear 186 is depicted in the figures as a spur gear, other suitable gears may be selected, i.e., a bevel gear, a hypoid gear, a spiral gear, or a face gear.

Figure 16:
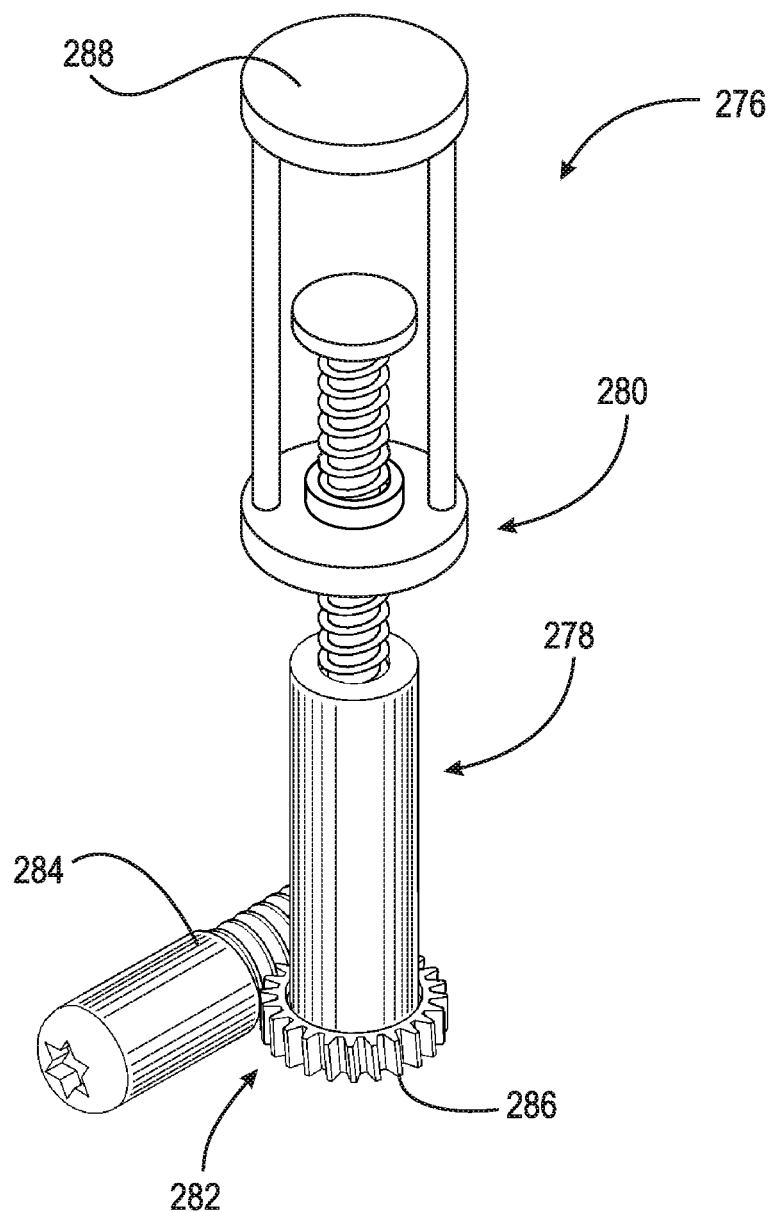
FIG. 16 is a perspective view of an expansion mechanism.

FIG. 16 is a perspective view of expansion mechanism 276. Expansion mechanism 276 comprises threaded rod 278, lifting nut 280, and worm drive 282 having worm 284 and gear 286. Lifting nut 280 may be connected to superior component 102. In some embodiments, lifting nut 280 comprises platform 288 connected thereto, wherein the platform 288 is connected to superior component 102 such that lifting nut 280 is rotationally fixed. Lifting nut 280 may be fixedly secured to superior component 102; however, it should be appreciated that the frictional engagement between platform 288 and the inner surface of superior component 102 may be sufficient to prevent lifting nut 280 from freely rotating. During surgery and after device 100 is implanted in disc space 12, a surgeon can apply torque to worm drive 282 via any device that imparts rotational force upon worm 284 (e.g., a screw driver or impact driver). Torque is transferred 90 degrees through worm drive 282, via worm 284 and gear 126. Rotation of gear 286 causes threaded rod 278 to rotate. Threaded rod 278 is non-rotatably connected to gear 286. As threaded rod 278 rotates, lifting nut 280 remains rotationally locked due to platform 288 being embedded within superior component 102, or frictional contact with the inner surface of superior component 102. As threaded rod 278 rotates, the threads of the rotationally locked lifting nut 280 ride upward along the threads on threaded rod 278, displacing lifting nut 280, and subsequently superior component 102, in direction DR1. Threaded rod 278 may include a stopping feature to prevent lifting nut 280 from being ejected from threaded rod 280. For example, the top portion of threaded rod 278 could be threadless (not shown in the figures), and therefore prevent lifting nut 280 from being ejected from threaded rod 278. When lifting nut 280 reaches its maximum expansion, the unthreaded portion of threaded rod 278 remains within lifting nut 280, preventing lifting nut 280 from being pushed off of threaded rod 278. Alternatively, the stopping feature could be a flange on the end of threaded rod 278 arranged to engage with lifting nut 280, as shown. It should be appreciated that worm drive 282 could be arranged to transfer torque in other arrangements, i.e., 180 degrees, 270 degrees, or any desirable angle required by the arrangement of worm 184 and gear 186. It should further be appreciated that although a gear 186 is depicted in the figures as a spur gear, other suitable gears may be selected, i.e., a bevel gear, a hypoid gear, a spiral gear, or a face gear.

Figure 17:
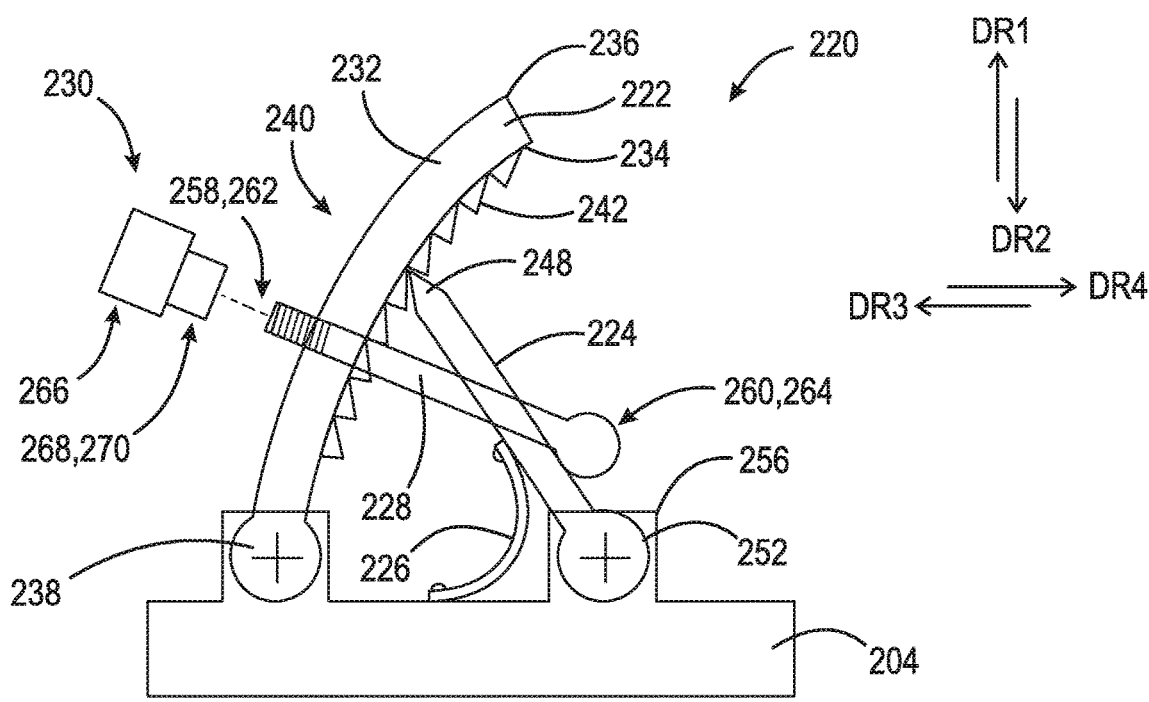
FIG. 17 is a side view of a second embodiment of a locking mechanism.
Figure 18:
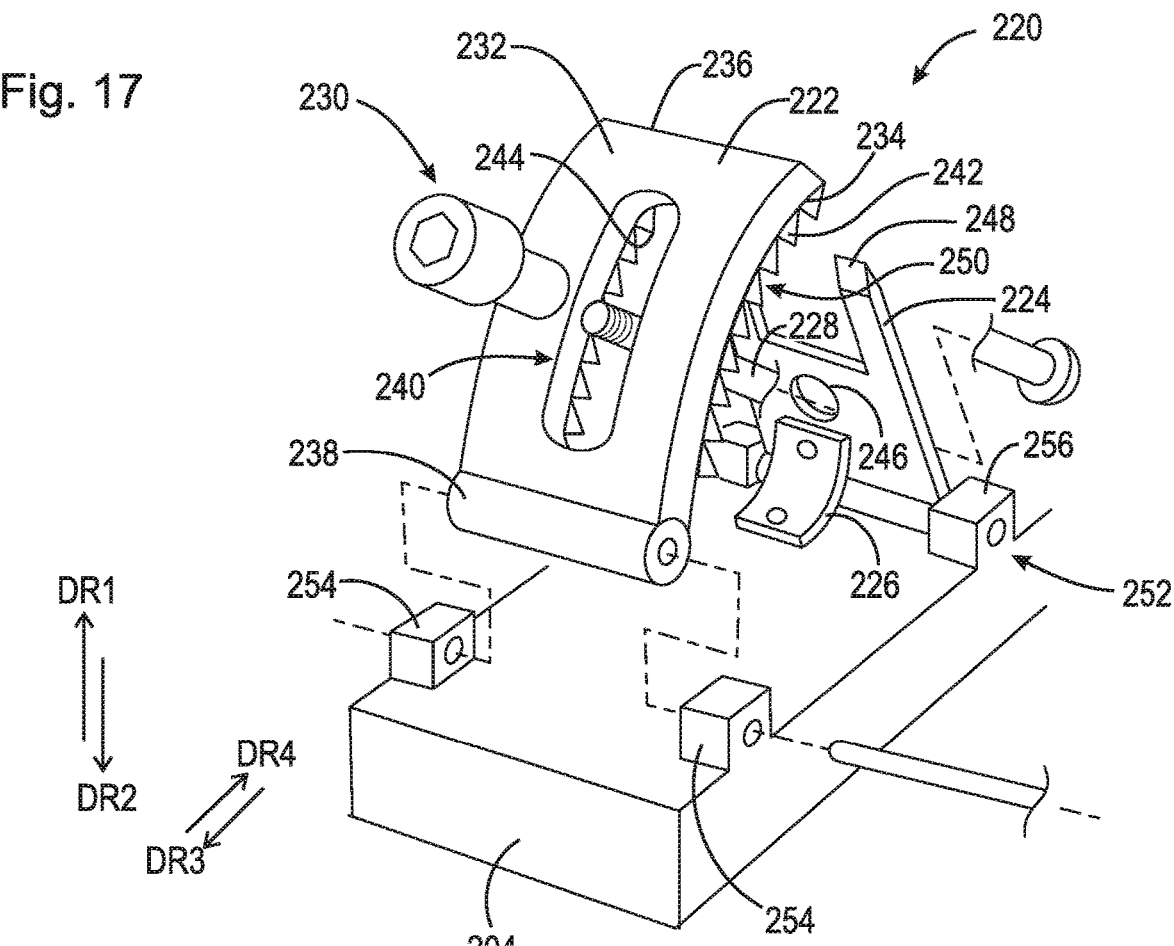
FIG. 18 is a front perspective partially exploded view of a second embodiment of a locking mechanism.

FIG. 17 is a side view of locking mechanism 220. Locking mechanism 220 comprises plate 222, pawl 224, biasing element 226, post 228, and fastener 230. Plate 222 includes first surface 232, second surface 234, corner 236, hinge 238, and through-bore 240 operatively arranged to receive post 228 and fastener 230. When in the locked position, corner 236 abuts superior component 102 to stop superior component 102 from being displaced in direction DR2. Second surface 234 comprises first plurality of teeth 242 and second plurality of teeth 244. Pawl 224 includes through-bore 246, first pawl head 248, second pawl head 250, and hinge 252. Through-bore 246 is operatively arranged to accept post 228. First and second pawl heads 248 and 250 taper to a point and are operatively arranged to engage with first and second plurality of teeth 242 and 244, respectively, on second surface 234 of plate 222. Prior to locking, plate 222 and pawl 224 are freely pivotable about hinges 238 and 252, respectively. Hinges 238 and 252 are pivotably secured to first protrusion 254 and second protrusion 256 of inferior component 204 (discussed infra), respectively. It should be appreciated that although hinges 238 and 252 are illustrated as pivotably secured to first protrusion 254 and second protrusion 256, respectively, hinges 238 and 252 could also be placed in a recess within inferior component 204. Biasing element 226 is fixedly secured between inferior component 204 and pawl 224 and provides spring bias to pawl 224 in direction DR1 and/or DR4. It should be appreciated that, although biasing element 226 is depicted in FIGS. 17-20 as a flat spring, other biasing elements known in the art can be used to bias pawl 224 in direction DR1. Post 228 includes first end 258 and second end 260. First end 258 includes male threading 262, and second end 260 includes a stopping element 264. It should be appreciated that, although stopping element 264 is depicted as a spherical member, other variations of stopping elements can be used, e.g., a flanged stopping element. Fastener 230 includes first end 266 and second end 268. First end 266 is operatively arranged to engage with any device known in the art that can impart rotational motion onto fastener 230, e.g., a drill. Second end 268 includes female threading 270 operatively arranged to engage with male threading 262 of post 228.

After device 200 has been inserted into disc space 12 and expanded to an appropriate height, a surgeon can apply torque to first end 266 of fastener 230, pulling post 228 in direction DR3. As post 228 is pulled in direction DR3, stopping element 264 of post 228 forces pawl 224 in direction DR3 against biasing element 226 about hinge 252. When sufficient force is applied, first and second pawl heads 248 and 250, respectively, engage with first and second plurality of teeth 242 and 244 locking the plate 222 in place and preventing the collapse of device 200 (shown in FIGS. 19 and 20) in direction DR2.

Figure 19:
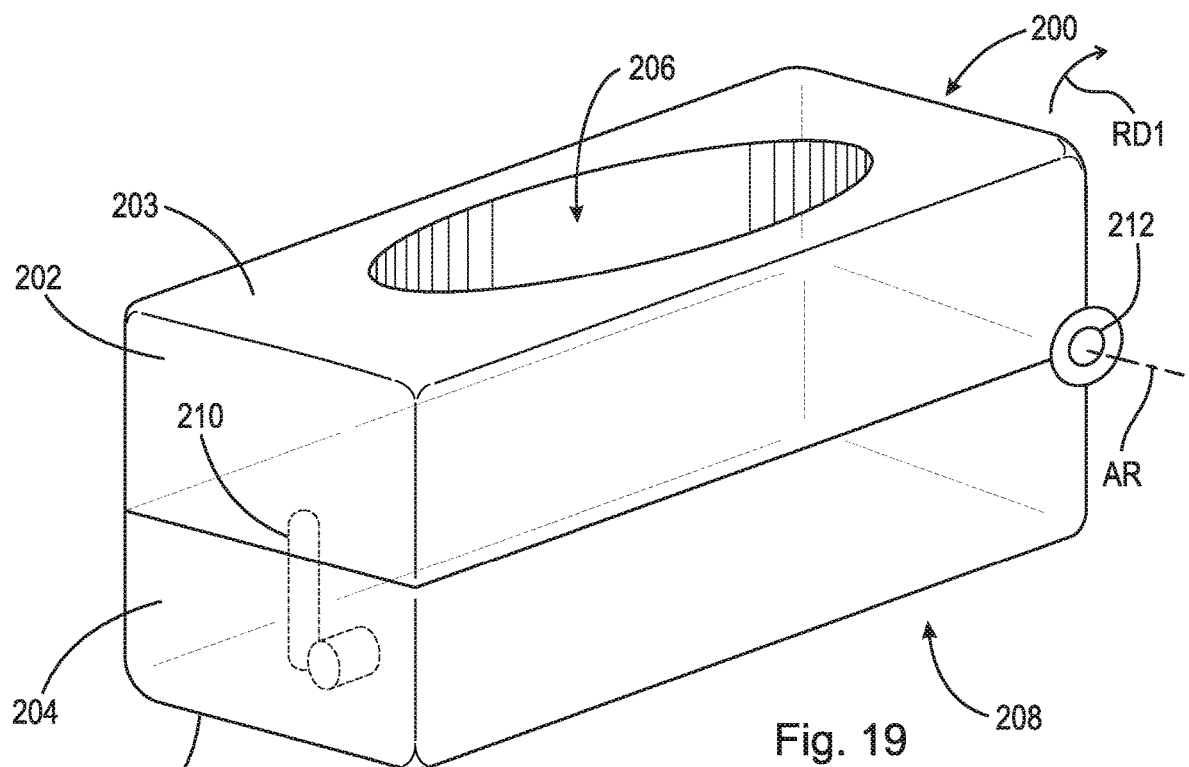
FIG. 19 is a front perspective view of a stand-alone expandable interbody spinal fusion device with a second embodiment of a locking mechanism, in an unexpanded state.

FIG. 19 is a front perspective view of device 200 having two locking mechanisms 214 and 216 in an unexpanded state. It should be appreciated that in an example embodiment locking mechanisms 214 and 216 are embodied as locking mechanism 220 discussed supra. Device 200 comprises superior component 202, inferior component 204, and expansion mechanism 210 arranged to displace superior component 202 in first direction DR1 relative to inferior component 204. Superior component 202 and inferior component 204 further comprise at least one first aperture 206 and at least one second aperture 208, respectively, which are arranged to allow fusion between bone fusing material and the adjacent vertebra. Superior component 202 has a first surface 203 and inferior component 204 has a first surface 205. Device 200 further comprises hinge 212 fixedly secured to superior component 202 and inferior component 204 and arranged to rotatably displace the superior component about axis of rotation AR. Expansion mechanism 210 is preferably expansion mechanism 176 described supra. Although FIGS. 19 and 20 depict expansion mechanism 210 fixedly secured within inferior component 204, it should be appreciated that expansion mechanism 210 could also be fixedly secured within superior component 202.

Figure 20:
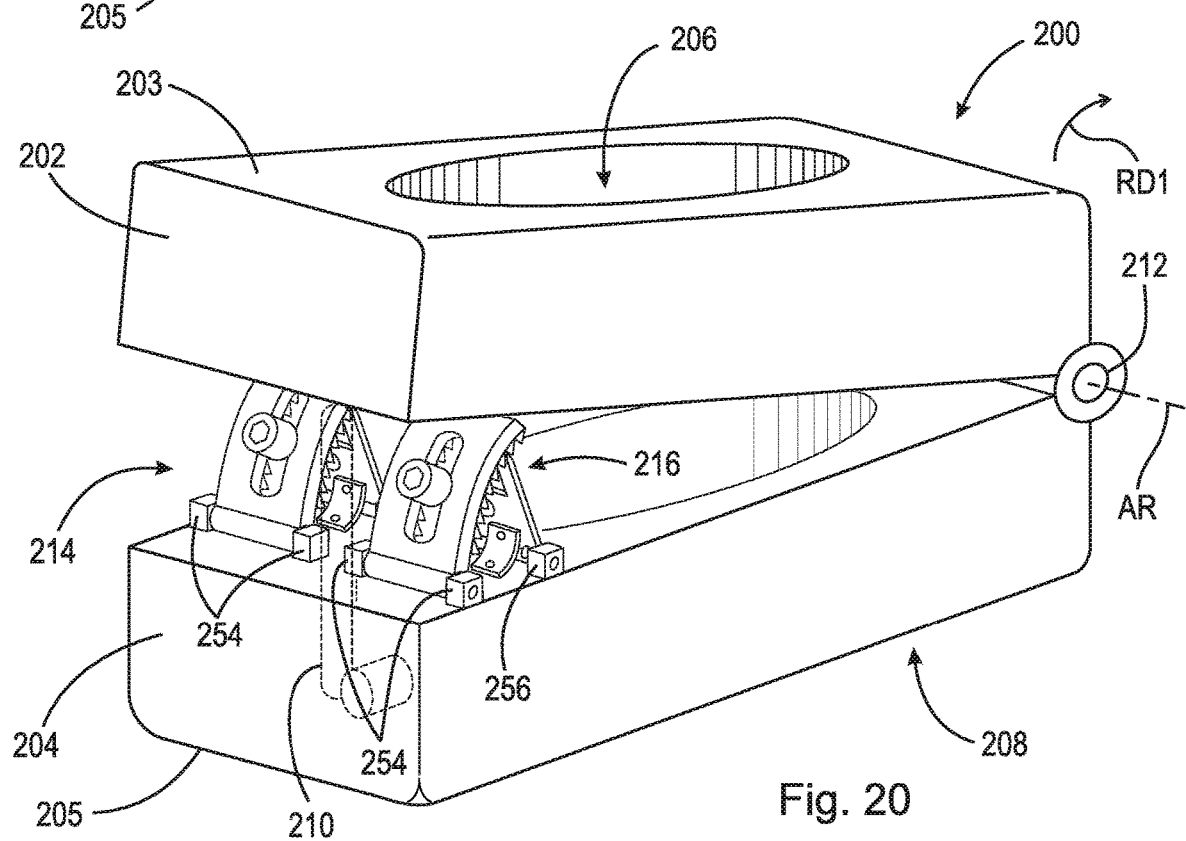
FIG. 20 is a front perspective view of a stand-alone expandable interbody spinal fusion device with a second embodiment of a locking mechanism, in an expanded state.

FIG. 20 is a front perspective view of device 200 having locking mechanisms 214 and 216 in an expanded state. After superior component 202 is displaced about axis of rotation AR, locking mechanisms 214 and 216 are engaged and locked as discussed supra. Once locked, superior component 202 is prevented from moving in direction DR2.

Figure 21:
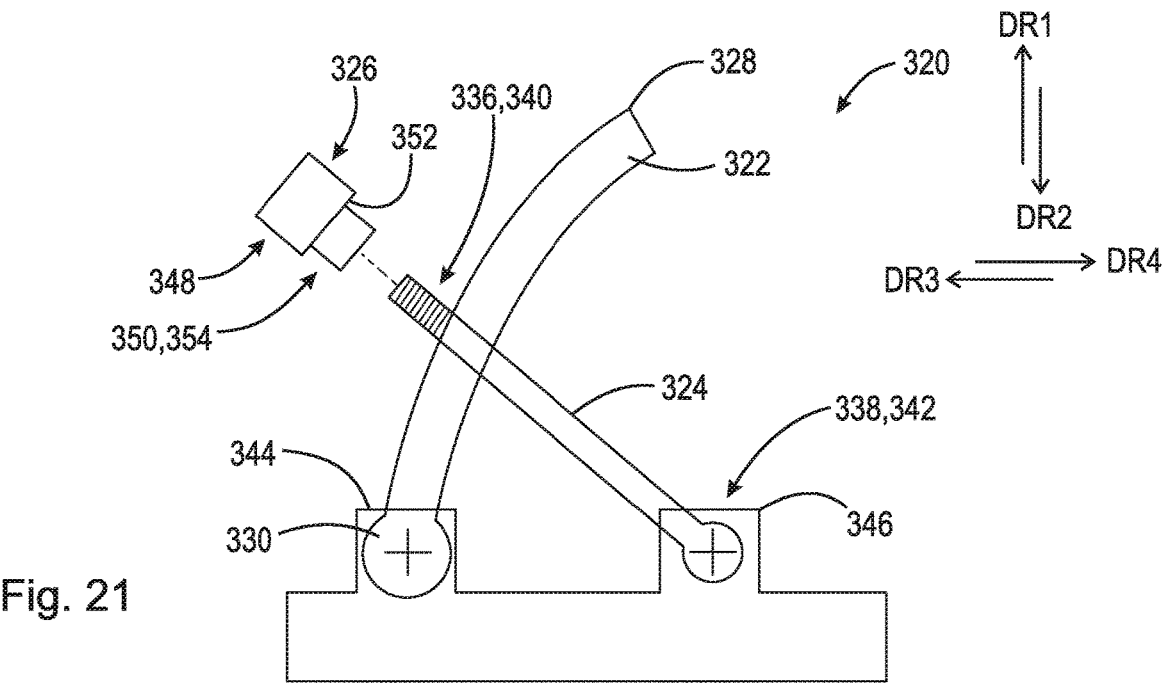
FIG. 21 is a side view of a third embodiment of a locking mechanism.
Figure 22:
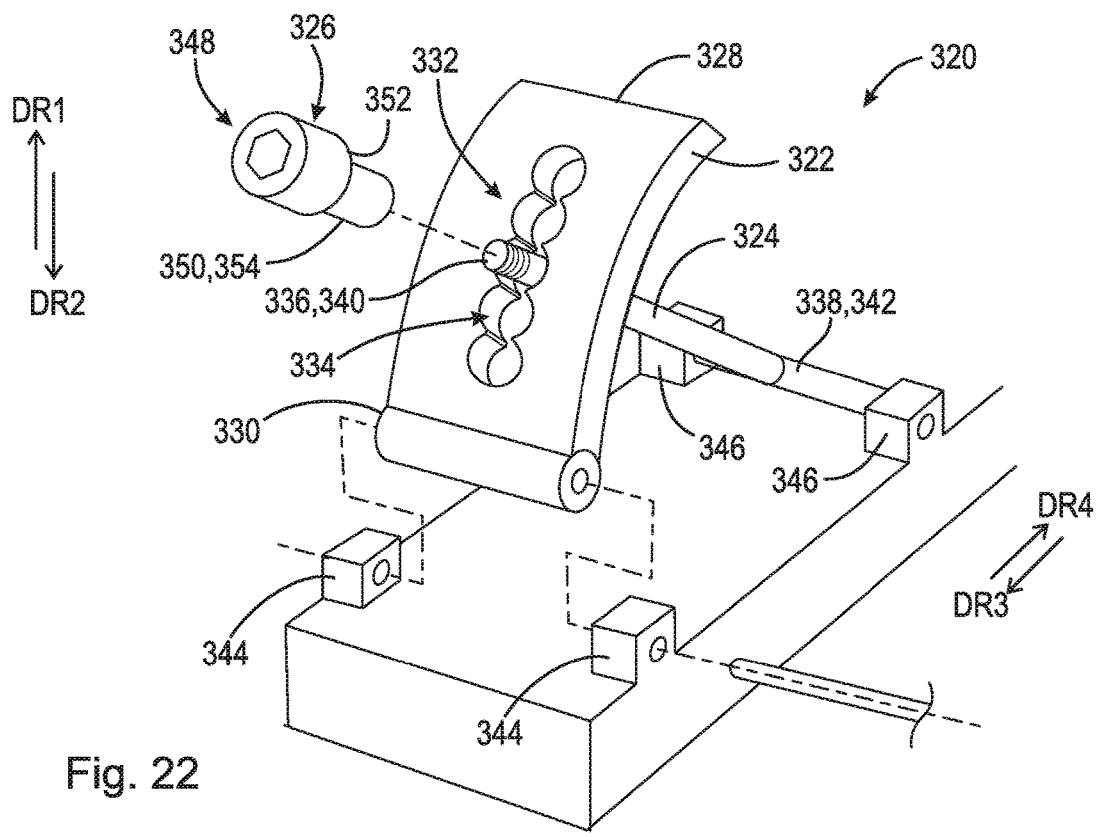
FIG. 22 is a front perspective partially exploded view of a third embodiment of a locking mechanism.

FIG. 21 is a side view of locking mechanism 320. Locking mechanism 320 comprises plate 322, post 324, and fastener 326. Plate 322 includes corner 328, hinge 330, and plurality of through-bores 332 operatively arranged to receive post 324 and fastener 326. When in the locked position, corner 328 abuts superior component 102 to stop superior component 102 from being displaced in direction DR2. Post 324 includes first end 336 and second end 338. First end 336 includes male threading 340, and second end 338 includes hinge 342. Plurality of through-bores 332 (illustrated in FIG. 22) further includes longitudinal space 334 arranged to receive first end 336 of post 324. Before locking, plate 322 and post 324 are freely pivotable about hinges 330 and 342, respectively, and first end 336 of post 324 moves freely within longitudinal space 334 (shown in FIG. 22) of plurality of through-bores 332. Hinges 330 and 342 are pivotably secured to first protrusion 344 and second protrusion 346, respectively, of inferior component 302 (discussed infra). It should be appreciated that although hinges 330 and 342 are illustrated as pivotably secured to first protrusion 344 and second protrusion 346, respectively, hinges 330 and 342 could also be placed in a recess within inferior component 304. Fastener 326 includes first end 348, second end 350, and flange 352. First end 348 is operatively arranged to engage with any device known in the art that can impart rotational motion onto fastener 326, e.g., a drill. Second end 350 includes female threading 354 operatively arranged to engage with male threading 340 of post 324. Flange 352 has diameter D1 and is operatively arranged to abut against the surface of plate 322 when second end 350 is seated within one of plurality of through-bores 332 of plate 322.

After device 300 (shown in FIGS. 23 and 24) has been inserted into disc space 12 and expanded to an appropriate height, a surgeon can apply torque to first end 348 of fastener 326, pulling fastener 326 in direction DR4. As fastener 326 is pulled in direction DR4, flange 352 also moves in direction DR4 until flange 352 abuts the surface of plate 322 while second end 350 of fastener 326 is seated within one of plurality of through-bores 332 of plate 322 locking plate 322 in place and preventing the collapse of device 300 (shown in FIGS. 23 and 24) in direction DR2.

FIG. 23 is a front perspective view of device 300 with locking mechanisms 314 and 316, in an unexpanded state. It should be appreciated that in an example embodiment, locking mechanisms 314 and 316 are embodied as locking mechanism 320 discussed supra. Device 300 comprises superior component 302, inferior component 304, and expansion mechanism 310 arranged to displace superior component 302 in a first direction DR1 relative to inferior component 304. Superior component 302 and inferior component 304 further comprise at least one first aperture 306 and at least one second aperture 308, respectively, which are arranged to allow fusion between bone fusing material and the adjacent vertebra. Superior component 302 has a first surface 303 and inferior component 304 has a first surface 305. Device 300 further comprises hinge 312 fixedly secured to superior component 302 and inferior component 304 and arranged to rotatably displace the superior component about axis of rotation AR. Although FIGS. 23 and 24 depict expansion mechanism 310 fixedly secured within inferior component 304, it should be appreciated that expansion mechanism 310 could also be fixedly secured within superior component 302.

FIG. 24 is a front perspective view device 300 with locking mechanisms 314 and 316, in an expanded state. After superior component 302 is displaced about axis of rotation AR, locking mechanisms 314 and 316 are engaged and locked as discussed supra. Once locked, superior component 302 is prevented from moving in direction DR2.

FIG. 25 is a partial front perspective view of a locking mechanism 420 in an unlocked state. Locking mechanism 420 comprises plates 422 and 424, post 426, and fastener 428. Plates 422 and 424 are fixedly secured to superior component 402 and inferior component 404 (discussed infra), respectively. Plates 422 and 424 include first plurality of through-bores 430 and second plurality of through-bores 432, respectively. First plurality of through-bores 430 and second plurality of through-bores 432, which have diameter D2, less than diameter D3, and greater than diameter D1. First plurality of through-bores 430 and second plurality of through-bores 432 are operatively arranged to receive post 426 and fastener 428. First plurality of through-bores 430 includes longitudinal space 434, and second plurality of through-bores 432 includes longitudinal space 436. Post 426 includes a first end 438 and a second end 440. First end 438 has diameter D1 and includes male threading 442, and second end 440 includes shoulder 444 and stopping element 446. Shoulder 444 has diameter D2 and is operatively arranged to engage with first plurality of through-bores 430. Fastener 428 includes first end 448 and second end 450. First end 448 has diameter D3 (shown in FIG. 26) and is operatively arranged to engage with any device known in the art that can impart rotational motion onto fastener 428, e.g., a drill. Second end 450 has diameter D2 and includes female threading 452 operatively arranged to engage with male threading 442 of post 426.

Before locking, post 426 is freely moveable within longitudinal spaces 434 and 436. During surgery, and after device 400 (discussed infra) has been expanded to its final height, a surgeon imparts rotational motion to fastener 428. Female threading 452 of fastener 428 engages with male threading 442 of post 426 pulling post 426 in direction DR3. Post 426 is pulled in direction DR3 until shoulder 444 engages one of the through-bores of first plurality of through-bores 430 and second end 450 of fastener 428 engages one of the through-bores of the second plurality of through-bores 432. When both second end 450 of fastener 428 and shoulder 444 of post 426 are engaged with the respective through-bores, device 400 is locked and is prevented from collapsing in direction DR2. It should be appreciated that, although not depicted in the figures, it is possible for shoulder 444 or second end 450 of fastener 428 to engage with both the first plurality of through-bores 430 and second plurality of through-bores 432 simultaneously. FIG. 26 is a partial front perspective view of a locking mechanism 420 in a locked state. When device 400 is in the fully collapsed state, plates 422 and 424 nest within recesses 418.

Figure 27:
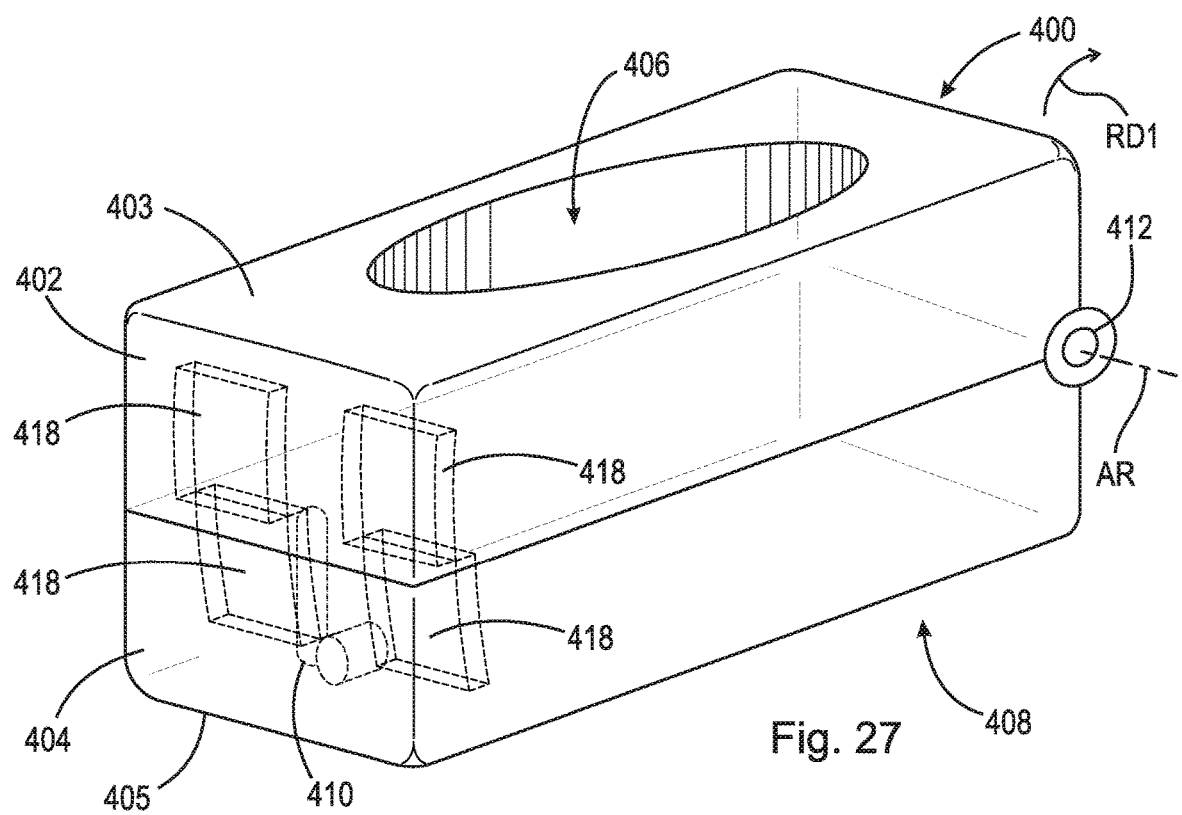
FIG. 27 is a front partially-exploded perspective view of a stand-alone expandable interbody spinal fusion device with a fourth embodiment of a locking mechanism in an unexpanded state.
Figure 28:
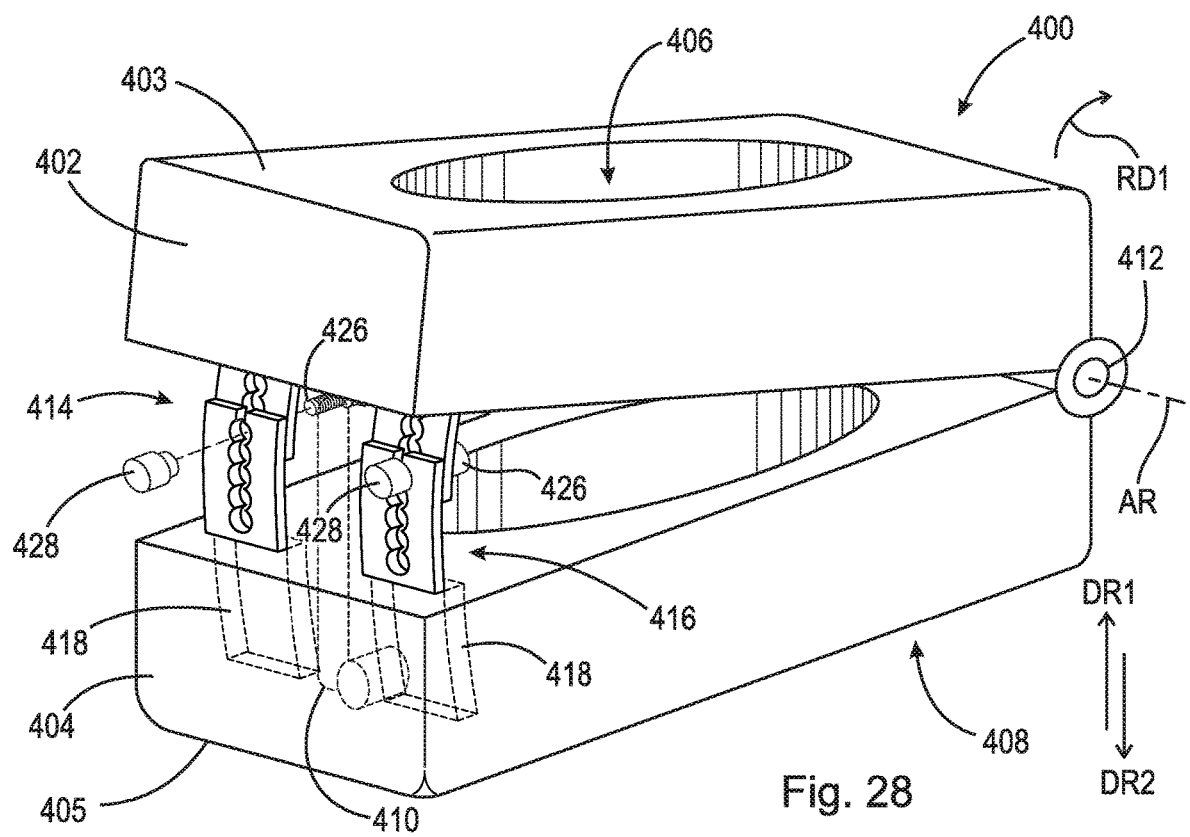
FIG. 28 is a front perspective view of a stand-alone expandable interbody spinal fusion device with a fourth embodiment of a locking mechanism in an expanded state.

FIG. 27 is a front perspective view of device 400 with locking mechanisms 414 and 416, in an unexpanded state. Device 400 comprises superior component 402, inferior component 404, and expansion mechanism 410 arranged to displace superior component 402 in a first direction DR1 relative to inferior component 404. Superior component 402 and inferior component 404 further comprise at least one first aperture 406 and at least one second aperture 408, which are arranged to allow fusion between bone fusing material and the adjacent vertebra. Superior component 402 has a first surface 403 and inferior component 404 has a first surface 405. Device 400 further comprises hinge 412 fixedly secured to superior component 402 and inferior component 404 and arranged to rotatably displace the superior component about axis of rotation AR. Locking mechanisms 414 and 416 are preferably locking mechanism 420 described supra. Expansion mechanism 410 is preferably expansion mechanism 176 described supra. It should be noted that since plates 422 and 424 are fixedly secured to superior and inferior components 102 and 104, respectively, recesses 418 are provided within which plates 422 and 424 can nest while device 400 is in a collapsed state. It should further be appreciated that plates 422 and 424 can be hingedly secured to superior component 402 and inferior component 404, respectively. FIG. 28 is a front perspective view of device 400 with locking mechanisms 414 and 416 in an expanded state.

FIG. 29 is a partial front perspective view of a locking mechanism 520 in an unlocked state. Locking mechanism 520 comprises plates 522 and 524, and fastener 426. Plates 522 and 524 are fixedly secured to superior component 502 and inferior component 504 (discussed infra), respectively. Plate 522 includes first plurality of through-bores 530 and plate 524 includes second plurality of through-bores 532. Each through-bore of first plurality of through-bores 530 has diameter D2. Each through-bore of the second plurality of through-bores 532 has diameter D1 larger than D2. First plurality of through-bores 530 and second plurality of through-bores 532 are operatively arranged to fastener 526. Second plurality of through-bores 532 further includes longitudinal space 534. Fastener 526 includes first end 540 and second end 542. First end 540 has diameter D2 and is operatively arranged to engage with any device known in the art that can impart rotational motion onto fastener 526, e.g., a drill. Second end 542 has diameter D1 and includes male threading 544 operatively arranged to engage with any of the through-bores of first plurality of through-bores 530.

Before locking, fastener 526 is freely moveable within longitudinal space 534. During surgery, and after device 500 (discussed infra) has been expanded to its final height, a surgeon imparts rotational motion to fastener 526. Male threading 544 of fastener 526 engages any of the through-bores of first plurality of through-bores 530 which pulls fastener 526 in direction DR4. When first end 540 of fastener 526 is engaged with second plurality of through-bores 532 and second end 542 is engaged with first plurality of through-bores 530, device 500 is locked and prevented from collapsing in direction DR2. FIG. 30 is a partial front perspective view of a locking mechanism 520 in a locked state. When device 500 is in the fully collapsed state, plates 522 and 524 nest within recesses 518.

Figure 31:
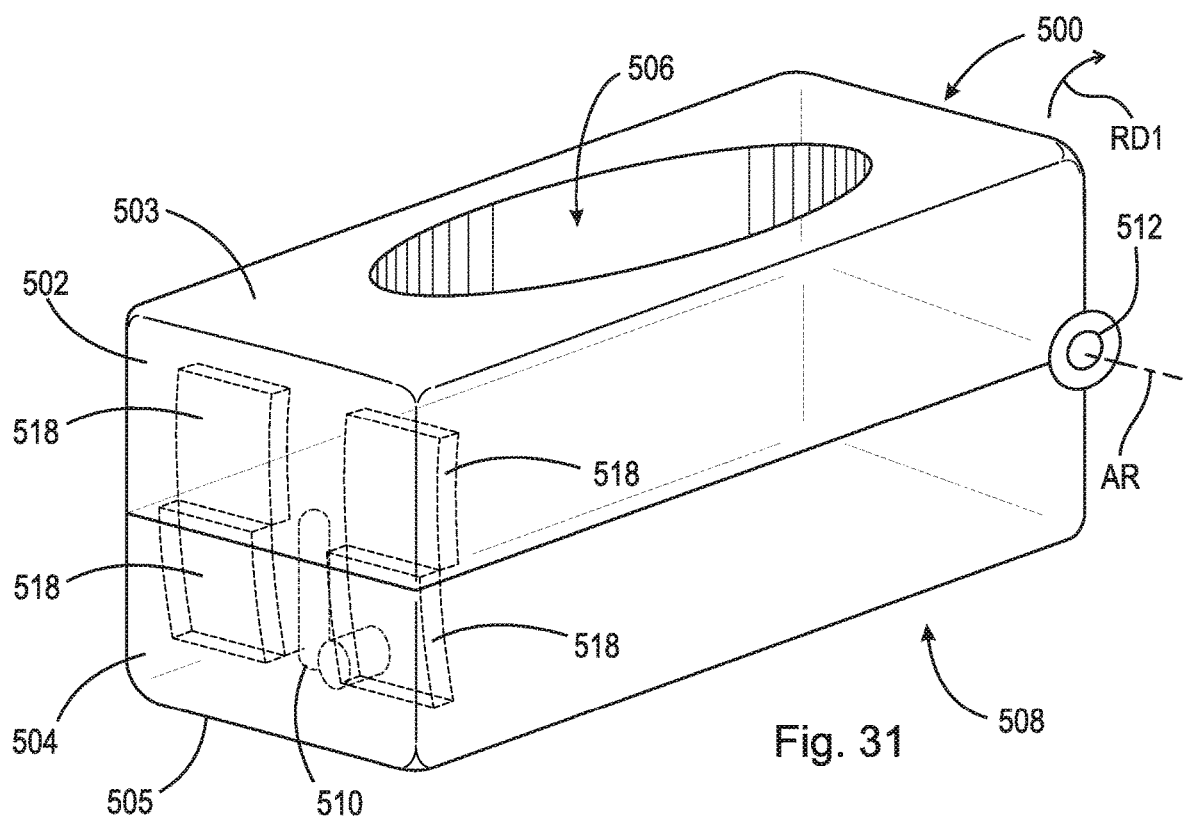
FIG. 31 is a front partially-exploded perspective view of a stand-alone expandable interbody spinal fusion device with a fifth embodiment of a locking mechanism in an unexpanded state.
Figure 32:
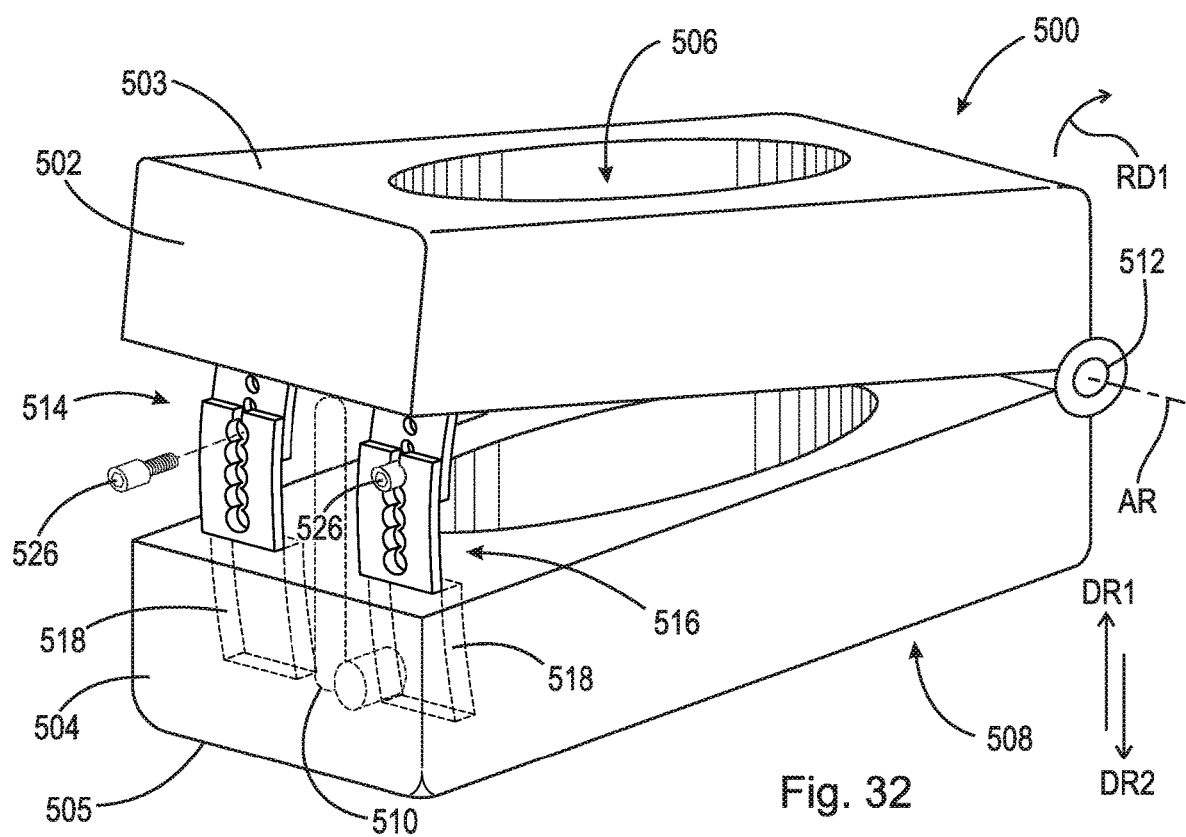
FIG. 32 is a front partially-exploded perspective view of a stand-alone expandable interbody spinal fusion device with a fifth embodiment of a locking mechanism in an expanded state.

FIG. 31 is a front perspective view of device 500 with locking mechanisms 514 and 516, in an unexpanded state. Device 500 comprises superior component 502, inferior component 504, and expansion mechanism 510 arranged to displace superior component 502 in a first direction DR1 relative to inferior component 504. Superior component 502 and inferior component 504 further comprise at least one first aperture 506 and at least one second aperture 508, which are arranged to allow fusion between bone fusing material and the adjacent vertebra. Superior component 502 has a first surface 503 and inferior component 504 has a first surface 505. Device 500 further comprises hinge 512 fixedly secured to superior component 502 and inferior component 504 and arranged to rotatably displace the superior component about axis of rotation AR. Locking mechanisms 514 and 516 are preferably locking mechanism 520 described supra. Expansion mechanism 510 is preferably expansion mechanism 176 described supra. It should be noted that since plates 522 and 524 are fixedly secured to superior and inferior components 502 and 504, respectively, recesses 518 are provided within which plates 522 and 524 can nest while device 500 is in a collapsed state. It should further be appreciated that plates 522 and 524 can be hingedly secured to superior component 502 and inferior component 504, respectively. FIG. 32 is a front perspective view of device 500 with locking mechanisms 514 and 516 in an expanded state.

Figure 33:
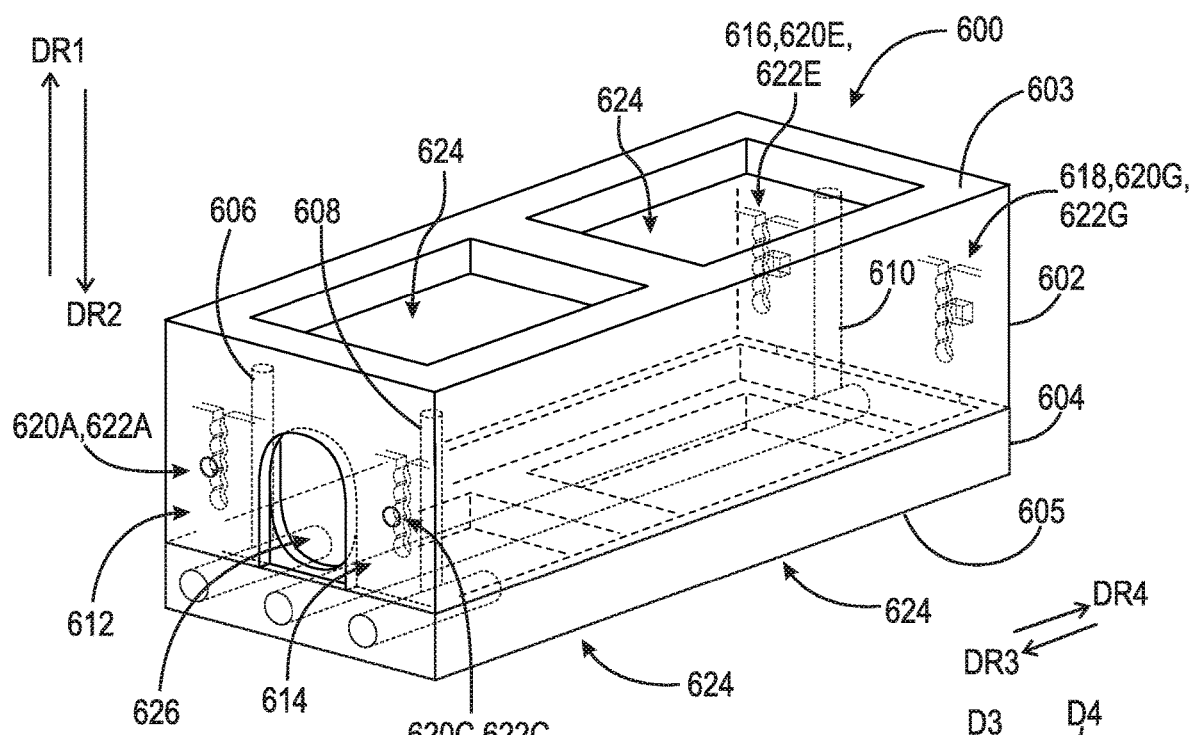
FIG. 33 is a perspective view of a sixth embodiment of a stand-alone expandable interbody spinal fusion device, in an unexpanded state.

FIG. 33 is a perspective view of stand-alone expandable interbody spinal fusion device 600, in an unexpanded state. Device 600 comprises superior component 602, inferior component 604, and expansion mechanisms 606, 608, and 610 (described infra) arranged to displace superior component 602 in a first direction DR1 relative to inferior component 604, giving device 600 an expanded height $H_2$ greater than unexpanded height $H_1$ (shown in FIGS. 37 and 38). Device 600 also comprises locking mechanisms 612, 614, 616, and 618 arranged between superior component 602 and inferior component 604.

Figure 34:
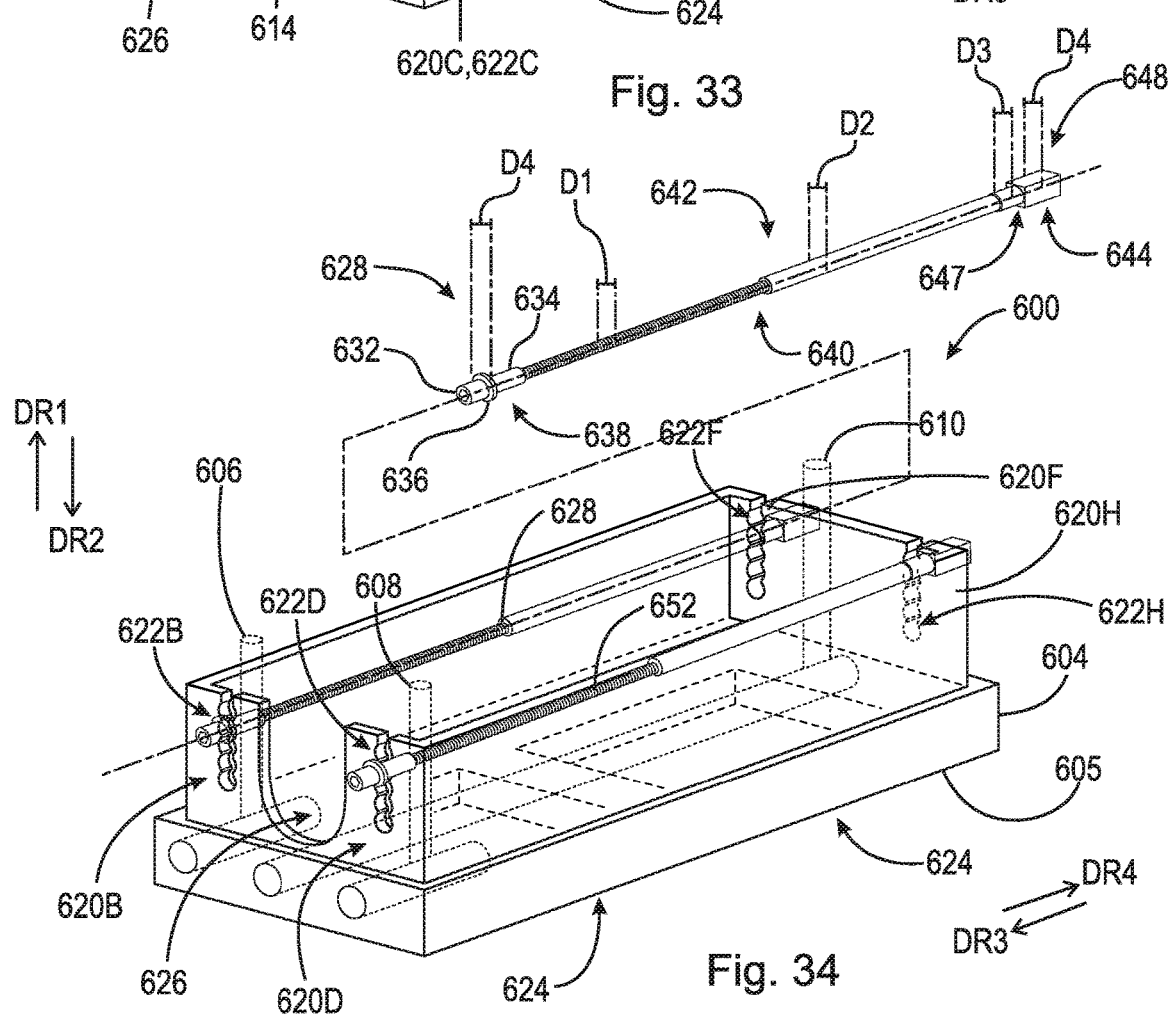
FIG. 34 is a partially-exploded perspective view of a stand-alone expandable interbody spinal fusion device with a sixth embodiment of a locking mechanism, in an expanded state.

Locking mechanism 612 comprises plate 620A (shown in FIG. 33) and 620B (shown in FIG. 34). Locking mechanism 614 comprises plates 620C (shown in FIG. 33) and 620D (shown in FIG. 34). Locking mechanism 616 comprises plates 620E (shown in FIG. 33) and 620F (shown in FIG. 34). Locking mechanism 618 comprises plates 620G (shown in FIG. 33) and 620H (shown in FIG. 34). Plates 620A and 620C further include through-bores 622A and 622C, respectively. Plates 620E and 620G further comprise square through-bores 622E and 622G, respectively. Plates 620B, 620D, 620F, and 620H further comprise a plurality of through-bores, i.e., plurality of through-bores 622B, 622D, 622F, and 622H, respectively. It should be appreciated that, although plates 620A-620H are shown as integral within superior component 602 and inferior component 604, plates 620A-620H could also be discrete plates, fixedly secured to superior component 602 and inferior component 604.

Superior component 602 and inferior component 604 further comprise at least one first aperture 624 arranged to allow fusion between bone fusing material and the adjacent vertebra and a second aperture 626 located on the front face of device 600 and arranged to allow the introduction of bone fusing material into device 600. Second aperture 626 is illustrated as an arched slot as a non-limiting example, however, it should be appreciated that second aperture 626 could be an aperture of any suitable shape, e.g., triangular, circular, rectangular, elliptical, etc., that would allow for the introduction of bone fusing material into device 600. Superior component 602 has a first surface 603 and inferior component 604 has a first surface 605.

FIG. 34 is a perspective view of stand-alone expandable interbody spinal fusion device 600, in an expanded state. It should be appreciated that FIG. 34 is a partial view, i.e., superior component 602 has been removed for clarity. During surgery and after device 600 is implanted in disc space 12, a surgeon can apply torque to expansion mechanisms 606, 608, and 610 via any device that imparts rotational force upon expansion mechanisms 606, 608, and 610 (e.g., a screw driver or impact driver). Expansion mechanisms 606, 608 and 610 are preferably the embodiment illustrated in FIGS. 15 and 16, described supra. Furthermore, it should be appreciated that although expansion mechanisms 606, 608, and 610 are depicted within inferior component 604 in FIGS. 33-38, expansion mechanisms 606, 608, and 610 could be arranged within superior component 602. The rotational force causes expansion mechanisms 606, 608, and 610 to displace superior component 602 in direction DR1 relative to inferior component 604 giving device 600 an expanded height $H_2$, greater than $H_1$ (shown in FIGS. 37 and 38). It should be appreciated that expansion mechanisms 606, 608, and 610 can be expanded to any height between unexpanded height $H_1$ and expanded height $H_2$. Device 600 further comprises post 628. Post 628 is provided to secure locking mechanisms 612 and 616 in position once device 600 is expanded to its final height. Post 628 comprises first section 638, second section 640, third section 642, and fourth section 644. First section 638 has a first end 632, a second end 634, and a flange 636. First end 632 is operatively arranged to engage with any device known in the art that can impart rotational motion onto first section 638, e.g., a drill. Second end 634 is arranged non-rotatably secure to second section 640. Second section 640 includes external helical male threading 646. Third section 642 includes a substantially hollow shaft with cavity 650. Cavity 650 includes internal helical female threading 651 operatively arranged to engage with male threading 646. Fourth section 644 includes cylindrical portion 647 non-rotatably secured to third section 642 and stopping element 648 which is embodied as a substantially rectangular member operatively arranged to abut the surface of plate 620F and prevent movement of post 628 in direction DR3. Second section 640 has a diameter D1. Third section 642 has diameter D2 larger than D1. Cylindrical portion 647 of fourth section 644 has diameter D3 larger than D2, and stopping element 648 has diameter D4 larger than D3. Flange 636 has diameter D4 larger than D3.

Prior to locking, first end 632 of first section 638 is slidingly engaged with through-bore 622A (shown in FIG. 33); second section 640 is loosely seated in the longitudinal space formed between each through-bore of plurality of through-bores 622B of plate 620B; third section 642 is loosely seated in the longitudinal space formed between each through-bore of plurality of through-bores 622F of plate 620F; and cylindrical portion 647 of fourth section 644 is slidingly engaged with square through-bore 622E of plate 620E.

After device 600 has been inserted into disc space 12 and expanded to an appropriate height, a surgeon can apply torque to first end 632 of first section 638. The torque is then transferred to second section 640 having male threading 646. Second section 640 engages with female threading 651 in cavity 650 of third section 642, pulling post 628 in direction DR3 into the locked position. In the locked position, flange 636 abuts the surface of plate 620A preventing further displacement in direction DR4, and second end 634 of first section 638 is completely seated in one of the through-bores of plurality of through-bores 622B which corresponds to the chosen device height. In this locked position, device 600 is prevented from collapsing in direction DR2. Additionally, in the locked position, cylindrical portion 647 of fourth section 644 is completely seated in one of the through-bores of plurality of through-bores 622F of plate 620F, and stopping element 648 abuts the outer surface of plate 620F, thereby preventing further displacement of third section 642 and fourth section 644 in direction DR3.

Device 600 further comprises post 652 (shown in FIGS. 34, 36, and 38). Post 652 is provided to secure locking mechanisms 614 and 618 in position once device 600 is expanded to its final height. Post 652 further comprises first section 662, second section 644, third section 666, and fourth section 668. First section 662 includes first end 656, second end 658, and flange 660. First end 656 includes a recess operatively arranged to engage with any device known in the art that can impart rotational motion onto first section 662, e.g., a drill. Second end 658 is non-rotatably secured to second section 664. Second section 664 includes external helical male threading 670. Third section 666 includes a substantially hollow shaft with cavity 674. Cavity 674 includes internal helical female threading 675 operatively arranged to engage with male threading 670. Fourth section 668 includes cylindrical portion 671 non-rotatably secured to third section 666 and stopping element 672, which is embodied as a substantially rectangular member operatively arranged to abut the surface of plate 620H and prevent movement of post 652 in direction DR3. Second section 664 has a diameter D1. Third section 666 has diameter D2 larger than D1. Cylindrical portion 671 of fourth section 668 has diameter D3 larger than D2, and stopping element 672 has diameter D4 larger than D3. Flange 660 has diameter D4 larger than D3.

After device 600 has been inserted into disc space 12 and expanded to an appropriate height, a surgeon can apply torque to first end 656 of first section 662. The torque is then transferred to second section 664 having male threading 670. Second section 664 engages with female threading 675 in cavity 674 of third section 666, pulling post 652 in direction DR3 into the locked position. In the locked position, flange 660 abuts the surface of plate 620C preventing further displacement in direction DR4, second end 658 of first section 662 is completely seated in one of the through-bores of plurality of through-bores 622D which corresponds to the chosen device height. In this locked position, device 600 is prevented from collapsing in direction DR2. Additionally, in the locked position, cylindrical portion 671 of fourth section 668 is completely seated in one of the through-bores of plurality of through-bores 622H of plate 620H, and stopping element 672 abuts the outer surface of plate 620F, thereby preventing further displacement of third section 642 and fourth section 644 in direction DR3.

FIG. 39 is a partial front perspective view of a locking mechanism 720 in an unlocked state. Locking mechanism 720 comprises plate 722, plate 724, and fastener 726. Plates 722 and 724 are fixedly secured to superior component 702 and inferior component 704 (discussed infra), respectively. Plate 722 includes plurality of catches 730 and plate 724 includes through-bore 732. Through-bore 732 has female threading 734. Plurality of catches 730 is illustrated as a plurality of tapered depressions having a taper back section and a flat ridge similar to a ratchet mechanism, which is arranged to prevent motion in one direction while allowing motion in a second direction. Fastener 726 includes first end 740 and second end 742. Second end 742 has diameter D1 and includes male threading 744 operatively arranged to engage with female threading 734 of through-bore 732. First end 740 of fastener 726 has diameter D2 larger than D1. First end 740 is operatively arranged to engage with any device known in the art that can impart rotational motion onto fastener 726, e.g., a drill. Each catch of plurality of catches 730 has a width greater than or equal to diameter D2.

Before locking, fastener 726 is loosely engaged with female threading 734 of through-bore 732. During surgery, and after device 700 (discussed infra) has been expanded to its final height, a surgeon imparts rotational motion to fastener 726. Male threading 744 of fastener 726 further engages with female threading 734 of through-bore 732 which pulls fastener 726 in direction DR4. When second end 742 of fastener 726 is engaged with one of the catches of plurality of catches 730, device 700 is locked and prevented from collapsing in direction DR2. FIG. 40 is a partial front perspective view of a locking mechanism 720 in a locked state. When device 700 is in the fully collapsed state, plates 722 and 724 nest within recesses 718.

Figure 41:
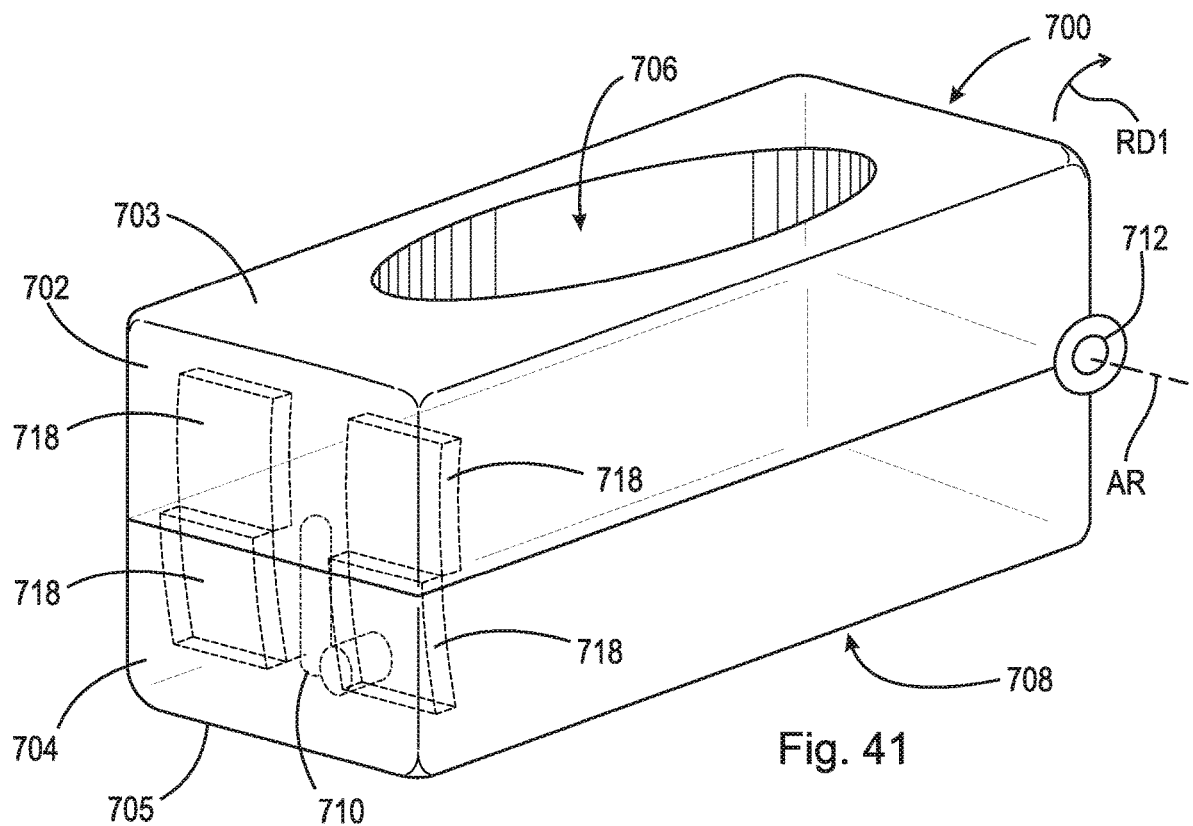
FIG. 41 is a front partially-exploded perspective view of a stand-alone expandable interbody spinal fusion device with a seventh embodiment of a locking mechanism in an unexpanded state.
Figure 42:
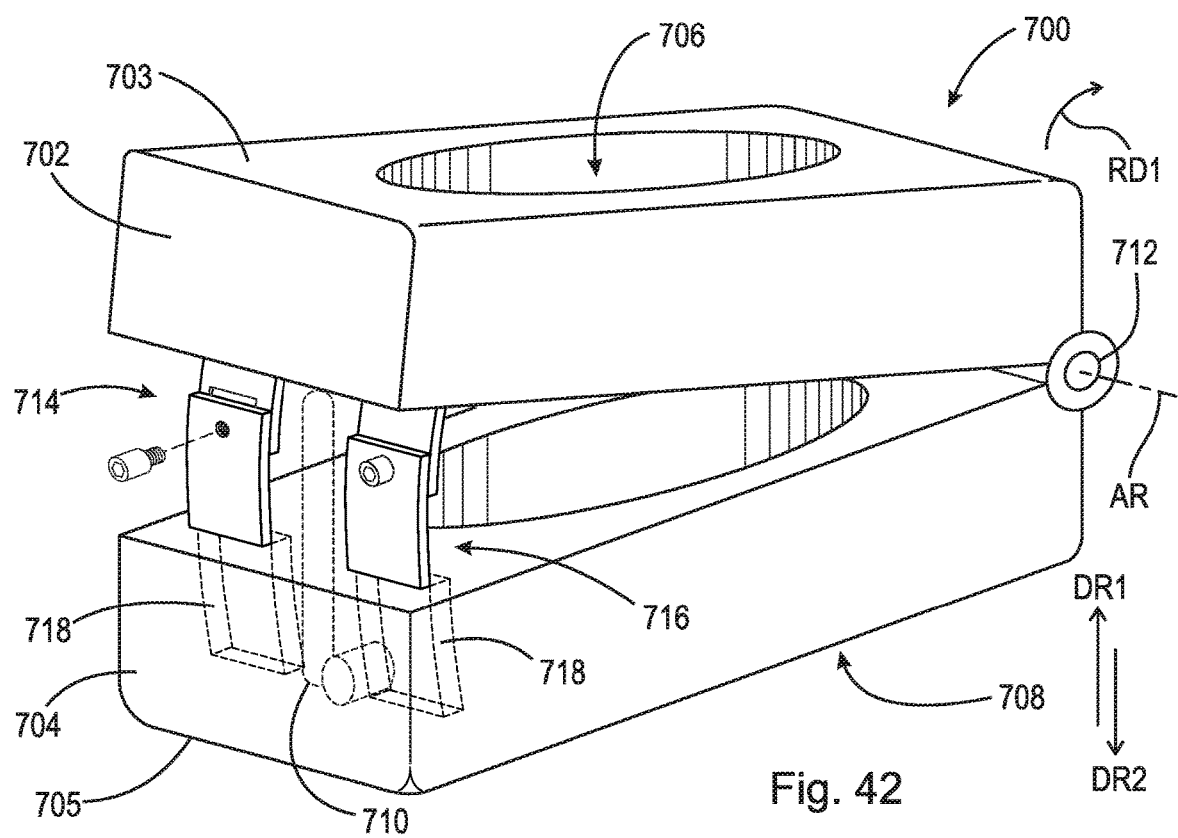
FIG. 42 is a front perspective view of a stand-alone expandable interbody spinal fusion device with a seventh embodiment of a locking mechanism in an expanded state.

FIG. 41 is a front perspective view of device 700 with locking mechanisms 714 and 716, in an unexpanded state. Device 700 comprises superior component 702, inferior component 704, and expansion mechanism 710 arranged to displace superior component 702 in a first direction DR1 relative to inferior component 704. Superior component 702 and inferior component 704 further comprise at least one first aperture 706 and at least one second aperture 708, which are arranged to allow fusion between bone fusing material and the adjacent vertebra. Superior component 702 has a first surface 703, and inferior component 704 has a first surface 705. Device 700 further comprises hinge 712 fixedly secured to superior component 702 and inferior component 704 and arranged to rotatably displace the superior component about axis of rotation AR. Locking mechanisms 714 and 716 are preferably locking mechanism 720 described supra. Expansion mechanism 710 is preferably expansion mechanism 176 described supra. It should be noted that since plates 722 and 724 are fixedly secured to superior and inferior components 702 and 704, respectively, recesses 718 are provided within which plates 722 and 724 can nest while device 700 is in a collapsed state. It should further be appreciated that plates 722 and 724 can be hingedly secured to superior component 702 and inferior component 704, respectively. FIG. 42 is a front perspective view of device 700 with locking mechanisms 714 and 716 in an expanded state.

FIG. 43 is a partial front perspective view of a locking mechanism 820 in an unlocked state. Locking mechanism 820 comprises plate 822, plate 824, and fastener 826. Plates 822 and 824 are fixedly secured to superior component 802 and inferior component 804 (discussed infra), respectively. Plate 822 includes plurality of catches 830 and plate 824 includes through-bore 832. Through-bore 832 has female threading 834. Plurality of catches 830 are illustrated as a series of cylindrical partial-through-bores. Fastener 826 includes first end 840 and second end 842. Second end 842 has diameter D1 and includes male threading 844 operatively arranged to engage with female threading 834 of through-bore 832. First end 840 of fastener 826 has diameter D2 larger than D1. First end 840 is operatively arranged to engage with any device known in the art that can impart rotational motion onto fastener 826, e.g., a drill. Each catch of plurality of catches 830 has a width greater than or equal to diameter D2.

Before locking, fastener 826 is loosely engaged with female threading 834 of through-bore 832. During surgery, and after device 800 (discussed infra) has been expanded to its final height, a surgeon imparts rotational motion to fastener 826. Male threading 844 of fastener 826 further engages with female threading 834 of through-bore 832, which pulls fastener 826 in direction DR4. When second end 842 of fastener 826 is engaged with one of the catches of plurality of catches 830, device 800 is locked and prevented from collapsing in direction DR2. FIG. 44 is a partial front perspective view of a locking mechanism 820 in a locked state. When device 800 is in the fully collapsed state, plates 822 and 824 nest within recesses 818.

Figure 45:
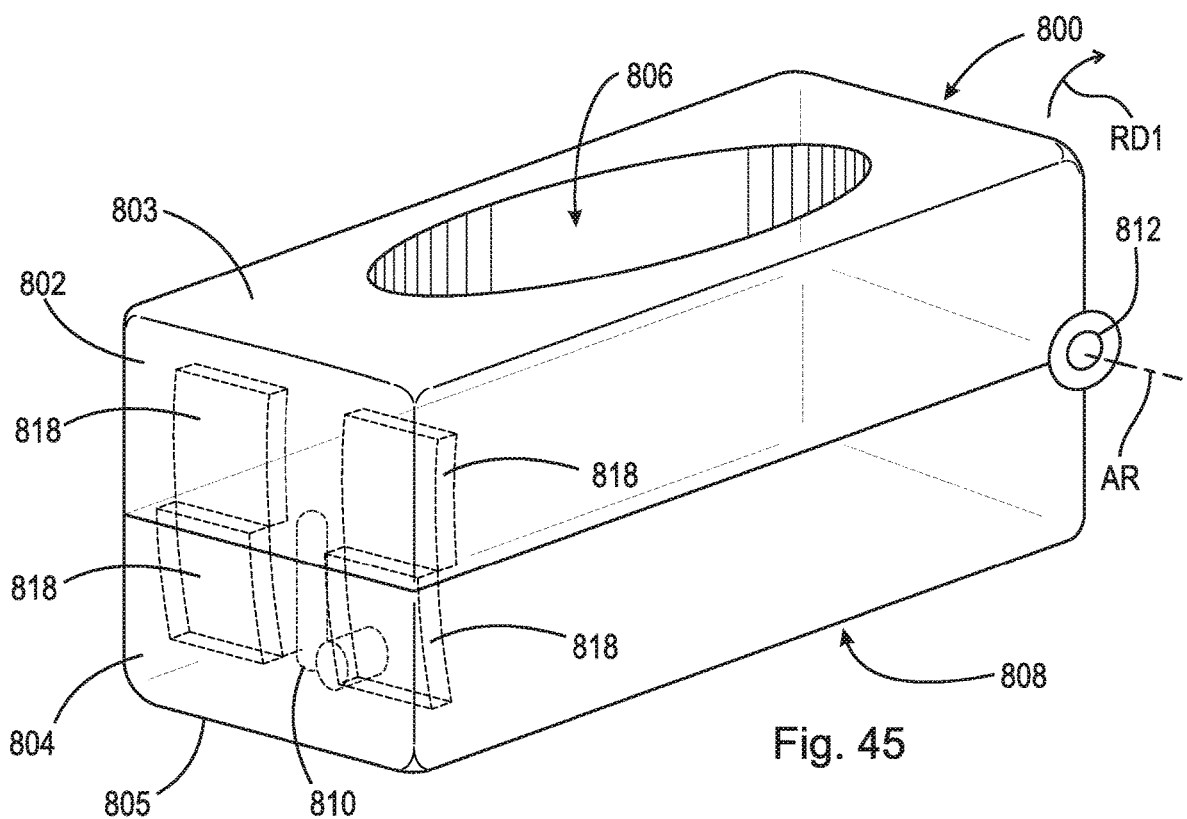
FIG. 45 is a front partially-exploded perspective view of a stand-alone expandable interbody spinal fusion device with an eighth embodiment of a locking mechanism in an unexpanded state.
Figure 46:
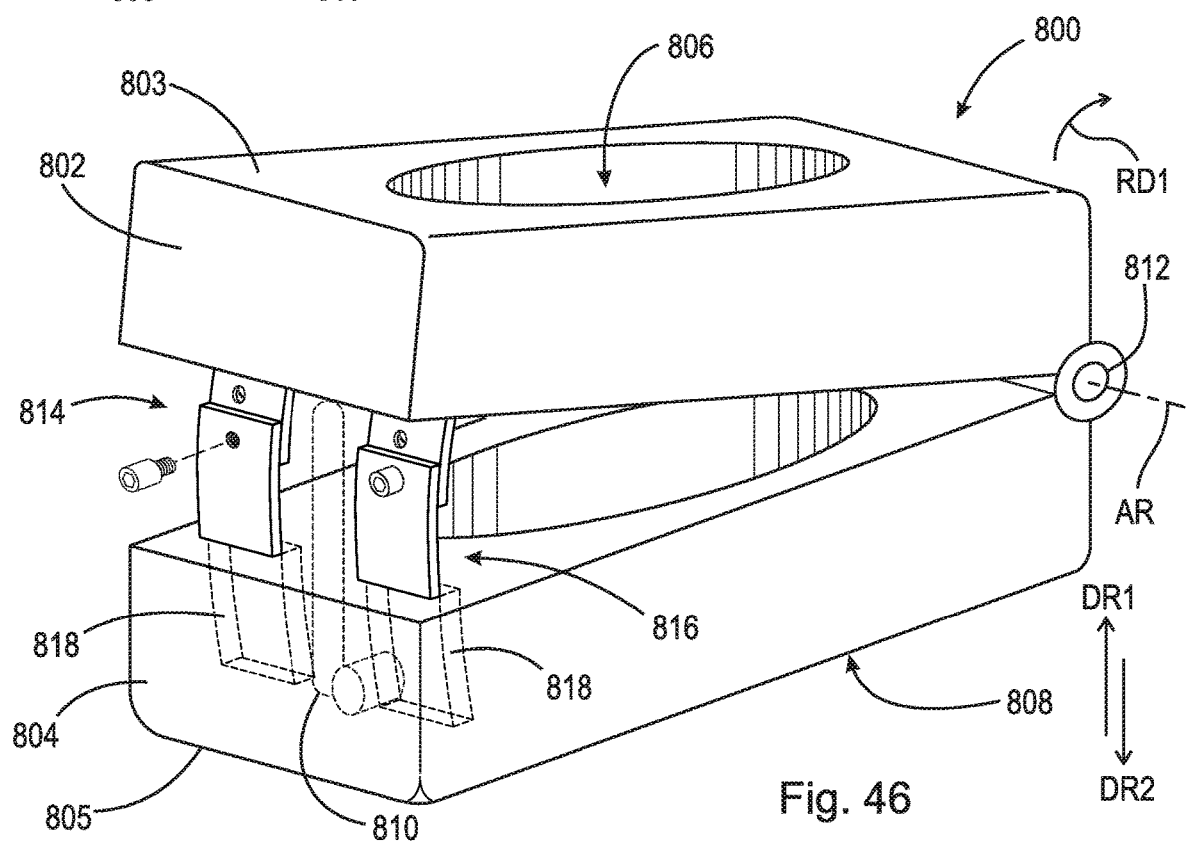
FIG. 46 is a front perspective view of a stand-alone expandable interbody spinal fusion device with an eighth embodiment of a locking mechanism in an expanded state.

FIG. 45 is a front perspective view of device 800 with locking mechanisms 814 and 816, in an unexpanded state. Device 800 comprises superior component 802, inferior component 804, and expansion mechanism 810 arranged to displace superior component 802 in a first direction DR1 relative to inferior component 804. Superior component 802 and inferior component 804 further comprise at least one first aperture 806 and at least one second aperture 808, which are arranged to allow fusion between bone fusing material and the adjacent vertebra. Superior component 802 has a first surface 803 and inferior component 804 has a first surface 805. Device 800 further comprises hinge 812 fixedly secured to superior component 802 and inferior component 804, and it is arranged to rotatably displace the superior component about axis of rotation AR. Locking mechanisms 814 and 816 are preferably locking mechanism 820 described supra. Expansion mechanism 810 is preferably expansion mechanism 176 described supra. It should be noted that since plates 822 and 824 are fixedly secured to superior and inferior components 802 and 804, respectively, recesses 818 are provided within which plates 822 and 824 can nest while device 800 is in a collapsed state. It should further be appreciated that plates 822 and 824 can be hingedly secured to superior component 802 and inferior component 804, respectively. FIG. 46 is a front perspective view of device 800 with locking mechanisms 814 and 816 in an expanded state.

Figure 47:
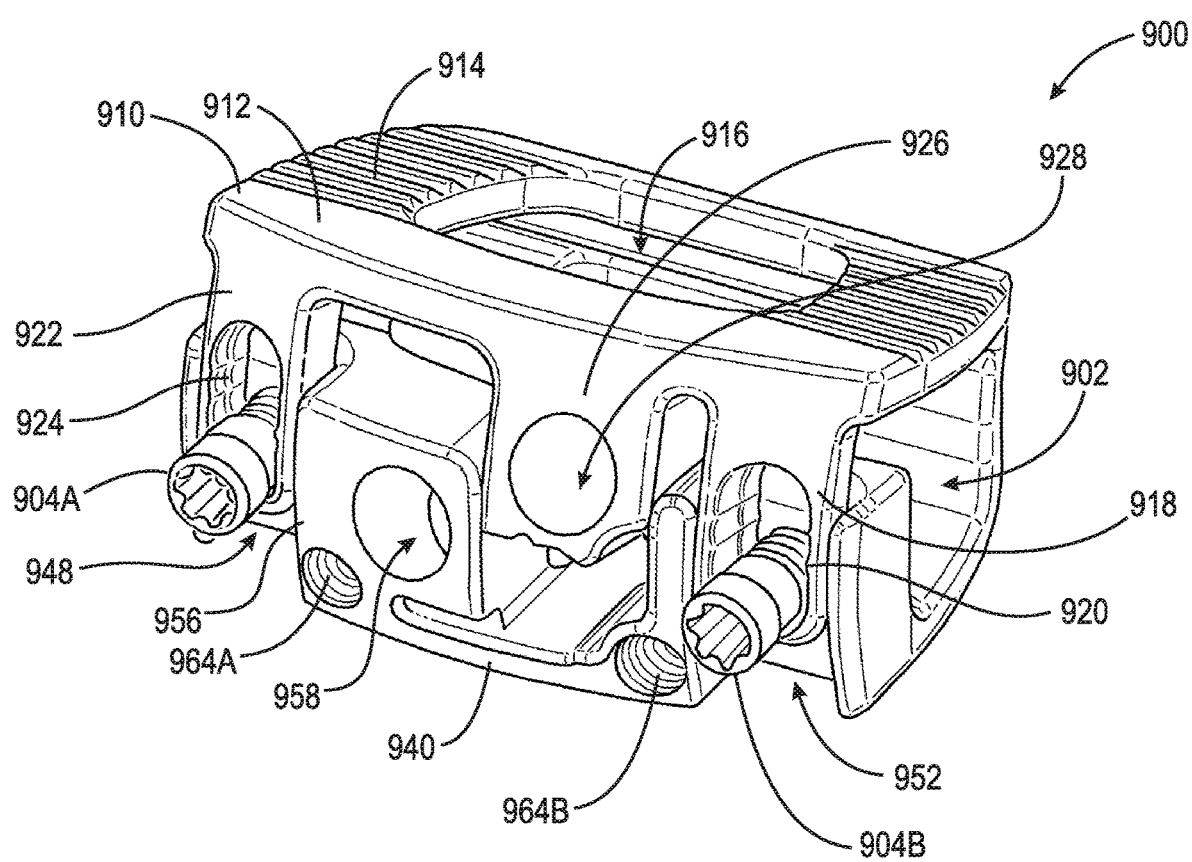
FIG. 47 is a front perspective view of a stand-alone expandable interbody spinal fusion device in an expanded state.
Figure 48:
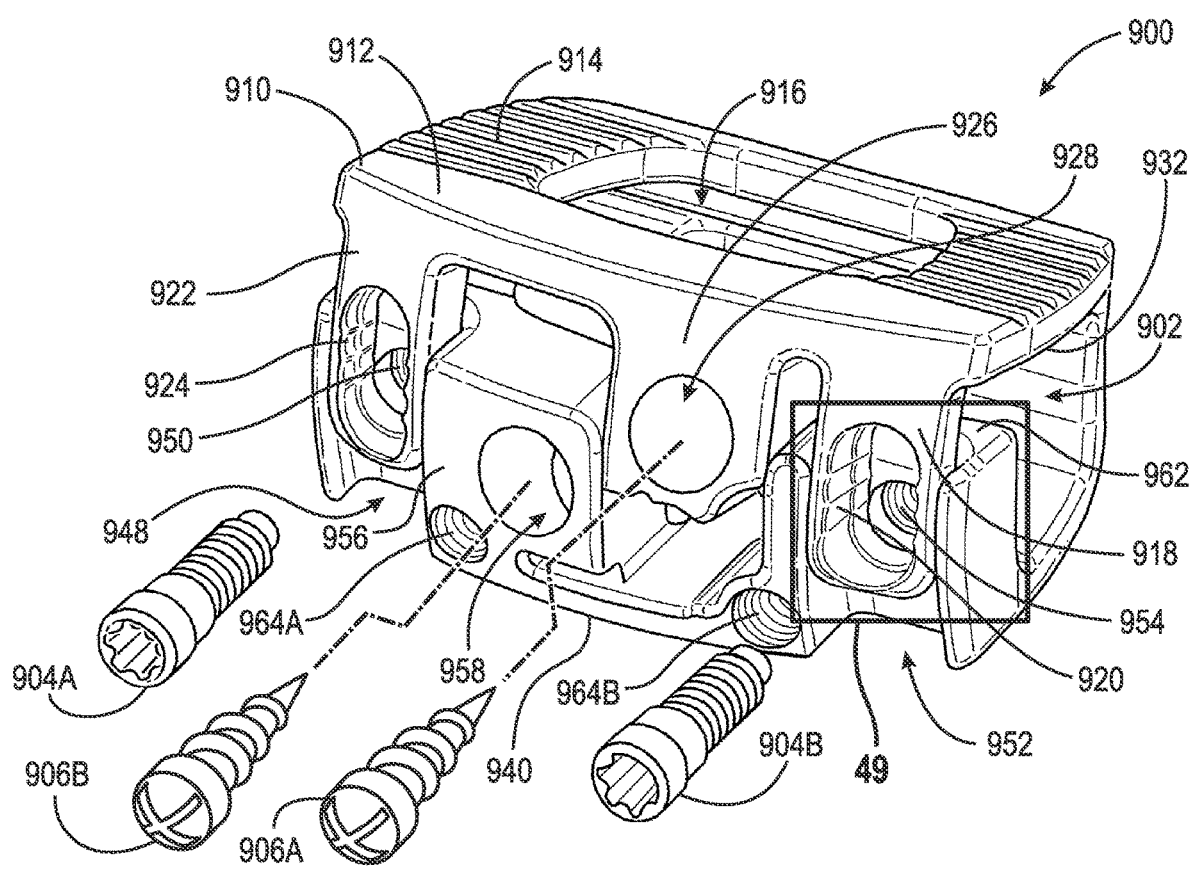
FIG. 48 is a partial exploded view of the stand-alone expandable interbody spinal fusion device shown in FIG. 47.
Figure 49:
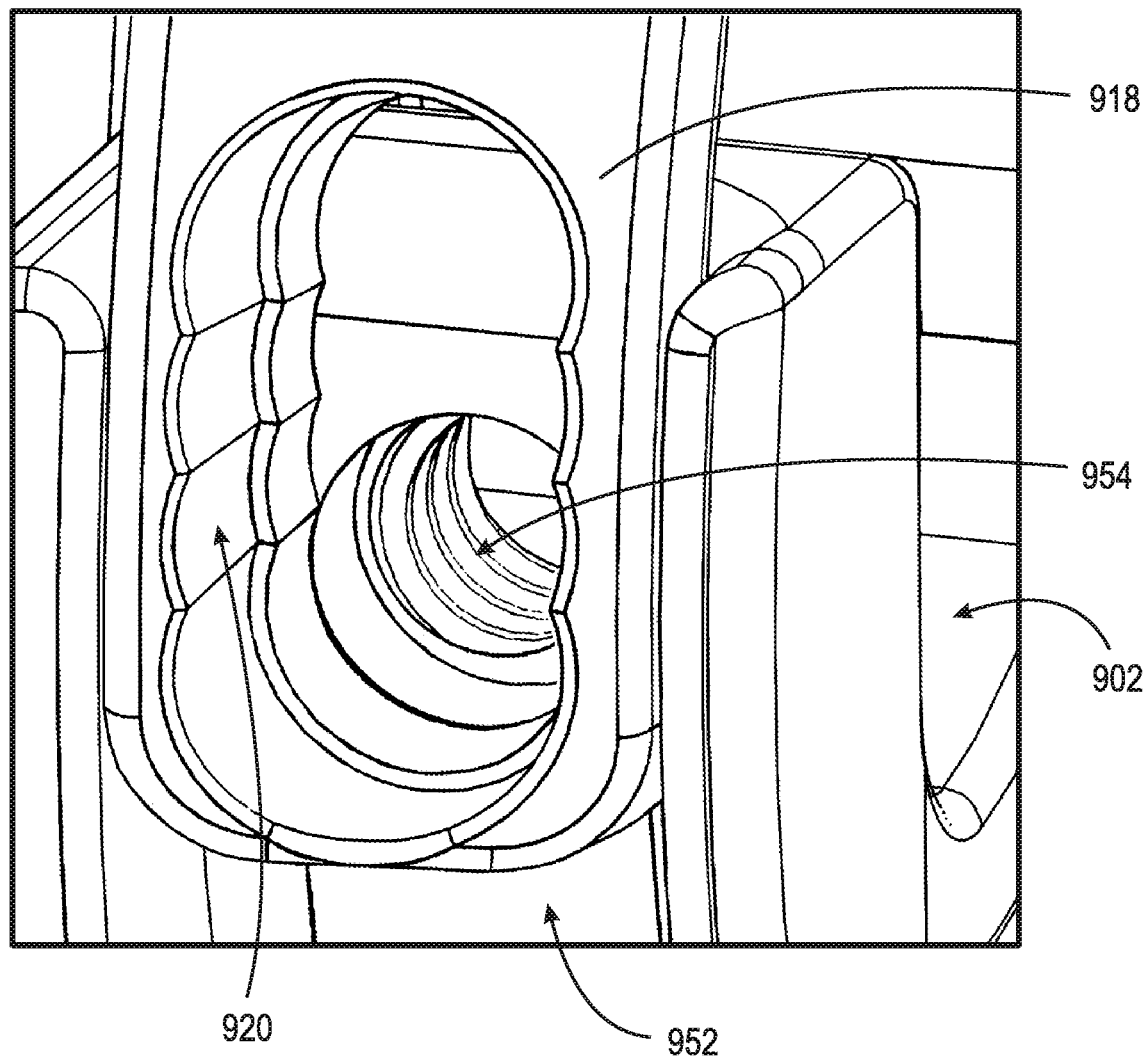
FIG. 49 is a detail view of the stand-alone expandable interbody spinal fusion device taken generally along detail 49 in FIG. 48.
Figure 50A:
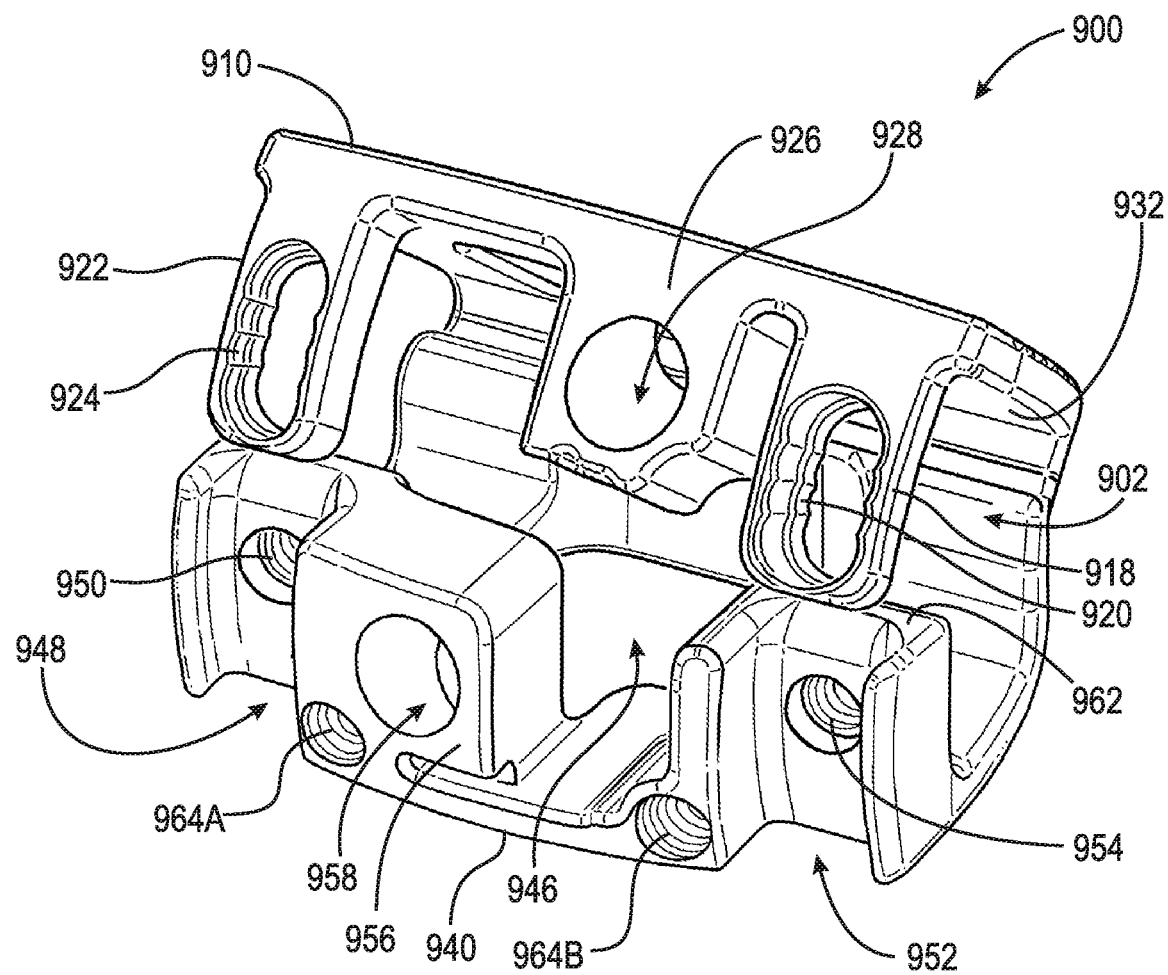
FIG. 50A is a front perspective view of the stand-alone expandable interbody spinal fusion device shown in FIG. 47.
Figure 50B:
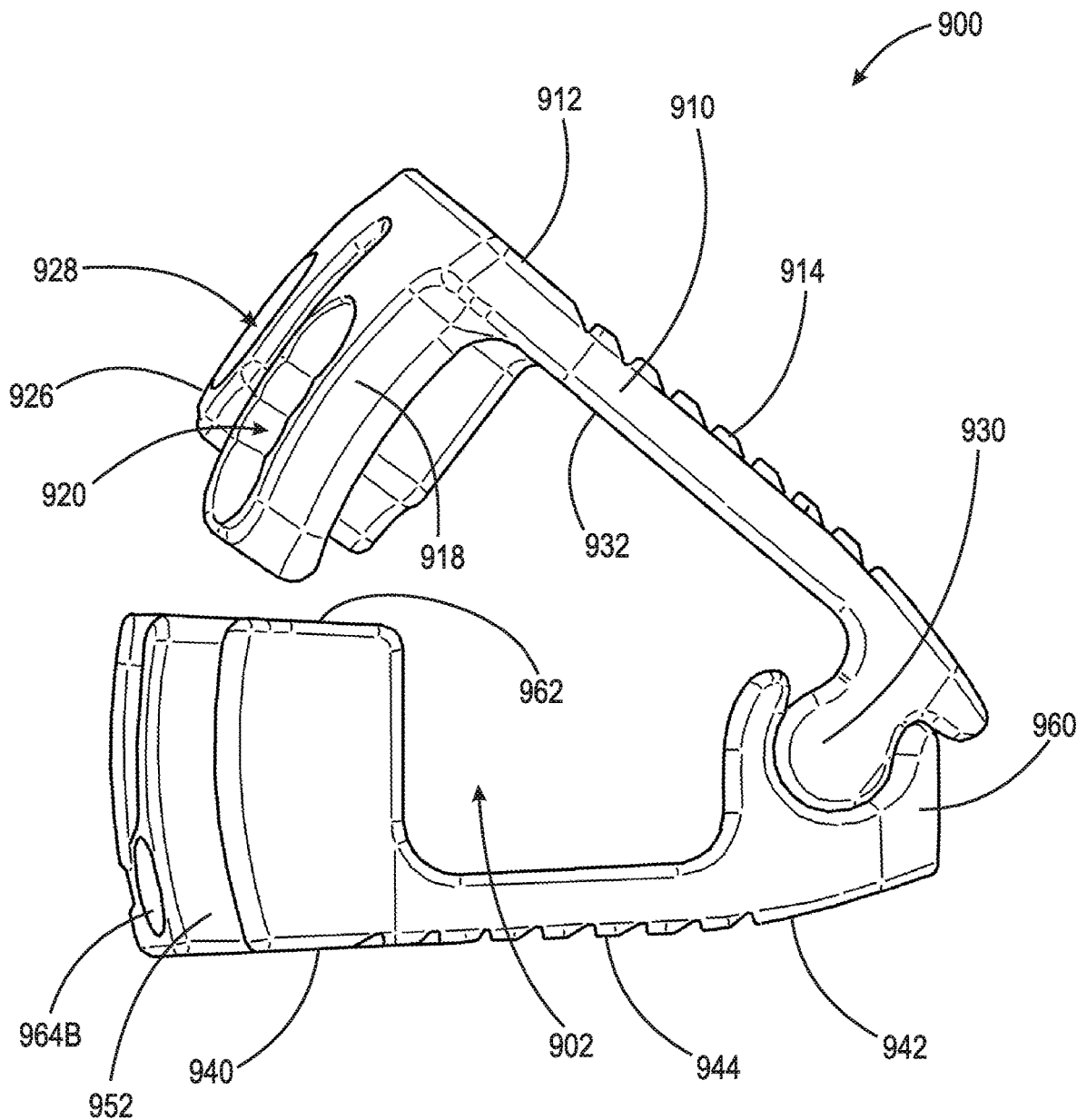
FIG. 50B is a side elevational view of the stand-alone expandable interbody spinal fusion device shown in FIG. 50A; and, FIG. 51 is a side elevational view of the stand-alone expandable interbody spinal fusion device shown in FIG. 47 in a collapsed state.
Figure 51:
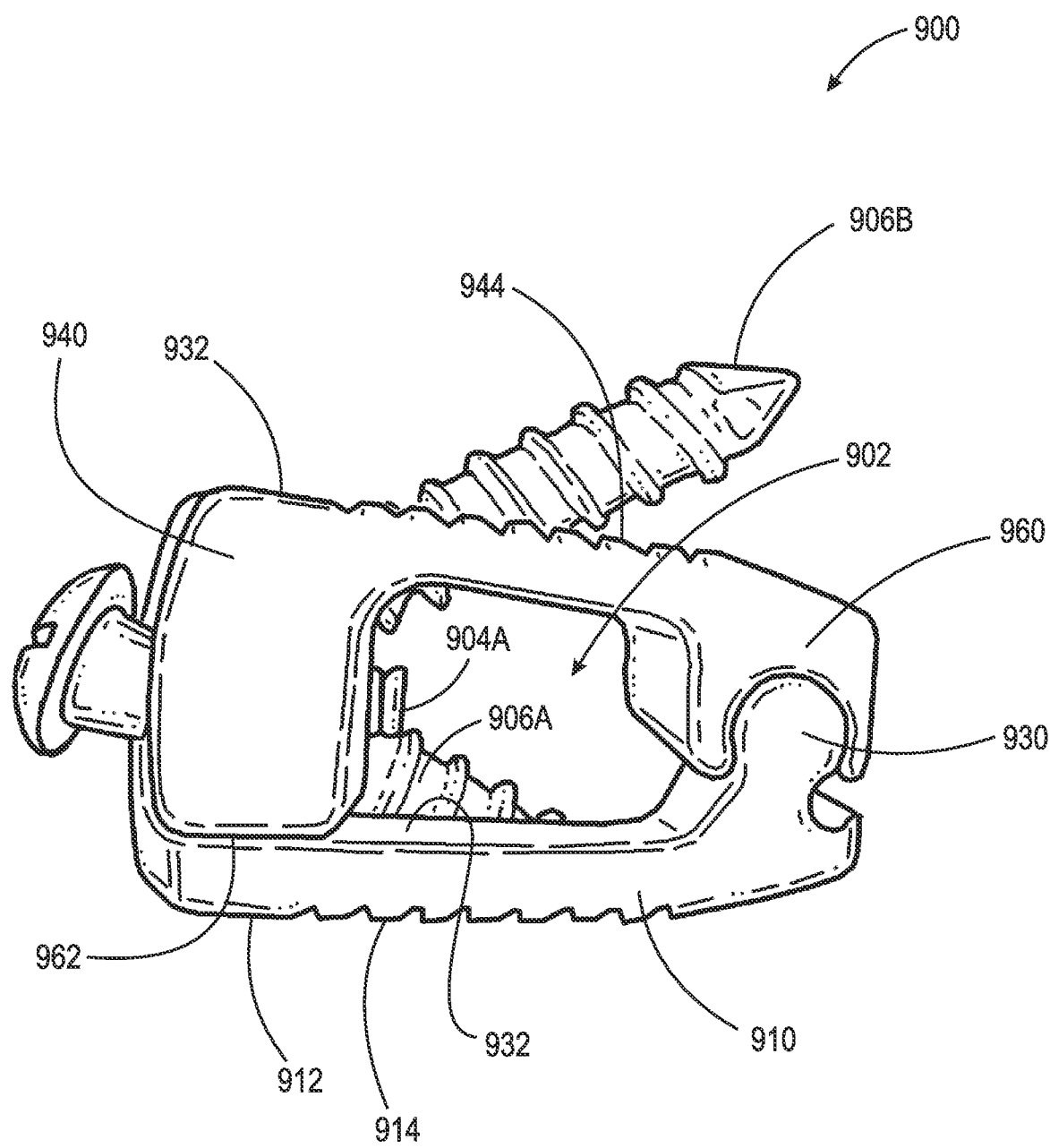

FIG. 47 is a front perspective view of expandable interbody spinal fusion device 900. FIG. 47 is a front perspective view of stand-alone expandable interbody spinal fusion device 900 in an expanded state. FIG. 48 is a partial exploded view of stand-alone expandable interbody spinal fusion device 900. FIG. 49 is a detail view of stand-alone expandable interbody spinal fusion device 900 taken generally along detail 49 in FIG. 48. FIG. 50A is a front perspective view of stand-alone expandable interbody spinal fusion device 900. FIG. 50B is a side elevational view of stand-alone expandable interbody spinal fusion device 900. FIG. 51 is a side elevational view of stand-alone expandable interbody spinal fusion device 900 in a collapsed state. Expandable interbody spinal fusion device 900 generally comprises superior component 910, inferior component 940, and one or more locking screws 904A-B. The following description should be read in view of FIGS. 47-51.

Superior component 910 comprises surface 912, protrusion 918, protrusion 922, protrusion 926, and hinge portion 930. Surface 912 is operatively arranged to engage a vertebra. Surface 912 may further comprise one or more ribs 914 and at least one aperture 916. Aperture 916 is arranged to allow bone material injected into cavity 902 to fuse with the adjacent vertebra. Protrusion 918 extends from surface 912 and engages with slot 952 of inferior component 940. Protrusion 918 comprises a plurality of catches 920. Protrusion 922 extends from surface 912 and engages with slot 948 of inferior component 940. Protrusion 922 comprises a plurality of catches 924. Protrusion 926 comprises through-bore 928. Through-bore 928 is designed such that screw 906A can pass therethrough and secure superior component 910 to the adjacent vertebra. In the embodiment shown, through-bore 928 is arranged at an angle to surface 912, said angle being greater than 0 degrees and less 90 degrees (see FIG. 51).

Inferior component 940 comprises surface 942, slot 948, slot 925, protrusion 956, and hinge portion 960. Surface 942 is operatively arranged to engage a vertebra. Surface 942 may further comprise one or more ribs 944 and at least one aperture 946. Aperture 946 is arranged to allow bone material injected into cavity 902 to fuse with the adjacent vertebra. Slot 948 is arranged to engage protrusion 922. Slot 948 comprises hole 950 which is operatively arranged to be aligned with one or more of plurality of catches 924. Slot 952 is arranged to engage protrusion 918. Slot 952 comprises hole 954, which is operatively arranged to be aligned with one or more of plurality of catches 920. Protrusion 956 comprises through-bore 958. Through-bore 958 is designed such that screw 906B can pass therethrough and secure inferior component 940 to the adjacent vertebra. In the embodiment shown, through-bore 958 is arranged at an angle to surface 942, said angle being greater than 0 degrees and less 90 degrees (see FIG. 51). Inferior component 940 may further comprise one or more ports 964A-B. Ports 964A-B are operatively arranged to be engaged by a tool such that the user (e.g., a surgeon) can hold expandable interbody spinal fusion device 900 in place between adjacent vertebrae (i.e., in place of the removed disc) while expanding superior component 910 with respect to inferior component 940.

When assembled, superior component 910 is hingedly secured to inferior component 940, and cavity 902 is formed therebetween. As shown, cup-shaped hinge portion 960 is arranged at least partially concentrically around pin-shaped hinge portion 930. In some embodiments, hinge portion 960 is pin-shaped and hinge portion 930 is cup-shaped, with hinge portion 930 concentrically arranged around hinge portion 960. In some embodiments, hinge portions 930 and 960 comprise through-bores through which a pin is passed, to form a normal pin-style hinge between superior component 910 and inferior component 940. Superior component 910 comprises surface 932 and inferior component 940 comprises surface 962. In a collapsed state, as shown in FIG. 51, surface 932 abuts against (or is arranged substantially proximate to) surface 962. In an expanded state, as shown in FIGS. 47-50B, surface 932 is spaced apart from surface 962. To expand expandable interbody spinal fusion device 900, locking screws 904A-B are removed and superior component 910 is hingedly expanded to a desired height. Once expandable interbody spinal fusion device 900 has been expanded to the desired height, locking screws 904A-B are reinserted to lock superior component 910 and inferior component 940. Specifically, locking screw 904A is inserted through the catch of plurality of catches 924 that is aligned with hole 950 and screwed into inferior component 940. As locking screw 904A is tightened in hole 950, a locking portion of locking screw 904A engages the aligned catch, thereby locking expandable interbody spinal fusion device 900 at its set height. Similarly, locking screw 904B is inserted through the catch of plurality of catches 920 that is aligned with hole 954 and screwed into inferior component 940. As locking screw 904B is tightened in hole 954, a locking portion of locking screw 904B engages the aligned catch thereby locking expandable interbody spinal fusion device 900 at its set height. Once expandable interbody spinal fusion device 900 is locked at its desired height, screws 906A-B are inserted through through-bores 928 and 958, respectively, securing superior component 910 and inferior component 940 to adjacent vertebrae. Expandable interbody spinal fusion device 900, specifically cavity 902, may then be filled with bone fusion material. In some embodiments, locking screws 904A-B are not arranged to be completely removed from inferior component 940, and comprise retention rings such that they cannot be removed from inferior component 940. In such embodiments, locking screws 904A-B are unscrewed from inferior component 940 until such is prevented by the retention rings, at which point the locking portion of locking screws 904A-B are clear of catches 924 and 920, respectively, and superior component 910 can be expanded/collapsed with respect to inferior component 940.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

LIST OF REFERENCE NUMERALS

- 10 Spinal column
- C1-C7 Cervical vertebrae
- T1-T9 Thoracic vertebrae
- L1-L5 Lumbar vertebrae
- S Sacrum
- C Coccyx
- D1 First diameter
- D2 Second diameter
- D3 Third diameter
- D4 Fourth diameter
- DR1 Direction
- DR2 Direction
- DR3 Direction
- DR4 Direction
- DL1-L2 Disc
- DL2-L3 Disc
- DL3-L4 Disc
- DL4-L5 Disc
- F Facet
- FJ Facet joint
- H1 Collapsed height
- H2 Expanded height
- SP Spinous process
- TP Transverse process
- IF Intervertebral foramen
- A Annulus
- AR Axis of rotation
- N Nucleus
- NC Neural canal
- H1 Unexpanded height
- H2 Expanded height
- RD1 Rotational direction 1
- RD2 Rotational direction 2
- 12 Disc space
- 100 Device
- 102 Superior component
- 103 First surface
- 104 Inferior component
- 105 Second surface
- 106 Expansion mechanism
- 108 Expansion mechanism
- 110 Expansion mechanism
- 112 Locking mechanism
- 114 Locking mechanism
- 116 Locking mechanism
- 118 Locking mechanism
- 120A Plate
- 120B Plate
- 120C Plate
- 120D Plate
- 120E Plate
- 120F Plate
- 120G Plate
- 120H Plate
- 122A Through-bores
- 122B Through-bores
- 122C Through-bores
- 122D Through-bores
- 122E Through-bores
- 122F Through-bores
- 122G Through-bores
- 122H Through-bores
- 124 First aperture
- 126 Second aperture
- 128 Post
- 130 Fastener
- 132 First end
- 134 Second end
- 136 Female threading
- 138 First section
- 140 Second section
- 142 Third section
- 144 Fourth section
- 146 Male threading
- 148 Stopping element
- 150 Longitudinal space
- 152 Post
- 154 Fastener
- 156 First end
- 158 Second end
- 160 Female threading
- 162 First section
- 164 Second section
- 166 Third section
- 168 Fourth section
- 170 Male threading
- 172 Stopping element
- 174 Longitudinal space
- 176 Expansion mechanism
- 178 Threaded rod
- 180 Threaded sleeve
- 182 Worm drive
- 184 Worm
- 186 Gear
- 200 Second embodiment
- 202 Superior component
- 203 First surface
- 204 Inferior component
- 205 Second surface
- 206 First aperture
- 208 Second Aperture
- 210 Expansion mechanism
- 212 Hinge
- 214 Locking Mechanism
- 216 Locking Mechanism
- 220 Locking mechanism
- 222 Plate
- 224 Pawl
- 226 Biasing element
- 228 Post
- 230 Fastener
- 232 First surface
- 234 Second surface
- 236 Corner
- 238 Hinge
- 240 Through-bore
- 242 First plurality of teeth
- 244 Second plurality of teeth
- 246 Through-bore
- 248 First pawl head
- 250 Second pawl head
- 252 Hinge
- 254 First protrusion
- 256 Second protrusion
- 258 First end
- 260 Second end
- 262 Male threading
- 264 Stopping element
- 266 First end
- 268 Second end
- 270 Female threading
- 276 Expansion mechanism 278 Threaded rod
280 Lifting nut
282 Worm drive
284 Worm
286 Gear
288 Platform
300 Device
302 Superior component
303 First surface
304 Inferior component
305 Second surface
306 First aperture
308 Second aperture
310 Expansion mechanism
312 Hinge
314 Locking Mechanism
316 Locking Mechanism
320 Locking mechanism
322 Plate
324 Post
326 Fastener
328 Corner
330 Hinge
332 Plurality of through-bores
334 Longitudinal space
336 First end
338 Second end
340 Male threading
342 Hinge
344 First protrusion
346 Second protrusion
348 First end
350 Second end
352 Flange
354 Female threading
420 Locking mechanism
422 Plate
424 Plate
426 Post
428 Fastener
430 Plurality of through-bores
432 Plurality of through-bores
434 Longitudinal space
436 Longitudinal space
438 First end
440 Second end
442 Male threading
444 Shoulder
446 Stopping element
448 First end
450 Second end
452 Female threading
400 Device
402 Superior component
403 First surface
404 Inferior component
405 Second surface
406 First aperture
408 Second aperture
410 Expansion mechanism
412 Hinge
414 Locking mechanism
416 Locking mechanism
418 Recess
500 Device
502 Superior component
503 First surface
504 Inferior component
505 Second surface
506 First aperture
508 Second aperture
510 Expansion mechanism
512 Hinge
514 Locking mechanism
516 Locking mechanism
518 Recess
520 Locking mechanism
522 Plate
524 Plate
526 Fastener
530 Plurality of through-bores
532 Plurality of through-bores
534 Longitudinal space
540 First end
542 Second end
544 Male threading
600 Device
602 Superior component
603 First surface
604 Inferior component
605 Second surface
606 Expansion mechanism
608 Expansion mechanism
610 Expansion mechanism
612 Locking mechanism
614 Locking mechanism
616 Locking mechanism
618 Locking mechanism
620A Plate
620B Plate
620C Plate
620D Plate
620E Plate
620F Plate
620G Plate
620H Plate
622A Through-bore
622B Through-bores
622C Through-bore
622D Through-bores
622E Square through-bore
622F Through-bores
622G Square through-bore
622H Through-bores
624 First aperture
626 Second aperture
628 Post
630 Fastener
632 First end
634 Second end
636 Flange
638 First section
640 Second section
642 Third section
644 Fourth section
646 Male threading
647 Cylindrical portion
648 Stopping element
650 Cavity
651 Female threading
652 Post
654 Fastener
656 First end
658 Second end 660 Flange
662 First section
664 Second section
666 Third section
668 Fourth section
670 Male threading
671 Cylindrical portion
672 Stopping element
674 Cavity
675 Female threading
700 Device
702 Superior component
703 First surface
704 Inferior component
705 Second surface
706 First aperture
708 Second aperture
710 Expansion mechanism
712 Hinge
714 Locking mechanism
716 Locking mechanism
718 Recess
720 Locking mechanism
722 Plate
724 Plate
726 Fastener
730 Plurality of catches
732 Through-bore
734 Female threading
740 First end
742 Second end
744 Male threading
800 Device
802 Superior component
803 First surface
804 Inferior component
805 Second surface
806 First aperture
808 Second aperture
810 Expansion mechanism
812 Hinge
814 Locking mechanism
816 Locking mechanism
818 Recess
820 Locking mechanism
822 Plate
824 Plate
826 Fastener
830 Plurality of catches
832 Through-bore
834 Female threading
840 First end
842 Second end
844 Male threading
900 Device
902 Cavity
904A Locking screw
904B Locking screw
906A Screw
906B Screw
910 Superior component
912 Surface
914 Ribs
916 Aperture
918 Protrusion
920 Catches
922 Protrusion
924 Catches
926 Protrusion
928 Through-bore
930 Hinge portion
932 Surface
940 Inferior component
942 Surface
944 Ribs
946 Aperture
948 Slot
950 Hole
952 Slot
954 Hole
956 Protrusion
958 Through-bore
960 Hinge portion
962 Surface
964A Port
964B Port

What is claimed is:

1. An expandable interbody spinal fusion device, comprising:
an inferior component including at least one hole;
a superior component connected to the inferior component, the superior component including a plurality of catches operatively arranged to align with the at least one hole; and,
a locking screw operatively arranged to extend through the plurality of catches and engage the at least one hole to lock the superior component with respect to the inferior component.

2. The expandable interbody spinal fusion device as recited in claim 1, wherein the superior component is hingedly connected to the inferior component.

3. The expandable interbody spinal fusion device as recited in claim 1, wherein the superior component comprises a first hinge portion and the inferior component comprises a second hinge portion, the second hinge portion being at least partially concentrically arranged around the first hinge portion.

4. The expandable interbody spinal fusion device as recited in claim 1, wherein the superior component further comprises a first surface including a first aperture.

5. The expandable interbody spinal fusion device as recited in claim 4, wherein the first surface comprises one or more ribs.

6. The expandable interbody spinal fusion device as recited in claim 1, wherein the inferior component further comprises a second surface including a second aperture.

7. The expandable interbody spinal fusion device as recited in claim 6, wherein the second surface comprises one or more ribs.

8. The expandable interbody spinal fusion device as recited in claim 1, wherein the at least one hole is arranged in a slot of the inferior component and the plurality of catches are arranged on a protrusion of the superior component, the protrusion being arranged to engage the slot.

9. The expandable interbody spinal fusion device as recited in claim 1, wherein the inferior component further comprises a first through-bore and the superior component further comprises a second through-bore, the first and second through-bore operatively arranged to engage screws.

10. The expandable interbody spinal fusion device as recited in claim 1, wherein the superior component and the inferior component form a cavity therebetween.

11. The expandable interbody spinal fusion device as recited in claim 1, wherein one of the inferior component and superior component comprises one or more ports.

12. The expandable interbody spinal fusion device as recited in claim 1, further comprising an expansion mechanism operatively arranged to displace the superior component in a first direction relative to the inferior component.

13. An expandable interbody spinal fusion device, comprising:
- an inferior component including a first surface and at least one hole;
- a superior component hingedly connected to the inferior component, the superior component including a second surface and a plurality of catches operatively arranged to align with the at least one hole;
- a cavity formed between the inferior component and the superior component; and,
- a locking screw operatively arranged to engage the plurality of catches and the at least one hole to lock the superior component with respect to the inferior component.

14. The expandable interbody spinal fusion device as recited in claim 13, wherein the superior component comprises a first hinge portion and the inferior component comprises a second hinge portion, the second hinge portion being at least partially concentrically arranged around the first hinge portion.

15. The expandable interbody spinal fusion device as recited in claim 13, wherein the first surface comprises a first aperture.

16. The expandable interbody spinal fusion device as recited in claim 13, wherein the second surface comprises a second aperture.

17. The expandable interbody spinal fusion device as recited in claim 13, wherein the at least one hole is arranged in a slot of the inferior component and the plurality of catches are arranged on a protrusion of the superior component, the protrusion being arranged to engage the slot.

18. The expandable interbody spinal fusion device as recited in claim 13, wherein:
- in a collapsed state, a third surface of the inferior component abuts against a fourth surface of the superior component; and,
- in an expanded state, the fourth surface is spaced apart from the third surface.

19. The expandable interbody spinal fusion device as recited in claim 13, wherein the inferior component further comprises a first through-bore and the superior component further comprises a second through-bore, the first and second through-bore operatively arranged to engage screws to secure the expandable interbody spinal fusion device to one or more vertebrae.

20. The expandable interbody spinal fusion device as recited in claim 13, wherein one of the inferior component and superior component comprises one or more ports.

* * * * *